(12) United States Patent
Evans et al.

(10) Patent No.: US 7,371,245 B2
(45) Date of Patent: May 13, 2008

(54) TRANSOBTURATOR INTRODUCER SYSTEM FOR SLING SUSPENSION SYSTEM

(75) Inventors: Douglas G. Evans, Snellville, GA (US); Ken Butcher, Conyers, GA (US); Tracey Knapp, Lawrenceville, GA (US)

(73) Assignee: C R Bard, Inc, Murray Hill, NJ (US)

( * ) Notice: Subject to any disclaimer, the term of this patent is extended or adjusted under 35 U.S.C. 154(b) by 194 days.

(21) Appl. No.: 11/148,877

(22) Filed: Jun. 8, 2005

(65) Prior Publication Data

US 2006/0015069 A1    Jan. 19, 2006

Related U.S. Application Data

(63) Continuation-in-part of application No. 10/633,254, filed on Aug. 1, 2003.

(60) rovisional application No. 60/578,552, filed on Jun. 9, 2004, provisional application No. 60/479,039, filed on Jun. 17, 2003, provisional application No. 60/400,616, filed on Aug. 2, 2002.

(51) Int. Cl.
*A61B 17/08* (2006.01)
*A61F 2/00* (2006.01)
*A61F 2/02* (2006.01)

(52) U.S. Cl. ...................... 606/151; 606/157

(58) Field of Classification Search ............... 606/120, 606/139, 144, 148, 151, 170, 205–211, 222–224; 600/29, 30, 37; 112/222–224, 48, 49; 81/487, 81/489, 491; 24/16 PB, 115 F, 328, 335, 24/336; 439/404, 409, 410, 436, 439, 883

See application file for complete search history.

(56) References Cited

U.S. PATENT DOCUMENTS 1,450,101 A    3/1923    Matthewson (Continued)

FOREIGN PATENT DOCUMENTS

DE    102 11 360    10/2003

(Continued)

OTHER PUBLICATIONS

Bryans, Fred E.; "Marlex gauze hammock sling operation with Cooper's ligament attachment in the management of recurrent urinary stress incontinence" 1979.

(Continued)

*Primary Examiner*—Julian W. Woo

(57) ABSTRACT

An introducer device comprising: an introducer needle having a proximal end and a distal end and a handle having a needle receiving end. The handle can be adapted to receive said distal end of said introducer needle such that said introducer needle is selectably detachably coupled to said handle. A connector for attachment to an implant strip can have an arm having a hole therethrough and an introducer needle including a connection portion having a barb. It can comprise a central portion; a first arm pivotally mounted to the central portion and having a first projection and a second projection extending therefrom. A second arm can be pivotally mounted to the central portion and having a first hole and a second hole defined therein. The first and second holes can be positioned so that when the first arm pivots toward the second arm, the first and second projections are received in the first and second holes. A tube portion can extend from said central portion and define a tube aperture therein. The tube aperture can be adapted to receive the barb such that the connector can be selectably detachably coupled or permanently affixed to the introducer needle.

1 Claim, 54 Drawing Sheets

U.S. PATENT DOCUMENTS

| | | | |
|---|---|---|---|
| 2,097,018 A | | 10/1937 | Chamberlin |
| 2,240,330 A | | 4/1941 | Flagg et al. |
| 2,518,994 A | * | 8/1950 | Miller ..................... 606/205 |
| 3,249,104 A | | 5/1966 | Hahnstein |
| 3,340,494 A | * | 9/1967 | Gutshall ................... 439/434 |
| 3,739,430 A | * | 6/1973 | Kohke ................... 24/16 PG |
| 3,913,179 A | | 10/1975 | Rhee |
| 3,976,351 A | * | 8/1976 | Hopfe ........................ 439/409 |
| 4,172,458 A | | 10/1979 | Pereyra |
| 4,258,716 A | * | 3/1981 | Sutherland ................ 606/170 |
| 4,655,221 A | | 4/1987 | Devereux |
| 4,775,380 A | | 10/1988 | Seedhom et al. |
| 4,784,139 A | | 11/1988 | Demos |
| 4,911,164 A | | 3/1990 | Roth |
| 4,938,760 A | | 7/1990 | Burton et al. |
| 5,013,292 A | | 5/1991 | Lemay |
| 5,112,344 A | | 5/1992 | Petros |
| 5,123,910 A | | 6/1992 | McIntosh |
| 5,149,329 A | | 9/1992 | Richardson |
| 5,152,778 A | * | 10/1992 | Bales et al. ................. 606/205 |
| 5,356,432 A | | 10/1994 | Rutkow et al. |
| 5,362,294 A | | 11/1994 | Seitzinger |
| 5,439,467 A | | 8/1995 | Benderev et al. |
| 5,474,543 A | | 12/1995 | McKay |
| 5,549,619 A | * | 8/1996 | Peters et al. ................ 606/151 |
| 5,562,689 A | | 10/1996 | Green et al. |
| 5,569,269 A | * | 10/1996 | Hart et al. ................... 606/144 |
| 5,647,836 A | | 7/1997 | Blake, III et al. |
| 5,689,860 A | * | 11/1997 | Matoba et al. ............. 24/115 F |
| 5,693,072 A | | 12/1997 | McIntosh |
| 5,817,128 A | * | 10/1998 | Storz ......................... 606/205 |
| 5,830,220 A | | 11/1998 | Wan et al. |
| 5,836,053 A | * | 11/1998 | Davignon et al. ........ 24/16 PB |
| 5,840,011 A | | 11/1998 | Landgrebe et al. |
| 5,860,425 A | | 1/1999 | Benderev et al. |
| 5,899,909 A | | 5/1999 | Claren et al. |
| 5,904,692 A | | 5/1999 | Steckel et al. |
| 5,910,148 A | * | 6/1999 | Reimels et al. ............. 606/144 |
| 5,934,283 A | | 8/1999 | Willem et al. |
| 5,971,967 A | | 10/1999 | Willard |
| 6,030,393 A | | 2/2000 | Corlew |
| 6,042,534 A | | 3/2000 | Gellman et al. |
| 6,042,536 A | | 3/2000 | Tihon et al. |
| 6,063,094 A | | 5/2000 | Rosenberg |
| 6,068,591 A | | 5/2000 | Bruckner et al. |
| 6,110,101 A | | 8/2000 | Tihon et al. |
| 6,197,036 B1 | | 3/2001 | Tripp et al. |
| 6,221,060 B1 | | 4/2001 | Willard |
| 6,273,852 B1 | | 8/2001 | Lehe et al. |
| 6,306,079 B1 | | 10/2001 | Trabucco |
| 6,382,214 B1 | | 5/2002 | Raz et al. |
| 6,406,423 B1 | | 6/2002 | Scetbon |
| 6,440,154 B2 | | 8/2002 | Gellman et al. |
| 6,475,139 B1 | | 11/2002 | Miller |
| 6,491,703 B1 | | 12/2002 | Ulmsten |
| 6,494,887 B1 | | 12/2002 | Kaladelfos |
| 6,517,552 B1 | * | 2/2003 | Nord et al. ................. 606/144 |
| 6,582,443 B2 | * | 6/2003 | Cabak et al. ............... 606/151 |
| 6,591,838 B2 | | 7/2003 | Durgin |
| 6,592,515 B2 | | 7/2003 | Thierfelder et al. |
| 6,605,097 B1 | | 8/2003 | Lehe et al. |
| 6,612,977 B2 | | 9/2003 | Staskin et al. |
| 6,638,209 B2 | | 10/2003 | Landgrebe |
| 6,638,210 B2 | | 10/2003 | Berger |
| 6,638,211 B2 | | 10/2003 | Suslian et al. |
| 6,641,525 B2 | | 11/2003 | Rocheleau et al. |
| 6,689,047 B2 | | 2/2004 | Gellman |
| 6,691,711 B2 | | 2/2004 | Raz et al. |
| 6,911,003 B2 | | 6/2005 | Anderson et al. |
| 2001/0049467 A1 | | 12/2001 | Lehe et al. |
| 2001/0053916 A1 | | 12/2001 | Rioux |
| 2002/0007222 A1 | | 1/2002 | Desai |
| 2002/0072694 A1 | | 6/2002 | Snitkin et al. |
| 2002/0077526 A1 | | 6/2002 | Kammerer et al. |
| 2002/0147382 A1 | | 10/2002 | Neisz et al. |
| 2002/0188169 A1 | | 12/2002 | Kammerer et al. |
| 2003/0023138 A1 | | 1/2003 | Luscombe |
| 2003/0050530 A1 | | 3/2003 | Neisz et al. |
| 2003/0065246 A1 | | 4/2003 | Inman et al. |
| 2003/0171644 A1 | | 9/2003 | Anderson et al. |
| 2003/0176762 A1 | | 9/2003 | Kammerer |
| 2003/0176875 A1 | | 9/2003 | Anderson et al. |
| 2003/0199732 A1 | | 10/2003 | Suslian et al. |
| 2003/0216693 A1 | | 11/2003 | Mickley |
| 2004/0097974 A1 | | 5/2004 | De Leval |
| 2004/0133217 A1 | | 7/2004 | Watschke |
| 2005/0075660 A1 | | 4/2005 | Chu et al. |

FOREIGN PATENT DOCUMENTS

| | | |
|---|---|---|
| EP | 0 437 481 B | 3/1995 |
| EP | 0 745 351 A | 12/1996 |
| EP | 0 556 313 B | 3/1997 |
| EP | 0 740 925 B | 3/1999 |
| EP | 0 778 749 | 12/2000 |
| EP | 1 151 722 A | 11/2001 |
| EP | 1 159 921 A | 12/2001 |
| EP | 0 854 691 B | 1/2002 |
| EP | 0 983 033 A | 10/2002 |
| EP | 1 342 454 | 9/2003 |
| WO | WO 90/03766 | 4/1990 |
| WO | WO 96/06567 | 3/1996 |
| WO | WO 97/13465 | 4/1997 |
| WO | WO 97/16121 | 5/1997 |
| WO | WO 98/35632 | 8/1998 |
| WO | WO 00/18325 | 4/2000 |
| WO | WO 00/27304 | 5/2000 |
| WO | WO 00/66030 | 11/2000 |
| WO | WO 00/74594 A1 | 12/2000 |
| WO | WO 00/74613 A1 | 12/2000 |
| WO | WO 00/74633 A2 | 12/2000 |
| WO | WO 01/52750 | 7/2001 |
| WO | WO 02/02031 | 1/2002 |
| WO | WO 02/19946 | 3/2002 |
| WO | WO 02/26108 | 4/2002 |
| WO | WO 02/28312 | 4/2002 |
| WO | WO 02/28315 | 4/2002 |
| WO | WO 02/39914 A1 | 5/2002 |
| WO | WO 02/058562 A1 | 8/2002 |
| WO | WO 02/058563 A1 | 8/2002 |
| WO | WO 02/058564 A2 | 8/2002 |
| WO | WO 02/058565 A2 | 8/2002 |
| WO | WO 02/062237 | 8/2002 |
| WO | WO 02/065921 A1 | 8/2002 |
| WO | WO 02/065922 A1 | 8/2002 |
| WO | WO 02/065923 A1 | 8/2002 |
| WO | WO 02/071931 A1 | 9/2002 |
| WO | WO 02/098322 A1 | 12/2002 |
| WO | WO 03/002027 A1 | 1/2003 |
| WO | WO 03/013369 A1 | 2/2003 |
| WO | WO 03/068107 A1 | 8/2003 |
| WO | WO 03/075792 A1 | 9/2003 |
| WO | WO 03/092546 A2 | 11/2003 |
| WO | WO 03/096928 | 11/2003 |
| WO | WO 03/096930 | 11/2003 |
| WO | WO 2004/016196 | 2/2004 |
| WO | WO 2004/019786 | 3/2004 |

OTHER PUBLICATIONS

Burch, John C.; "Urethrovaginal fixation to Cooper's ligament for correction of stress incontinence, cystocele, and prolapse", publication date unknown.

Falconer, C., Ekman-Ordeberg, G., Malmstrom, A., Ulmsten, U.; "Clinical Outcome and Changes in Connective Tissue Metabolism After Intravaginal Slingplasty in Stress Incontinent Women"; The International Urogynecology Journal; 1996.

Falconer, C., Soderberg, M., Blomgren, B., Ulmsten, U.; "Influence of Different Sling Materials on Connective Tissue Metabolism in Stress Urinary Incontinent Women"; The International Urogynecology Journal; 2001.

Horbach, Nicolette S.; "Suburethral Sling Procedures"; Urogynecology and Urodynamics Theory and Practice Fourth Edition; 1996.

Karram, Mickey M., Bhatia, Narender N.; "Patch procedure: Modified Transvaginal Fascia Lata Sling for recurrent or severe stress urinary incontinence"; Mar. 1990.

Kersey J.; "The gauze hammock sling operation in the treatment of stress incontinence"; British Journal of Obstetrics and Gynaecology; vol. 90 pp. 945-949; Oct. 1983.

Korda, Andrew; Peat, Brian; Hunter, Peter; "Experience with Silastic Slings for Female Urinary Incontinence"; Aust NZ J Obstet Gynaecol 1989.

Lichtenstein, Irving L., Shulman, Alex G., Amid, Parviz K., Montllor, Michele M.; "The Tension-Free Hernioplasty"; The American Journal of Surgery vol. 157; Feb. 1989.

McIndoe, G.A.J., Jones, R.W., Grieve B.W.; "The Aldridge Sling Procedure in the Treatment of Urinary Stress Incontinence"; Aust NZ J Obstet Gynaecol; 1987.

Morgan, J.E.; "A sling operation, using Marlex polypropylene mesh, for treatment of recurrent strss incontinence"; publication date unknown.

Narik, G., Palmrich, A.H.; "A simplified sling operation suitable for routine use"; publication date unknown.

Nichols, David H.; "The Mersilene Mesh Gauze-Hammock For Severe Urinary Stress Incontinence"; Obstetrics and Gynecology; publication date unknown.

Norris, Jeffrey P., Breslin, David S., Staskin, David R.; "Use of Synthetic Material in Sling Surgery: A Minimally Invasive Approach"; Journal of Endourology; vol. 10, No. 3, Jun. 1996.

O'Donnell, Pat D.; "Combined Raz Urethral Suspension and McGuire Pubovaginal Sling for Treatment of Complicated Stress Urinary Incontinence"; Jan. 1992.

Raz, Shlomo; Female Urology; Second Edition; 1996.

Ridley, John H.; "Appraisal of the Goebell-Frangenheim-Stoeckel sling procedure"; publication date unknown.

Stanton, Stuart L.; "Suprapubic Approaches for Stress Incontinence in Women"; publication date unknown.

Staskin, David R., Choe, Jong M., Breslin, David S.; "The Gore-Tex sling procedure for female sphincteric incontinence: indications, technique, and results"; World J. Urol.; 1997.

Choe, Jong M., Staskin, David R.; "Gore-Tex Patch Sling: 7 Years Later"; 1999.

Cook; Urogynecology; Product Technical Datasheet and Order form.

Walters, Mark D.; "Percutaneous Suburethral Slings: State of the Art"; publication date unknown.

International Search Report for appln. PCT/03/24212 (May 24, 2004).

Written Opinion for appln. PCT/03/24212 (Aug. 24, 2004).

PCT/US05/20167, PCT/US05/20167 Search Report.

* cited by examiner

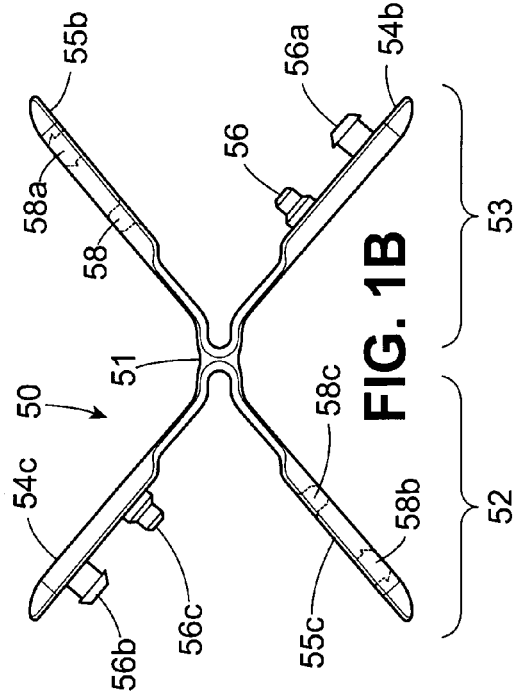
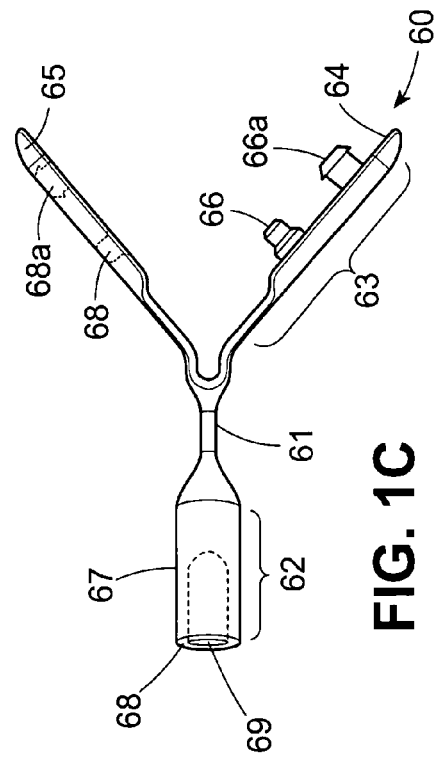
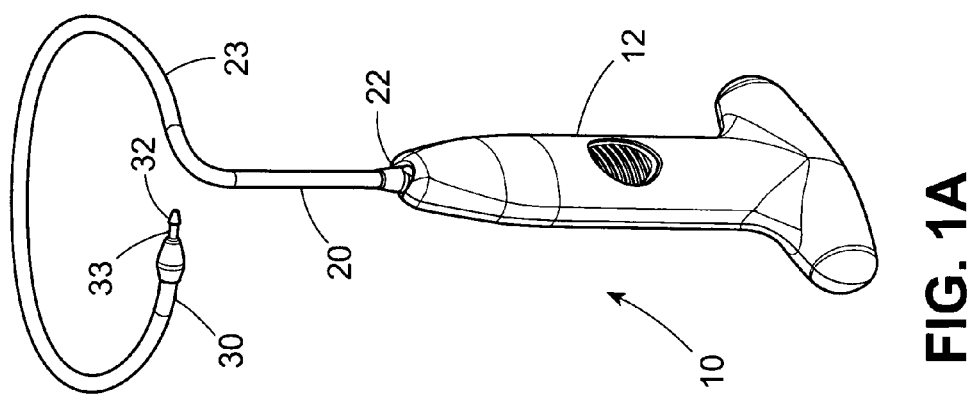

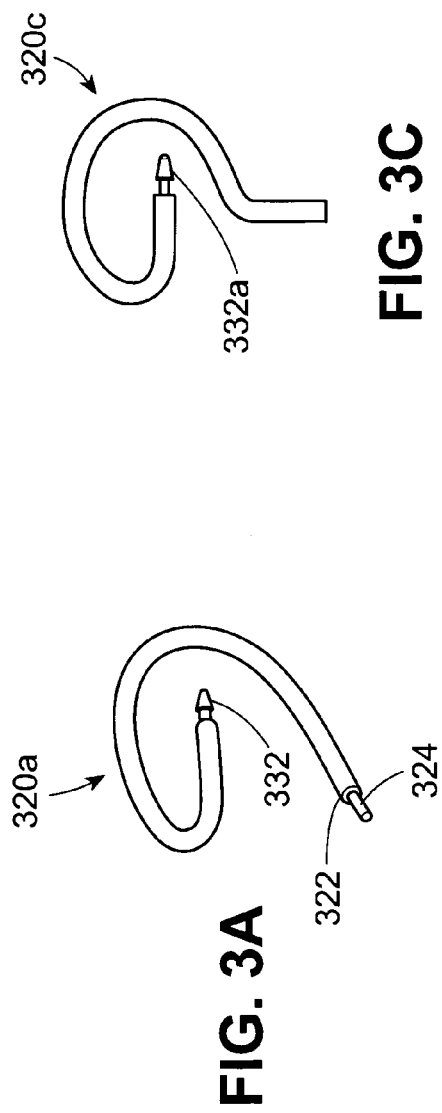
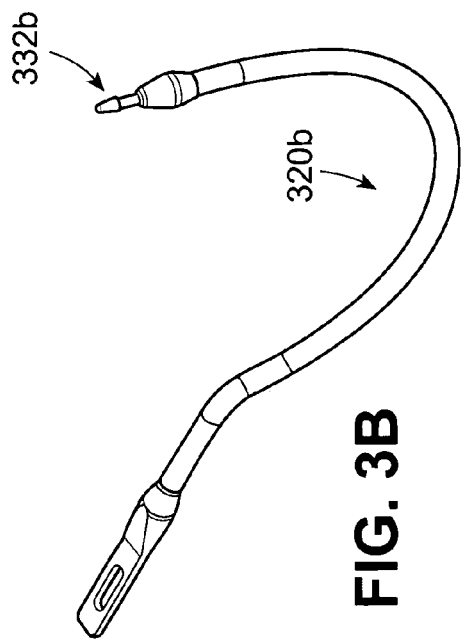
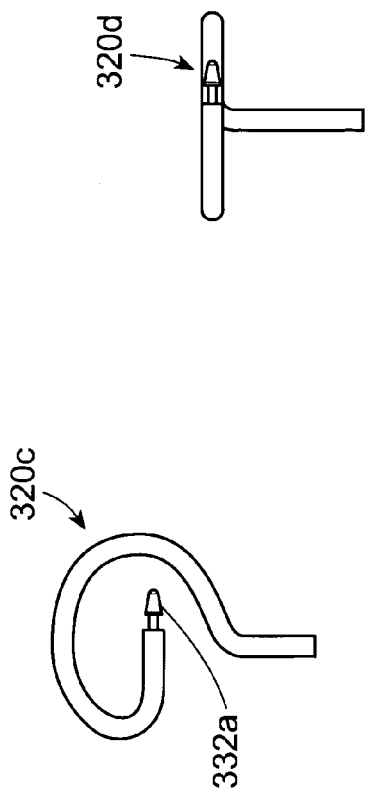
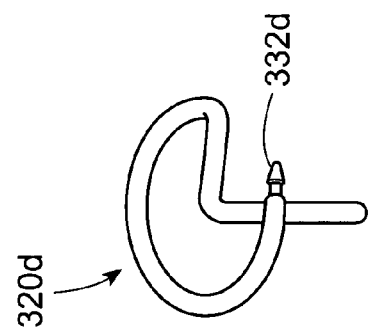
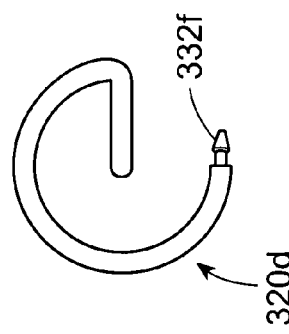

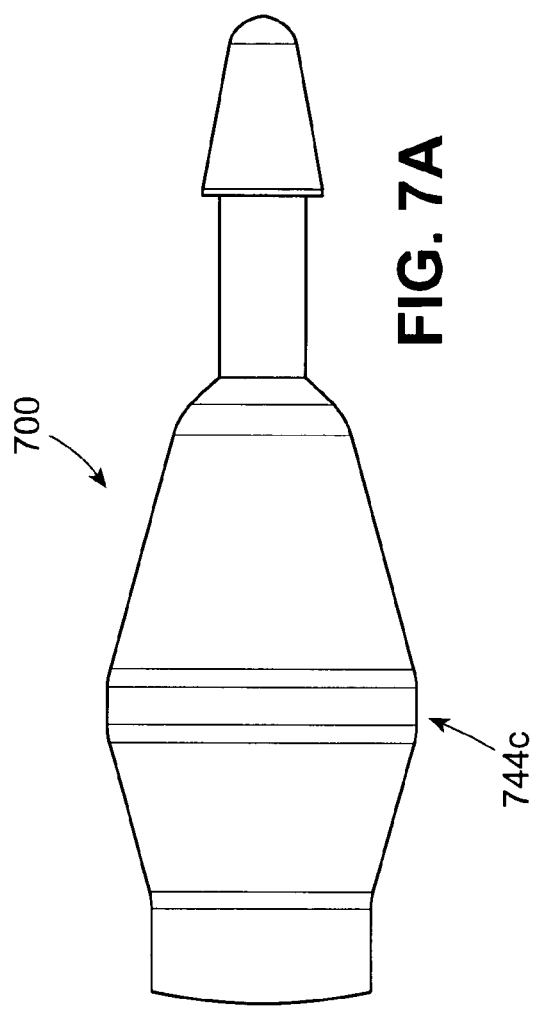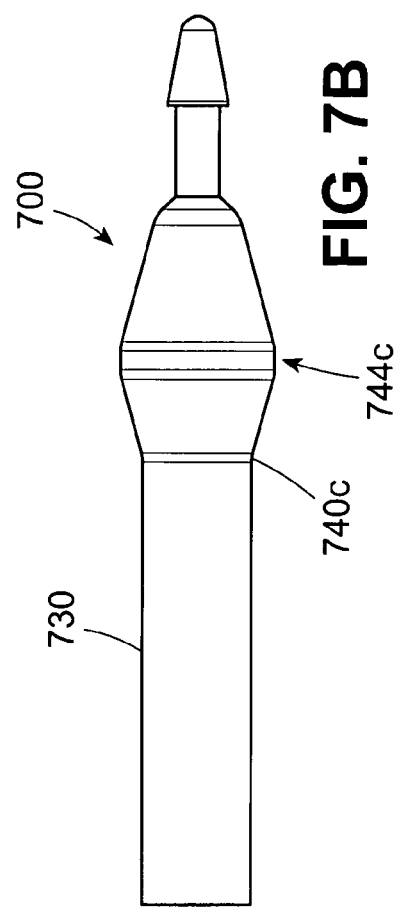

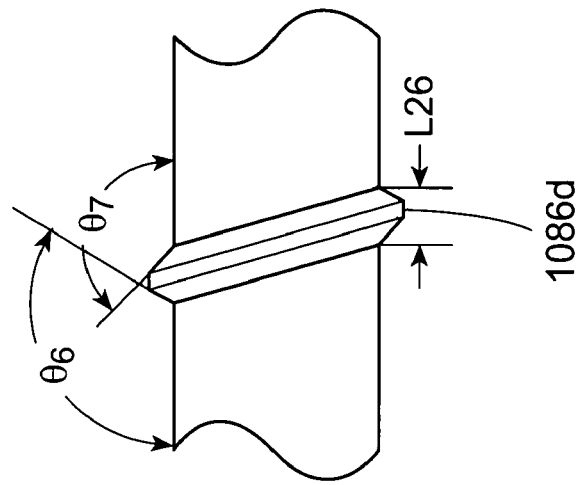
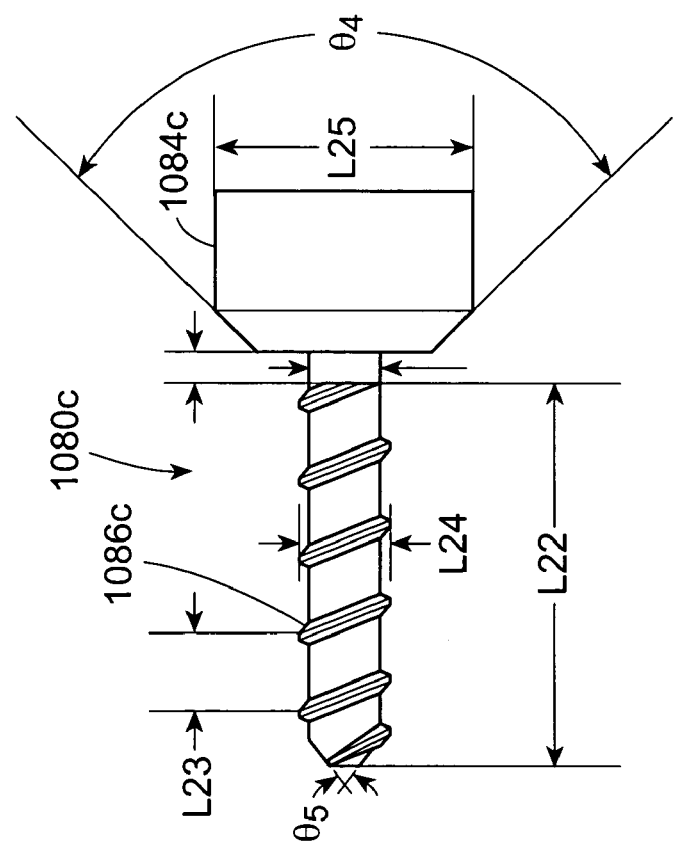
FIG. 10D
FIG. 10C

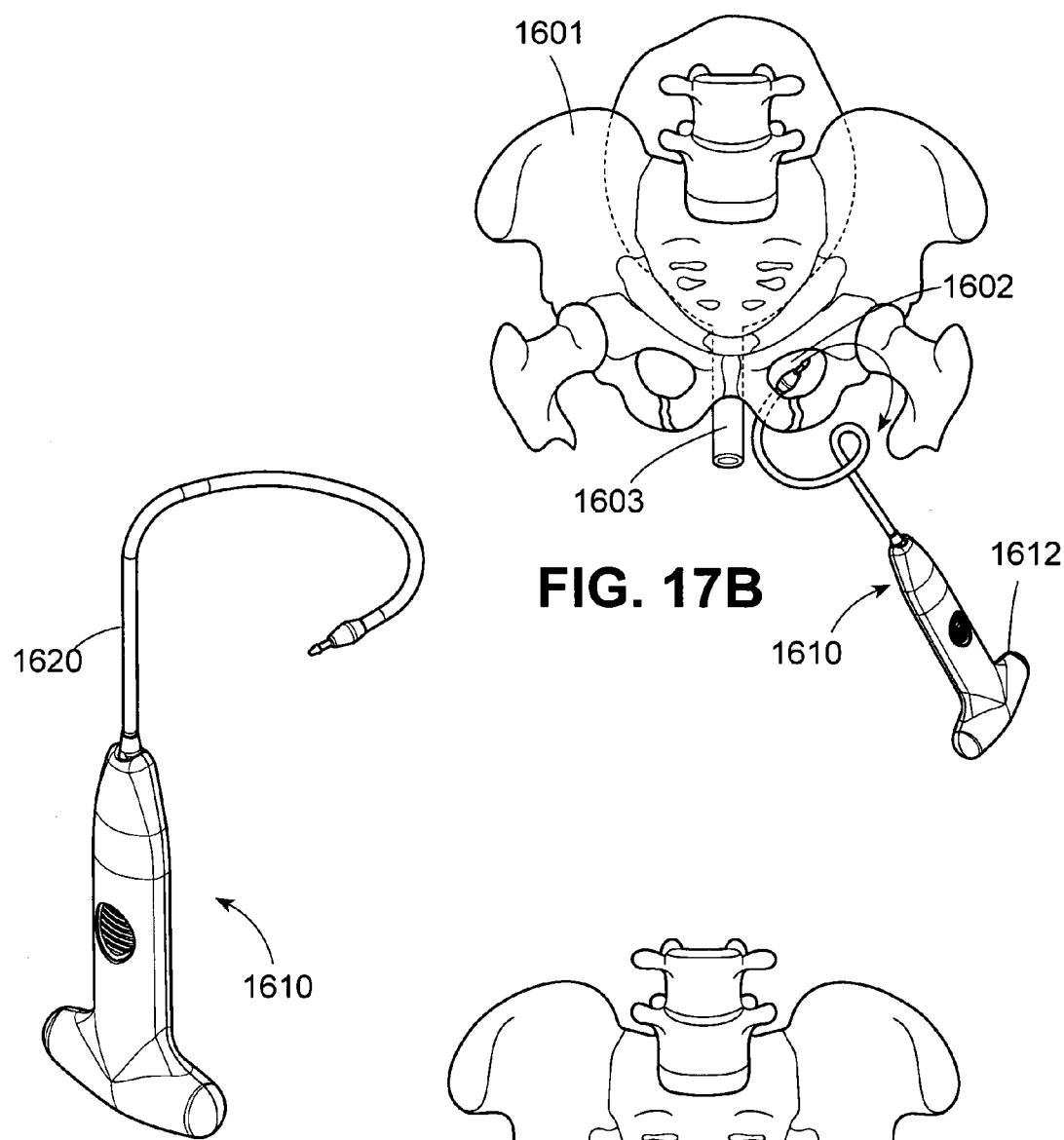
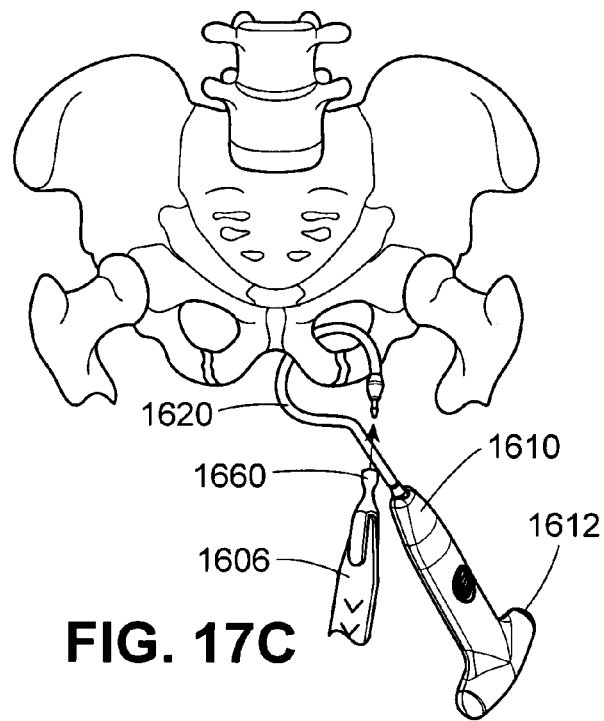
FIG. 17A
FIG. 17B
FIG. 17C

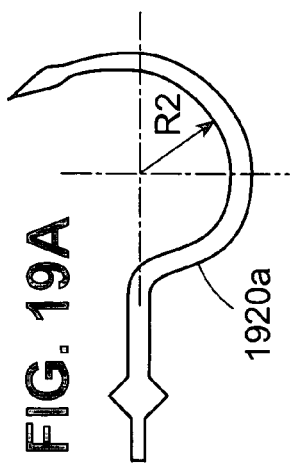
FIG. 18A
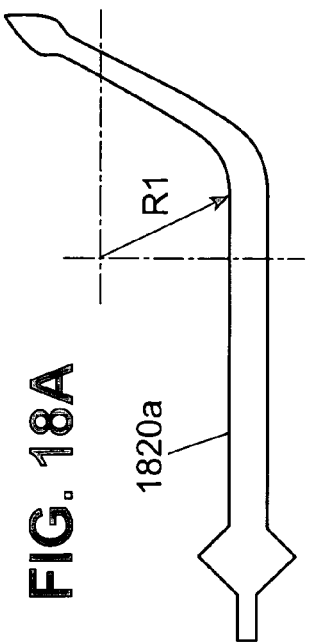
FIG. 18B
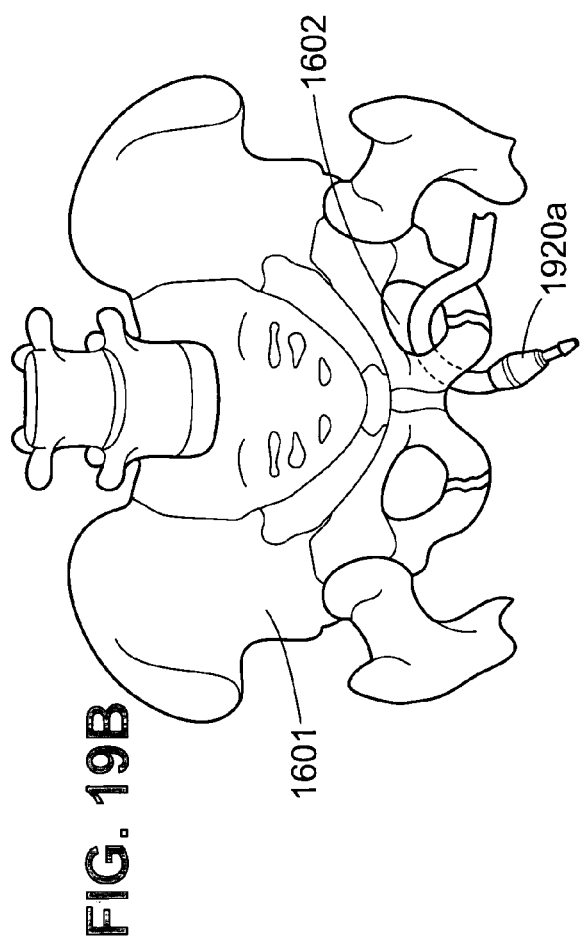
FIG. 19A
FIG. 19B
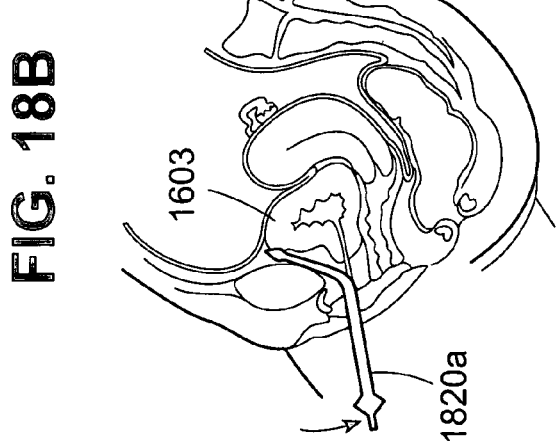

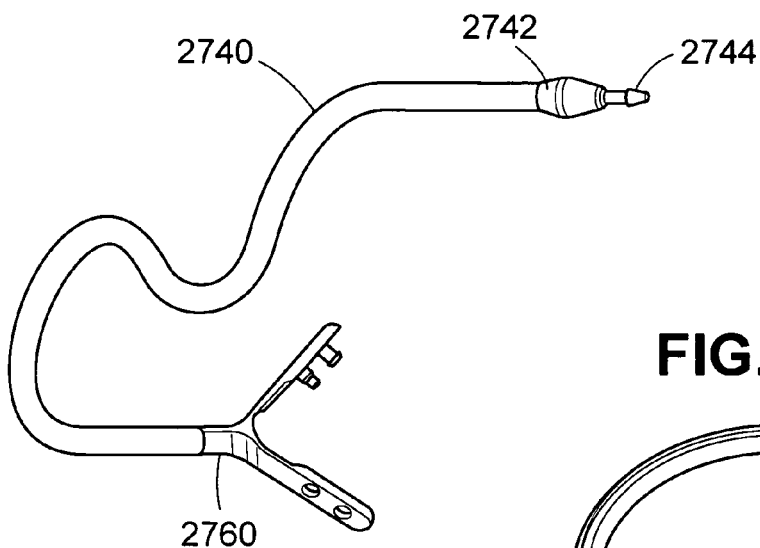
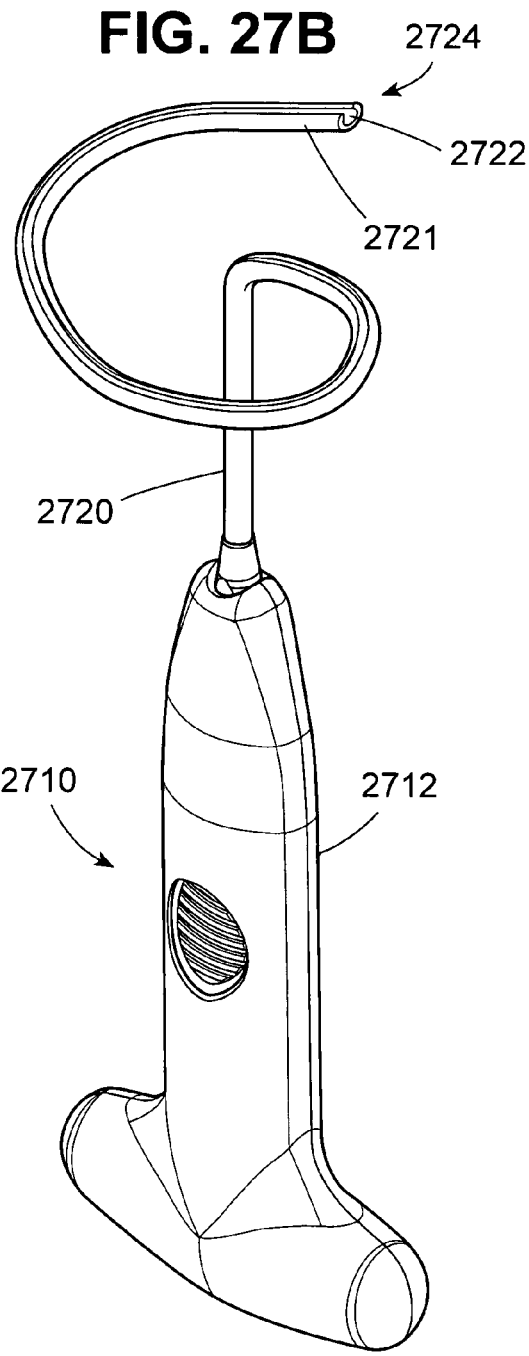
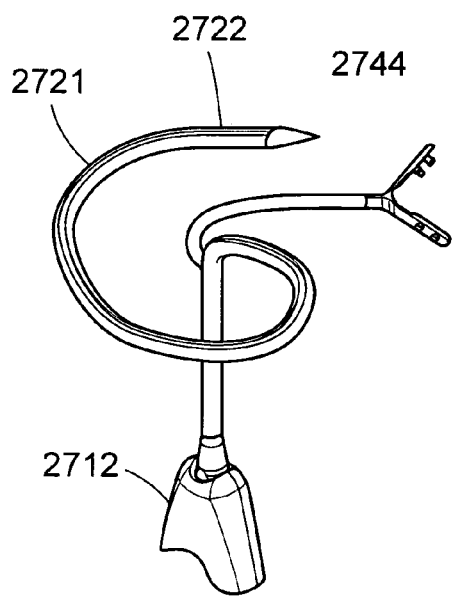
FIG. 27A
FIG. 27B
FIG. 27C

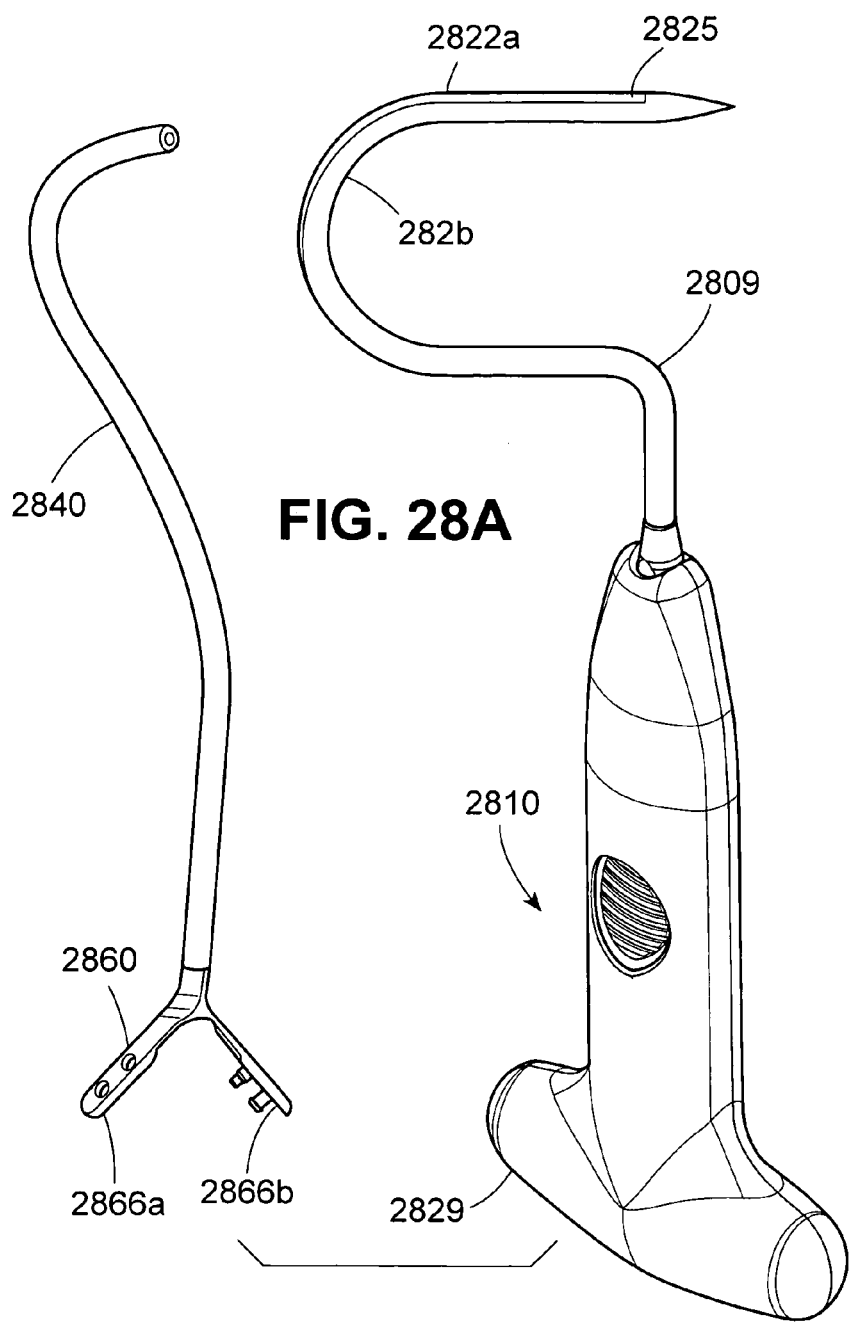
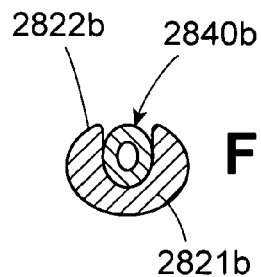
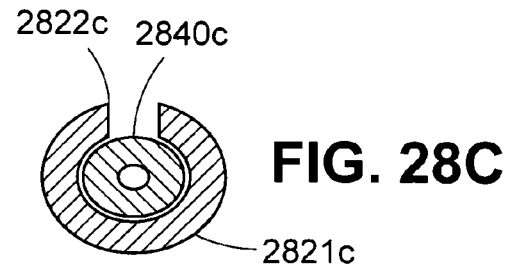

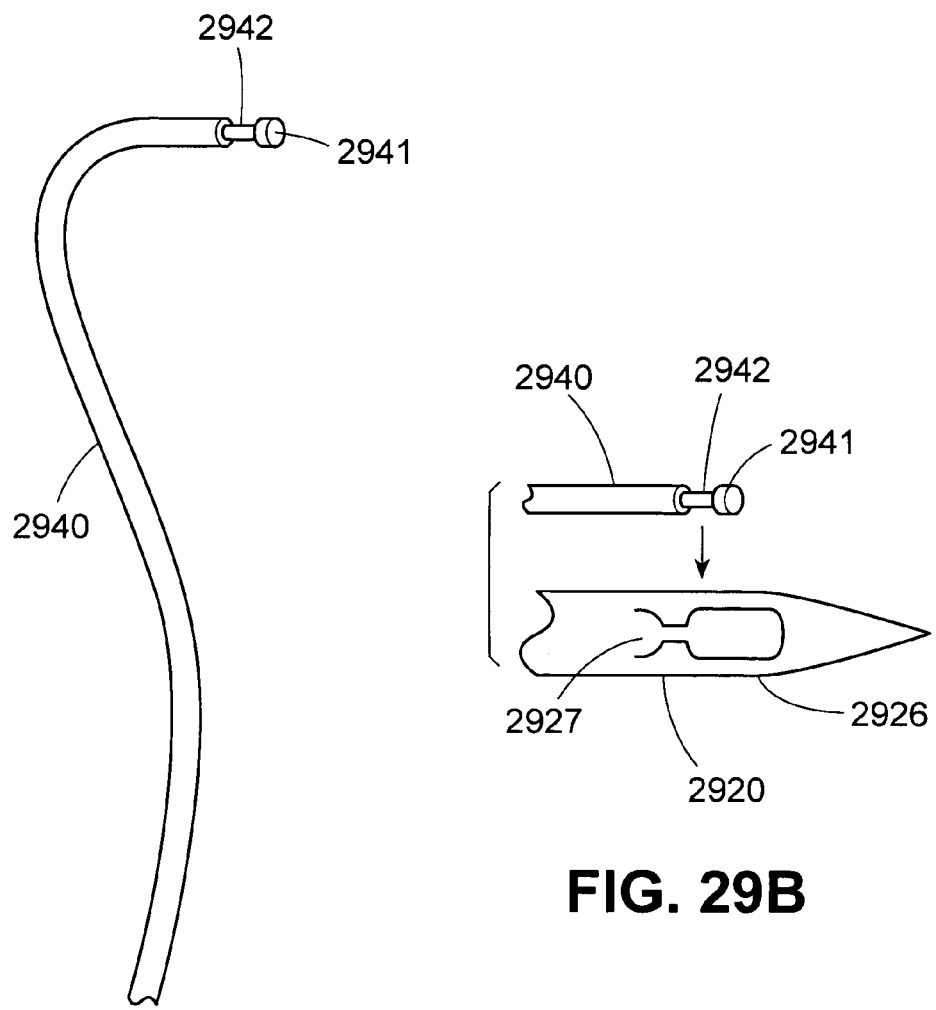
FIG. 29B
FIG. 29A
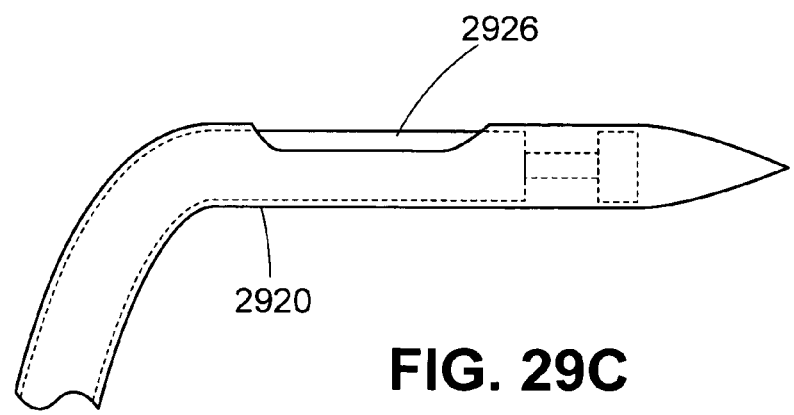
FIG. 29C

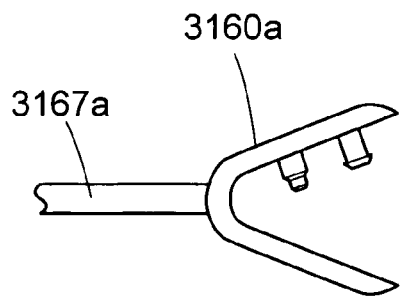
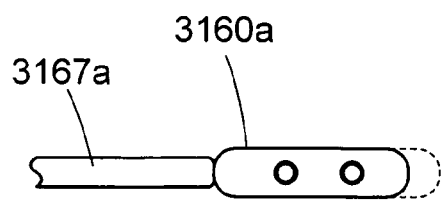
FIG. 31A        FIG. 31B
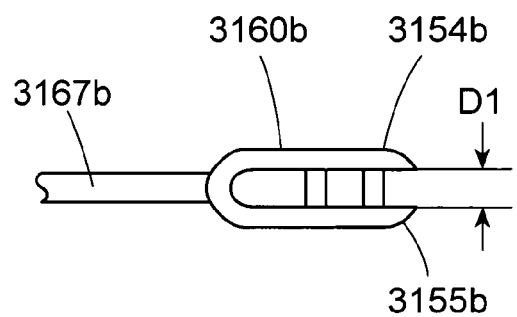
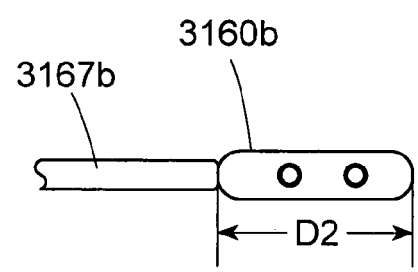
FIG. 31C        FIG. 31D
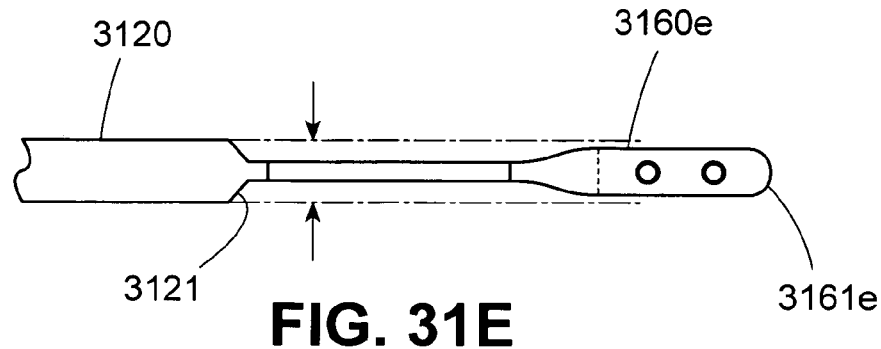
FIG. 31E

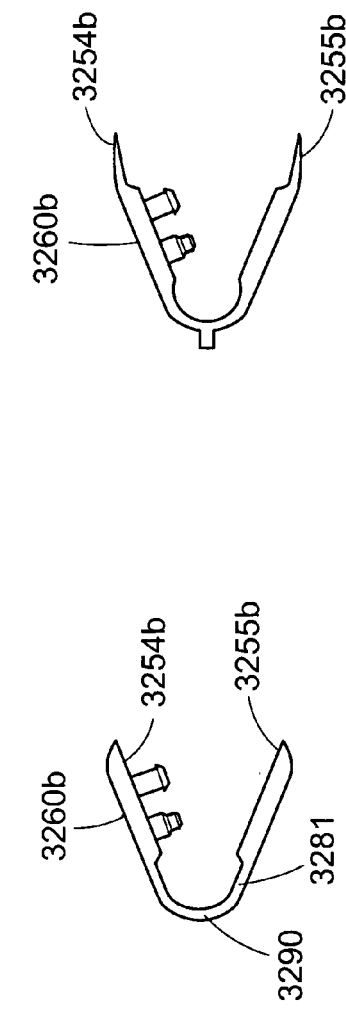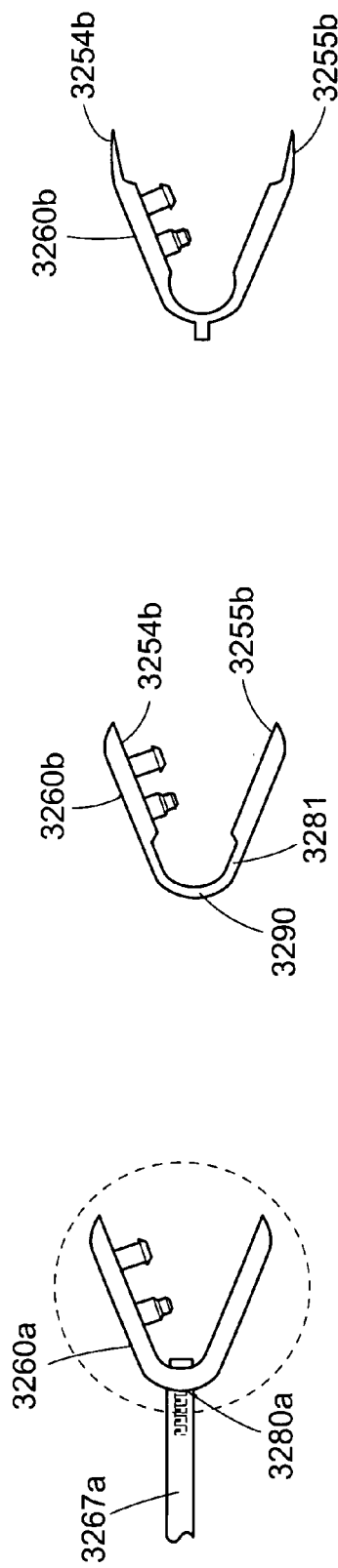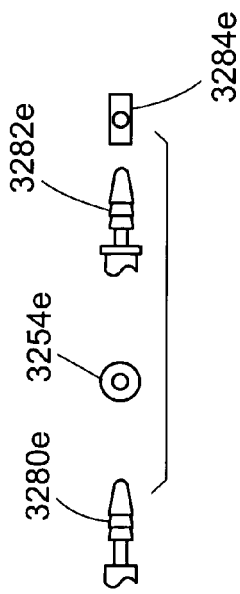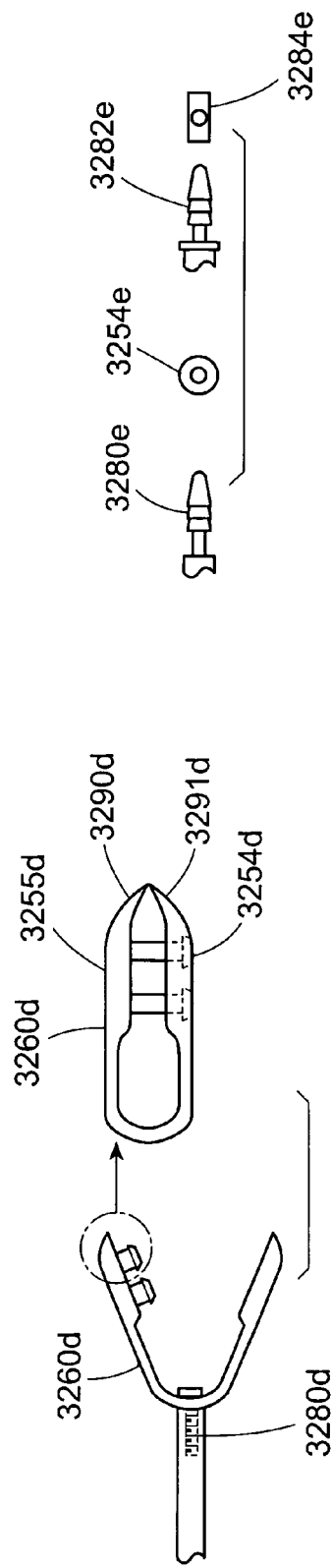

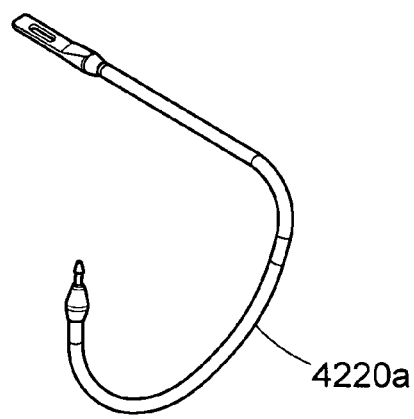
FIG. 42A
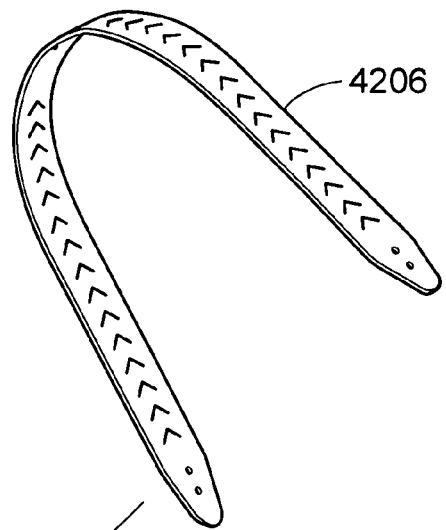
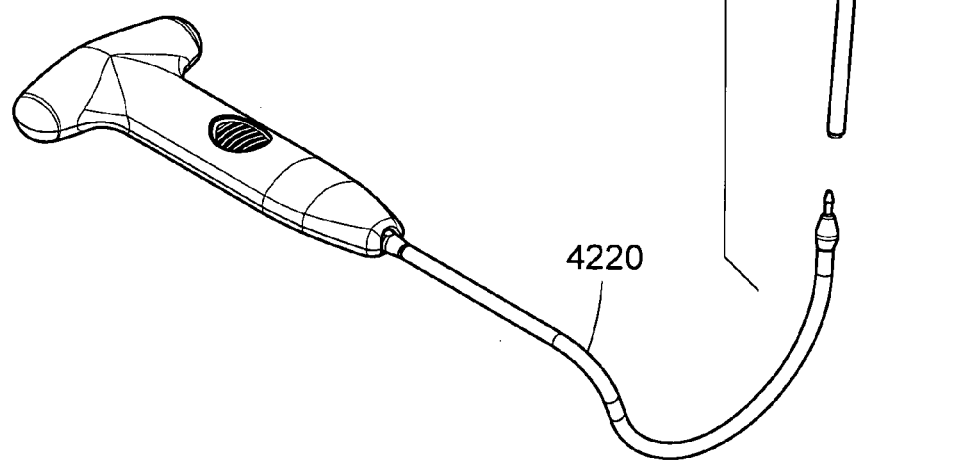
FIG. 42B

TRANSOBTURATOR INTRODUCER SYSTEM FOR SLING SUSPENSION SYSTEM

CROSS REFERENCE TO RELATED APPLICATIONS

This application is a continuation-in-part of, U.S. application Ser. No. 10/633,254 filed on Aug. 1, 2003, for SELF-ANCHORING AND INTRODUCER SYSTEM, which claims the benefit of U.S. Provisional Application No. 60/479,039 filed on Jun. 17, 2003 for EXPANDABLE TISSUE SLING AND METHOD OF FORMING THE SLING and U.S. Provisional Application No. 60/400,616, filed on Aug. 2, 2002, for NATURAL TISSUE SELF-ANCHORING SLING AND INTRODUCER SYSTEM, all of which are hereby incorporated herein by reference. This application also claims the benefit of U.S. Provisional Application No. 60/578,552, for SLING SUSPENSION SYSTEM filed on Jun. 9, 2004, which application is hereby incorporated by reference herein.

BACKGROUND OF THE INVENTION

An increasingly widespread technique for treating female urinary incontinence is that of sling suspension. Examples of such procedures and equipment which can be employed are discussed in U.S. Pat. Nos. 5,112,344, 5,899,909, and 6,273,852, the contents of which are incorporated herein by reference.

Generally, sling suspension procedures involve the placement of a sling member beneath the patient's urethra. The sling member is preferably implanted in the patient's tissue by using an introducer needle to help draw the tissue implant sling into position.

Slings have been made from tape or mesh. Numerous implant materials have been considered and used for sling procedures, including both synthetic and natural materials.

A traditional sling procedure involves placing a strip of an implant material (natural tissue or synthetic mesh) under the urethra and securing it to the rectus fascia or other portions of the patient's anatomy with sutures to hold the implant in position during the healing process.

Recently, improved techniques have been developed that speed the implant process, by reducing the number of incisions made and altering the pathways by which the tissue implant is introduced into the body. These improvements, which employ specialized instrumentation, help to reduce operative time and have made the procedure less invasive.

These techniques generally require that an implant be joined to an introducer needle. The implant is inserted into, and pulled through the body. Then, in a subsequent step, the implant is detached from the introducer needle. A deficiency with existing introducer devices, however, is that they are typically unwieldy, awkward and time consuming to attach and/or detach to an implant to or from an introducer device.

Another deficiency with existing introducer systems is that, in performing certain procedures, such as a transobturator needle inside-out approach in which the needle is first inserted and then passed through the obturator foramen, the use of existing introducer needles is commonly not practical because once in an earlier step, the tissue implant is passed through the obturator foramen, there is typically no practical method to position both ends of a tissue implant firmly in place under the bladder, because the introducer handle is typically, at that point, oriented on the wrong side of the introducer needle at that intermediate stage in the process. In addition, various proposed needle shapes make the procedure difficult, because of problems encountered when trying to predict the path the needle will take through the body.

Existing surgical hardware, such as the McGuire™ suture guide, which has a central suturing hole, and available from C.R. Bard, Inc. of Murray Hill, N.J., is based on what is known as the "Stamey" needle. Although such devices could be modified for use in the field of this invention, they do not possess all the requisite properties for the uses envisioned for this invention.

Thus, there exists a long-felt and unsolved need for a sling suspension introducer system which offers the distinct benefits of allowing tissue implants to be quickly and efficiently attached and detached to and from an introducer needle, and which allows for practical convenient insertion of an implant.

SUMMARY OF THE INVENTION

Generally speaking, in accordance with the invention, an implant system involving a needle connector and implant is provided to overcome disadvantages of existing systems. First, it should be understood that although this disclosure speaks of the sling suspension of the female urethra, this invention is not to be limited thereto. By way of non-limiting example, it has been determined that the devices and techniques described herein could be modified to support other body organs such as the bowel or bladder. Consequently, all portions of this description should be understood to encompass such alternative uses of this invention.

The invention is intended to provide an implant introducer system that can provide for selective attachment and detachment of implants to and from an introducer needle. It also describes selective attachment and detachment of an introducer needle to and from an introducer handle in a manner that can be an improvement over known systems.

The invention is directed to an introducer system comprising an introducer needle having a proximal end and a distal end. The needle can have a handle having a needle receiving end. The handle can be adapted to receive said distal end of said introducer needle such that said introducer needle is selectably detachably coupled to said handle.

Another aspect of the invention is directed to a connector for attachment to an implant strip. The strip can have an arm having a hole pre-formed therethrough. The introducer needle can include a connection portion having a barb. In one embodiment of the invention, the needle comprises a central portion. A first arm can be pivotally mounted to the central portion. It can have a first projection and a second projection extending therefrom. A second arm can be pivotally mounted to the central portion. It can have a first hole and a second hole defined therein. The first and second holes can be positioned so that when the first arm pivots toward the second arm, the first and second projections are received in the first and second holes. The introducer can include a tube portion extending from said central portion. It can define a tube aperture therein. The tube aperture can be adapted to receive the barb. The connector can be selectably detachably coupled to the introducer needle.

Still another aspect of the invention is directed to an introducer needle for attachment to an implant strip. The needle can comprise a needle body with first and second jaws. These can be located at a distal or proximal end of said needle body. The body can include an adjustment member. This can be located proximate said first and second jaws. It can be movable to at least a first position and a second position. The first and second jaws can be adapted to attach to the implant strip when the adjustment member is moved to a first position, and to release the implant strip when moved to a second position.

Another aspect of the invention is directed to a connector for attachment to an implant strip. The connector can have an arm having a hole therethrough. The introducer needle can include a connection portion having a barb. It can include a central portion and a first arm pivotally mounted to the central portion. It can have a first projection and a second projection extending therefrom. The first projection can have an engagement head. The head can be disposed at an end thereof. It can have a second arm. That arm can be pivotally mounted to the central portion. It can have a first hole and a recess defined therein. The first hole and the recess can be positioned so that when the first arm pivots toward the second arm, the first projection is received in the first hole. They can be positioned such that the engagement head engages the first hole. This can maintain the first and second arms in a closed position. The second projection can be received in the recess. A tube portion can extend from said central portion. It can define a tube aperture therein. The tube aperture can be adapted to receive the barb. It can receive the barb such that the connector can be selectably detachably coupled to the introducer needle.

In one embodiment of the present invention, an outside-in approach is performed in which the needle enters from the outside then after insertion pulls an end of the implant from the inside to the outside. This is then repeated on the other side of the body. This technique employs a detachable handle and a needle that can vary in shape. For example, it can have a horseshoe or helical shape that is curved at its distal end, the plane of such curved end being normal to a proximal portion of the needle.

Among the benefits of this invention is improved flexibility. A surgeon can use this system for a transobturator needle outside-in approach without the need to employ any additional special equipment.

In another embodiment of the invention, a connector tube is provided, in which one end of the connector tube contains a snapping mechanism and is stepped in such a way that an introducer needle can be and locked into place. In numerous embodiments, different materials with differing degrees of hardness can be used to help enable easier passage of the needle within the connector. For example, the connector tube can have an inner layer harder than or softer than an outer layer depending on the specific requirements of the embodiment.

In another embodiment of the invention, an introducer needle is provided, that is shaped in a horseshoe shaped halo design. This design can enable easier insertion of the implant within the body by allowing the doctor more visualization control of holding and navigating the needle.

In one embodiment of the invention, a needle tip is provided, in which the tip of the needle has a diameter that is smaller than the inner diameter of the connector that the needle is being inserted into but has a large enough diameter to be secured within the connector. Thus, once the needle is inserted, it locks into place within the connector, generating a tight fit.

In another embodiment of the invention, an introducer needle is provided that contains a threaded needle tip that can ease insertion of the needle by allowing the tip to be attached through a rotating movement.

In another embodiment of the invention, an introducer device is provided that contains an introducer needle, a handle and a tube connector that has a Y shaped end with two arms that interconnect with each other to hold an implant in place.

In another embodiment of the invention, a detachable introducer needle is provided that can be used to perform out an inside-out approach by inserting a tissue implant in such a manner that does not impede the removal of the needle once the implant has been inserted. The needle proceeds from the inside to the outside, the handle is removed and the proximal end of the handle is attached to the strip which is then drawn from the inside to the outside. Additionally in one embodiment, a textured tube connector can be used to enhance the gripping of the implant once it is inserted.

In another embodiment of the invention, a flexible filament is provided that has a rigid tip on one end with a connection portion and a generally y-shaped clamshell type connector on the other end. Additionally, an introducer needle is disclosed that comprises a channel shaped portion and has an open channel that is designed and dimensioned such that a flexible filament may be placed within the channel with the rigid tip of the flexible filament protruding out the distal end of the channel portion and the second end of the flexible filament extends out of the other side of shaped channel portion such that the connector is positioned to receive a tissue insert for insertion into a patient.

BRIEF DESCRIPTION OF THE DRAWINGS

In the drawing figures which are not necessarily drawn to scale, which are illustrative of various embodiments of the invention, and wherein like reference numerals denote similar elements throughout the several views:

FIG. 1A is a perspective view of an introducer comprising an introducer handle and an introducer needle having a barbed end;

FIG. 1B is a perspective view of an embodiment of a snap connector, which can be permanent, for coupling an implant strip to an introducer;

FIG. 1C is a perspective view of another embodiment of a snap connector, which can be permanent, having a coupling aperture for coupling with a barb on an introducer needle;

FIG. 3A is a perspective view of an embodiment of an introducer needle lying in a single plane;

FIG. 3B is a perspective view of another embodiment of an introducer needle;

FIG. 3C is a perspective view of another embodiment of an introducer needle;

FIG. 3D is a perspective view of another embodiment of an introducer needle;

FIG. 3E is a side elevational view of the introducer needle of FIG. 3D where it can be seen that the distal portion is in one plane and normal to the proximal shaft;

FIG. 3F is a top plan view of the introducer needle of FIG. 3D;

FIGS. 7A and 7B are embodiments of barbs of an introducer needle;

FIG. 10C is a plan view of another embodiment of a connector pin having thread barbs;

FIG. 10D is an enlarged view of one of the threads of FIG. 10C;

FIGS. 17A, 17B and 17C illustrate a needle inside-out approach to inserting an implant strip with an introducer needle in accordance with an embodiment of the invention;

FIGS. 18A, 18B, 19A, and 19B illustrate differences between embodiments of introducer needles for retropubic insertions versus introducer needles for transobturator insertions in accordance with embodiments of the invention;

FIG. 27A is a plan view of an flexible filament member, having a snap connector at a first end, and a rigid tip at a second end;

FIG. 27B is a perspective view of an introducer having an introducer handle and a tubular guard element having a slot for use with the filament member of FIG. 27A;

FIG. 27C is a perspective view of the flexible filament member of FIG. 27A inserted into the slot of the tubular guard element of FIG. 27B;

FIG. 28A is a perspective view of the flexible filament member and introducer having a tubular guard element of FIGS. 27A, 27B and 27C;

FIGS. 28B and 28C are cross sectional views of two embodiments of the tubular guard element and flexible filament member of FIG. 28A;

FIG. 29A is a perspective view of a flexible filament member having a connector member at an end thereof;

FIG. 29B is a perspective view of a portion of the flexible filament member and connector member of FIG. 29A and a portion of an introducer needle having a recess to receive the connector member;

FIG. 29C is a perspective view of the introducer needle of FIG. 29B with the introducer filament member of FIG. 29A positioned within the introducer needle;

FIGS. 31A and 31B are side elevational and top plan views, respectively, of an embodiment of an introducer connecting tube and a snap connector for coupling to an insertions strip;

FIGS. 31C and 31D are side elevational and top plan views, respectively, of another embodiment of an introducer tube extension and a connector for coupling to an insertions strip;

FIG. 31E is a top plan views an embodiment of an introducer tube extension and a connector having a tapered side;

FIGS. 32A, 32B, 32C, and 32D show different embodiments of a snap connector for coupling to an implant strip;

FIG. 32E shows side and front elevational views of embodiments of pin connectors for connecting snap connectors to an introducer needle;

FIG. 42A shows a halo shaped needle assembly;

FIG. 42B shows a halo shaped needle assembly with a connector and tissue implant plus a second needle for the other side of the patient;

DETAILED DESCRIPTION OF THE PREFERRED EMBODIMENTS

Figure 2A:
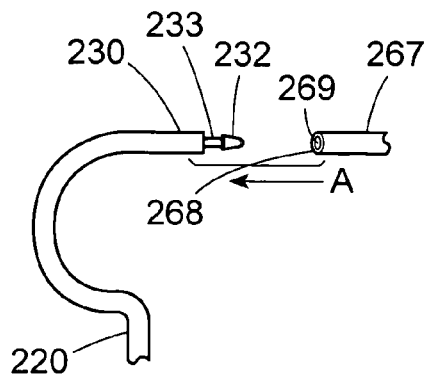
FIG. 2A is a perspective view of an embodiment of an introducer needle having a barb and a snap connector having a coupling aperture.

Referring now to the drawings, the various preferred embodiments of the present invention will be discussed in detail.

As depicted in FIG. 1A an introducer device 10 is shown in accordance with an embodiment of the invention. As is discussed in further detail below, introducer device 10 may be used to introduce an implant strip, such as, for example, a tissue implant, into a patient. Introducer device 10 comprises an introducer handle 12 which is shown attached to an introducer needle 20. Introducer needle 20 may be permanently attached to introducer handle 12 or, as is discussed in further detail below, introducer needle 20 can be selectively detachably connected to introducer handle 12. Introducer needle 20 can have a curved portion 23, and, located at a proximal end 30 of introducer needle 20, a shaft portion 33 and a barb 32. As will be discussed in further detail below, curved portion 23 of introducer needle 20 allows a doctor to insert an implant strip or tissue implant into the patient while navigating around and through various organs and/or other structures within the body of the patient, such as the obturator.

To secure a tissue implant or support strip to introducer needle 20, a connector may be used. With reference to FIG. 1B, there is shown an embodiment of a generally t-shaped tissue connector 50. Tissue connector 50 has a proximal needle side 52 and a distal tissue implant side 53. Needle side 52 is designed for connecting to an introducer needle and tissue side 53 is designed for connection to a tissue implant. On tissue side 53, arms 54B and 55B are designed to pivot from center portion 51 by way of, for example, a living hinge. Projections 56 and 56a may be inserted into holes 58 and 58a such that arms 54B and 55B may be positioned and held together, or maintained in a closed position, while securing a tissue implant having coupling apertures positioned to receive projections 56, as is described in further detail below. Needle side 52 and connector 50 is substantially a mirror image of tissue side 53, with arms 54a and 55a having projections 56b and 56c and holes 58b and 58c for insertion into each other when maintained in a closed position. Arms 54a and 55a may be closed by moving them about central portion 51 in a resilient matter. Tissue connector 50 is designed to be coupled with an introducer needle having coupling holes oriented and positioned such that projections 56 can pass through the coupling holes (not shown).

With reference to FIG. 1C, there is shown another embodiment of a generally y-shaped tissue connector 60 in accordance with another embodiment of the invention. A tissue implant side 63 of connector 60 is similar to that of tissue side 53 of connector 50. A pair of arms 64 and 65 may be coupled to a tissue implant strip as projections 66 and 66*a* and may be inserted through coupling holes in a tissue implant and into a pair of corresponding holes 68 and 68*a*, locking arms 64 and 65 in position, and thereby securing a tissue implant to connector 60. Needle side 62 of connector 60 is formed with a tube portion 67 extending outward and having a tube aperture 69 defined in a tube end 68.

Tissue connector 60 may be quickly and easily attached or coupled to introducer needle 20 by pushing or aligning tube aperture 69 over barb 32 such that barb 32 extends into tube end 68 of tube aperture 69. As is described in further detail below, connector 60 may be quickly and easily removed from introducer needle 20 by pulling connector 60 off of and away from the end of introducer needle 20 such that barb 32 is removed from tube aperture 69. Alternatively, the tissue connector 60 may be permanent and not easily detachable.

A benefit of such a design, whereby a tissue connector 60 may be quickly and easily attached to introducer needle 20 or removed therefrom, is that it facilitates easy placement or attachment of the tissue implant to the needle and thus speeds up the implanting procedure as will be described in further detail below.

With reference to FIG. 2A, there is shown tube portion 267 of connector 60 being moved in a direction A, such that barb 232 and shaft 233 of introducer needle 220 that are connected at point 230 will protrude into tube aperture 269 of connector 60 such that connector 60 may be quickly and easily joined to introducer needle 220. Connector 60 may also be removed from introducer needle 220 by pulling connector 60 in a direction opposite to direction A thus removing barb 232 and shaft 233 of introducer needle 220 from the connection point 268 of tube aperture 269 of tube portion 267 of connector 60. Tube aperture 269 can be formed as a generally undifferentiated cylinder, having a single internal surface for resiliently gripping barb 232.

Figure 2B:
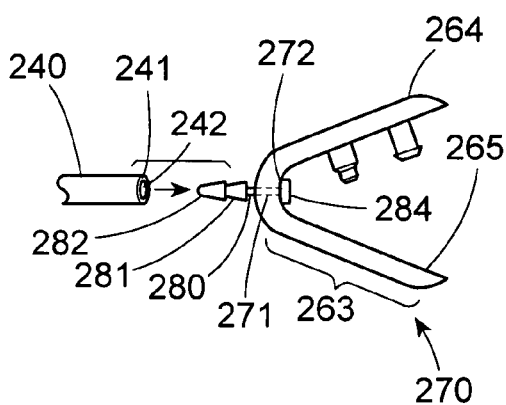
FIG. 2B is a perspective view of a portion of an introducer needle having a coupling aperture and a snap connector having a barb.

In an alternate embodiment, as illustrated in FIG. 2B, introducer needle 220 may be formed with a needle tube 240 having a needle tube aperture 242 defined in a needle tube end 241. A connector 270 may be coupled to introducer needle 220 by way of a connector pin 280. Connector pin 280 may be passed through aperture 271 of connector 270 which contains a distal tissue side 263 and a pair of arms 264 and 265. A pair of pin barbs 281 and 282 may be inserted into a needle tube aperture 242 to secure connector 270 to introducer needle 220. A pinhead 284 may be shaped and designed such that it presses against a surrounding surface 272 defining aperture 271 and connector 270, thus securing connector 270 to introducer needle 220. As will be discussed in further detail below, embodiments of connector pin 280 in accordance with the invention may have one or more barbs 281 which may be designed and shaped in various configurations.

Figure 2C:
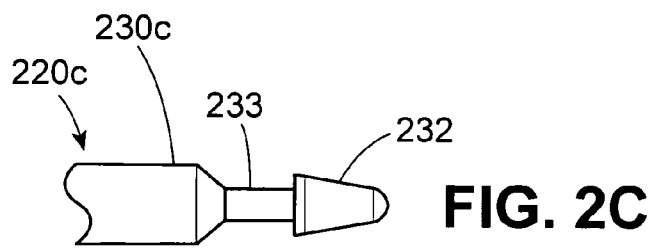
FIG. 2C is a plan view of a portion of an embodiment of an introducer needle having a single barb design.
Figure 2D:
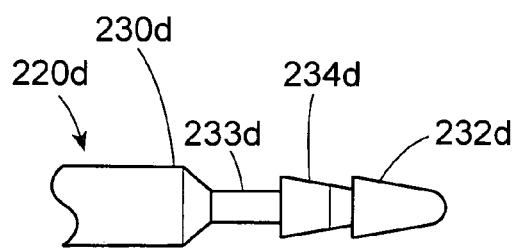
FIG. 2D is a plan view of a portion of an embodiment of an introducer needle having a dual barb design.
Figure 2E:
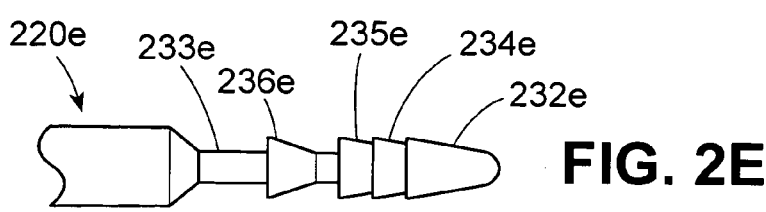
FIG. 2E is a plan view of a portion of an embodiment of an introducer needle having a multi-barb design.

Similarly, with respect to FIG. 2A, introducer needle 220 may be designed with one or more barbs 232 in various configurations at shaft 33. FIGS. 2C, 2D and 2E illustrate several embodiments of an introducer needle 220, 220*c*, 220*d*, and 220*e* having different configurations of barbs. FIG. 2C illustrates a design wherein introducer needle 220*c* has an introducer needle proximal end 230*c* having a single barb 232*c* at shaft 233*c*. With reference to FIG. 2D, introducer needle 220*d* is shown having at proximal end 230*d* having two barbs 232*d* and 234*d* at shaft 233*d*. Introducer needle 220*e* shown in FIG. 2E has three barbs 232*e*, 234*e*, 235*e* plus an additional barb 236*e* at adjacent shaft portion 233.

Different configurations of barb designs at the proximal end of the introducer needle as illustrated in, for example, FIGS. 2C, 2D and 2E, may facilitate different degrees of connection or holding force to maintain connector 60 in a coupled state with the introducer needle as desired depending on the circumstances of a particular procedure or operation to be performed.

With reference to FIG. 3A, an introducer needle 320*a* may be formed with barb 332 at one end and needle handle pin 324 at needle proximal end 322 such that introducer needle 320*a* may be selectably removably detachable to introducer handle 12. By designing introducer needle 320*a* such that it is selectably detachably removable from introducer handle 12, introducer needles of various shapes and configurations, as may be required for different procedures or different portions of certain procedures or operations, may be attached or removed from introducer handle 12 as needed.

With reference to FIGS. 3B, 3C, 3D, 3E and 3F, there are shown several embodiments of various introducer needle geometries (needles 320*b*, 320*c*, 320*d*) which may be beneficially used in different procedures or different portions of a single procedure to facilitate a successful procedure. FIG. 3B illustrates an introducer needle 320*b* having a hook shape wherein the hooked portion lies substantially in a single plane (2-D design). FIG. 3C shows an introducer needle 320*c* having a helical shape (3-D design). FIG. 3D shows an introducer needle 320*d* having a 90 degree 2-D hook shape, with the hook residing in one plane. Side and top views of introducer needle 320*d* are shown in FIGS. 3E and 3F respectively. Because the curved distal end of needle 320*d* is in a single place at a right angle to the needle shaft, a twist of the wrist can drive the needle in a distal direction and the exit point can be easily visualized. Accordingly, by use of a selectably detachable introducer needle, various shapes and configurations of needles may be selectably attached to, detached from, and used with the same introducer handle 12. The ability to switch needles also provides additional benefits during different portions of a procedure, as is discussed in further detail below.

Figure 4:
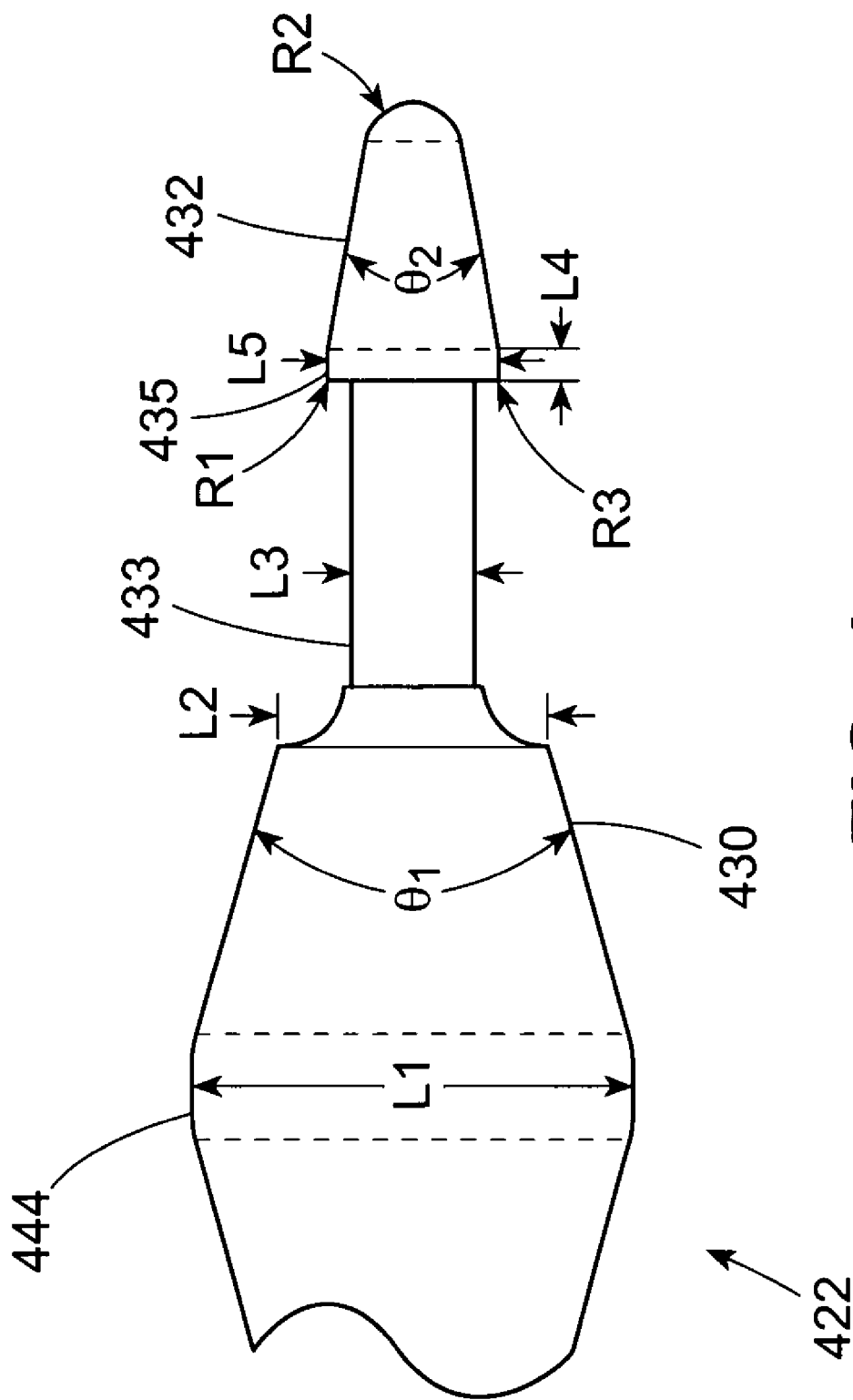
FIG. 4 is a plan view of a portion of an introducer needle having a barb tip.

In other embodiments of the invention, certain dimensions for the configuration of the introducer needle have been found to be beneficial. With reference to FIG. 4, there is shown a needle distal end 430, having certain beneficial dimensions. Tapered portion 422, in this embodiment has a large diameter L1 of about 0.210 inches (0.180-0.225 preferred) and an angle $\theta_1$ of about 30 degrees (about 25 to 40 preferred). A flat portion 444 has a thickness L2 of 0.105 inches (0.080 to 0.12 preferred) while a shaft portion 433 has a thickness L3 of 0.065 inches (0.05 to 0.08 preferred). A barb 432 had a maximum thickness L5 of 0.086 inches (0.07 to 0.1 preferred) and a flat portion 435 with a width L4 of 0.102 inches (0.08 to 0.125 preferred). The front of barb 432 has a radius R2 of 0.024 inches (0.15 to 0.33 preferred) and forms an angle $\theta_2$ of 20 degrees (about 15° to 25° preferred). A radius R3 at the corner of flat portion 435 is 0.002 inches (0.001 to 0.003 preferred). While specific dimensions of needle proximal end 430 of introducer needle 20 are preferred and facilitate proper working of the device, other dimensions may be used as a matter of application specific design choice as applied by one skilled in the art as instructed by the teachings herein. The dimensions herein are generally applicable to similar structures of other embodiments of the invention.

Figure 5:
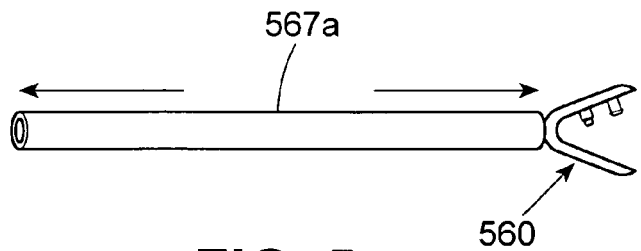
FIG. 5 is a plan view of an embodiment of a snap connector.

With reference to FIG. 5 of the invention, a connector 560 may be attached or coupled to a tube extension 567a. Tube extension 567a may facilitate the coupling of connector 60 to an introducer needle during certain procedures. It can be flexible, which can facilitate its travel through the body. In one embodiment of the invention, it is about as long or longer than the curved distal portion of the needle, sized so that its proximal end can be retracted from the body before it passes the implant therethrough.

Figure 6A:
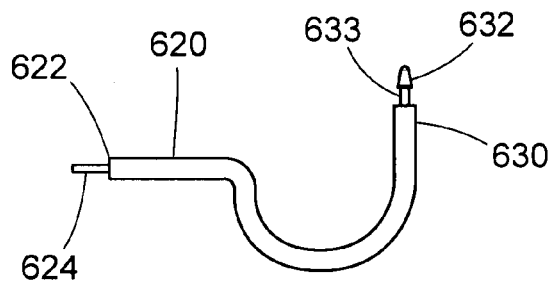
FIG. 6A is a plan view of an embodiment of an introducer needle having a barb.
Figure 6B:
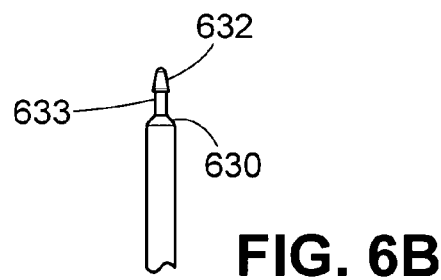
FIGS. 6B, 6C and 6D are embodiments of barbs for the introducer needle of FIG. 6A.
Figure 6C:
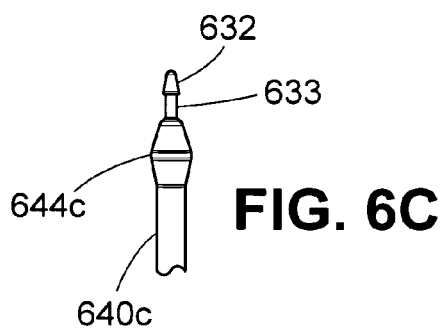
Figure 6D:
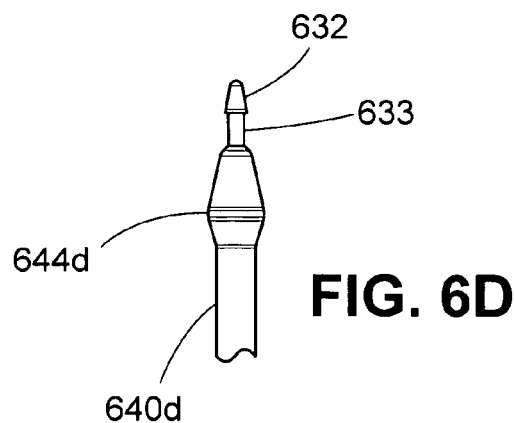

With reference to FIGS. 6A, 6B, 6C and 6D, embodiments of the barb and needle distal end of the introducer needle may have different shapes and/or configurations. With reference to FIG. 6B, a straight tip design is shown wherein a barb 632b and a shaft portion 633b are attached to a needle distal end 630b of the needle 620, which is relatively narrow. With reference to FIG. 6C, a dilating tip design is shown wherein a flared portion 644c is shown at a needle tube 640c. Flared portion 644c serves to protect the proximal surface of tube 567a at the junction with bars 632b as the needle is passed through the body of a patient. Thus, less stress is placed on connection 560, which is less likely to be pulled off. In another embodiment, flared portion 644d as shown in FIG. 6D, is larger than that of flared portion 644c in FIG. 6C. Flared portion 644d thus provides a greater level of protection than does flared portion 644b.

With reference to FIG. 7A, and FIG. 7B, an embodiment of a dilating needle tip 700 is shown. FIG. 7A shows needle tip 700 itself while FIG. 7B shows needle tip 700 along with a needle shaft 730. A flared portion 744c has a larger diameter than the body of needle shaft 730, thus helping to protect the connector from being pulled off. The diameter of the needle tip 742c is shown as smaller that the diameter of the flared portion 744C.

Figure 8:
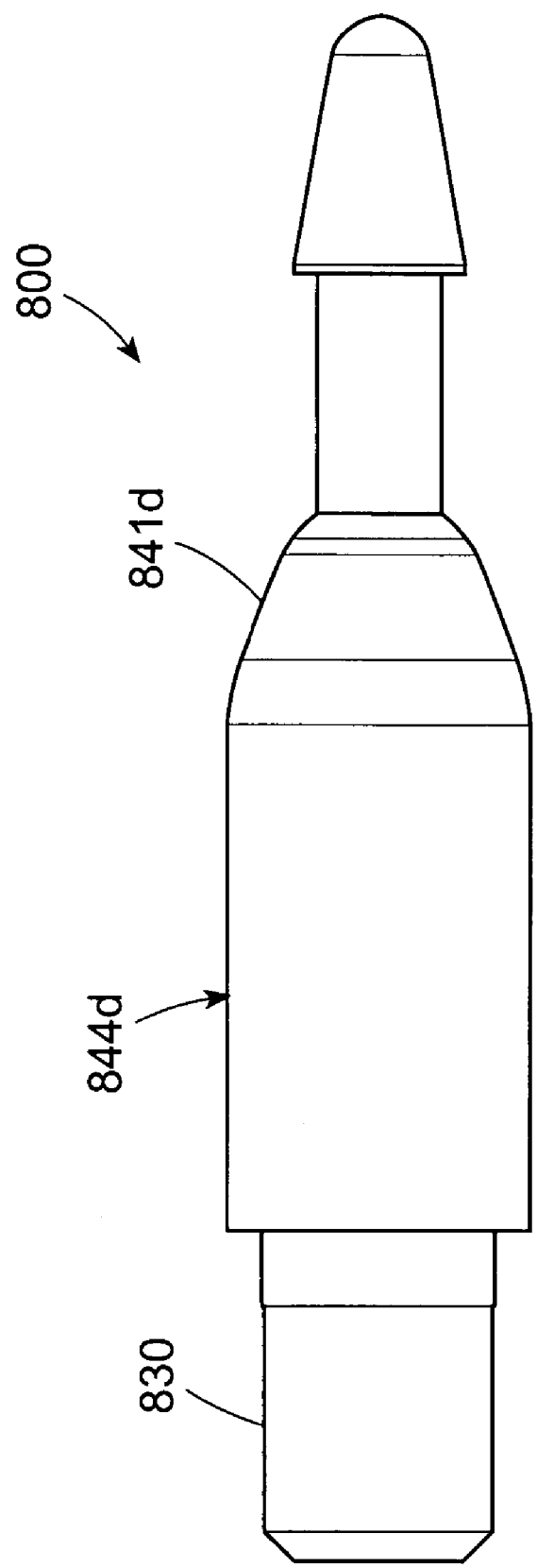
FIG. 8 is another embodiment of a barb of an introducer needle.

With reference to FIG. 8, straight tip introducer needle 800 is shown. A flared portion 844d is shown having essentially the same diameter as that of the needle shaft 830 of the introducer needle. In one embodiment the diameter represented by 844d is 0.156 inches (0.14 to 0.17 is preferred).

Figure 9A:
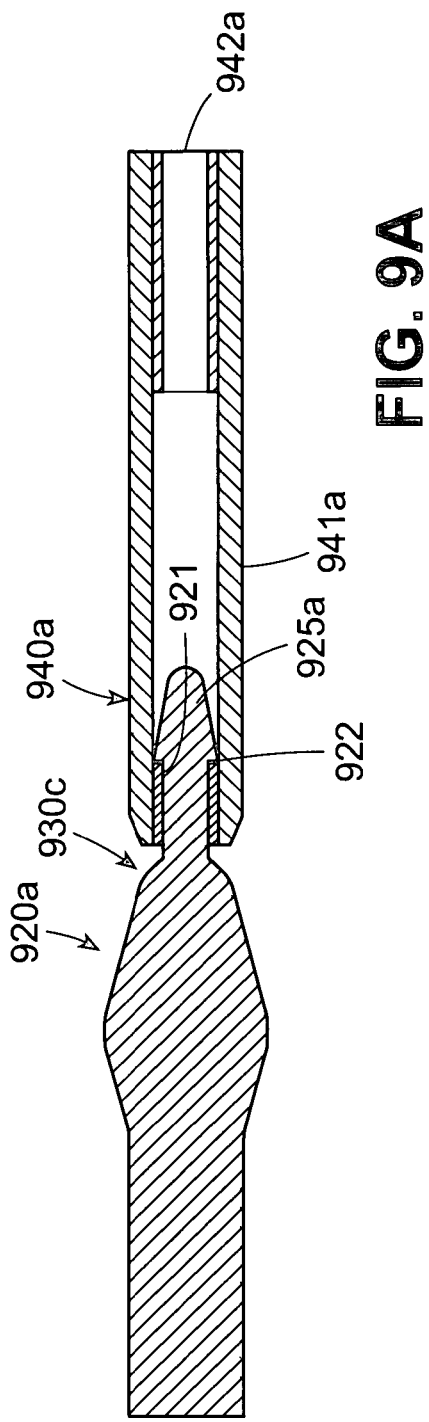
FIG. 9A is a plan view of an embodiment of an introducer needle having a barb and a snap connector wherein the introducer needle is wider than the tube extension of the snap connector.

An introducer needle 920a of FIG. 9A shows a stepped-tube connection with needle tip 930a and stepped tube 940a which has an outer uniform diameter layer 941a and an inner layer 942a separated in the presented embodiment by ½". This dual layer creates a step that allows secure attachment to the needle tip 930a between a single annular surface 921 of barb 925a with inner tube 940a angular surface 922. The outer layer is made of a softer material, for example a hardness of 55 on a shore D scale to permit optimal flexibility, while the inner core layer comprises a stronger material, for example a hardness of 70 (65 to 75 preferred) on a shore D scale to maximize tensile strength with minimal compromise to the flexibility. While these hardness values are preferred, other hardness values may be used as a matter of application specific design choice as applied by one skilled in the art as instructed by the teachings herein.

Figure 9B:
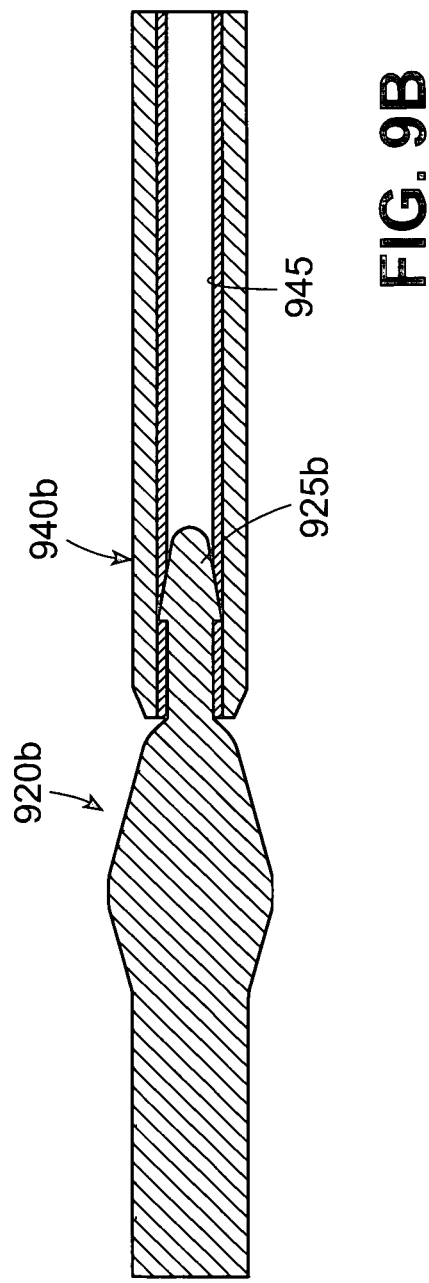
FIG. 9B is a plan view of an embodiment of an introducer needle having a barb and a snap connector wherein the introducer needle is the same width as the tube extension of the snap connector.

An alternate embodiment shown in FIG. 9B which similar to the embodiment shown in FIG. 9A has a dual layer but in FIG. 9B, the tube 940b, however has a uniform cross sectional design and is not stepped. Rather a single inner undifferentiated surface 945 is provided. In this embodiment, the tube 940b attaches to the needle 920b by deformation and radial compression of surface 945 around barb 925b.

Figure 10B:
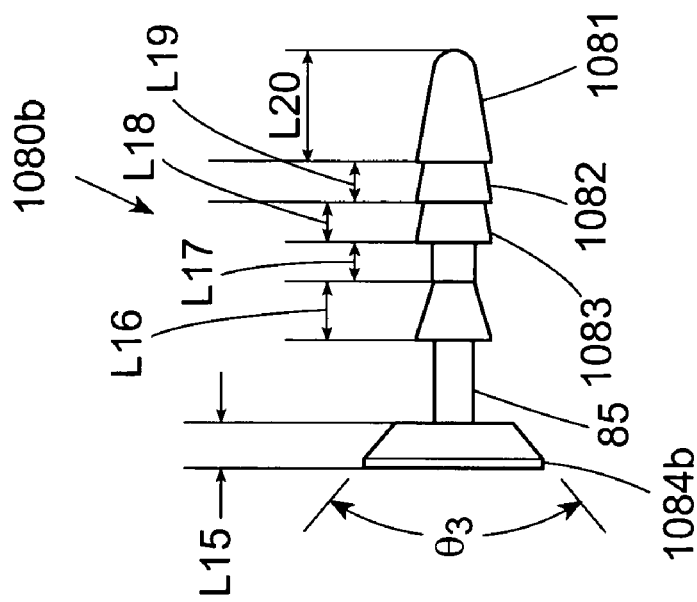
FIG. 10B is a plan view of another embodiment of a connector pin having multiple barbs.
Figure 10A:
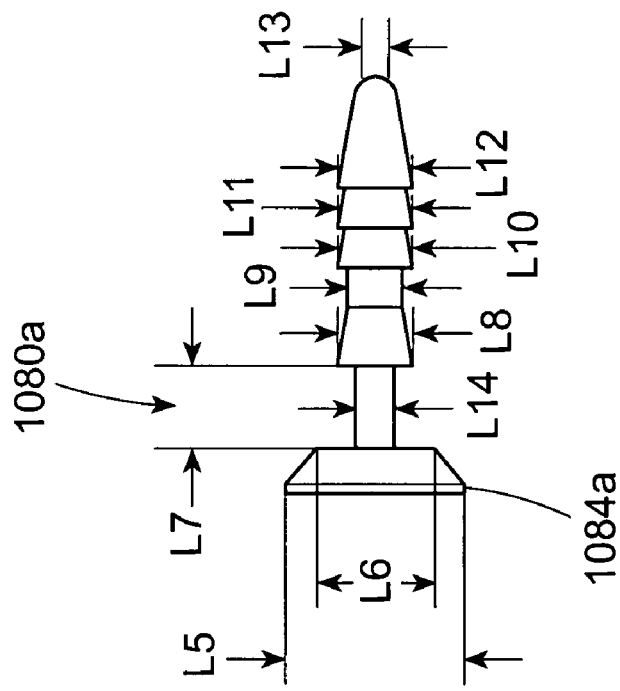
FIG. 10A is a plan view of an embodiment of a connector pin having multiple barbs.

FIGS. 10A and 10B illustrate embodiments of a connector pin for securing a connector 60 to tube extension 67a. While the connector pin may have various dimensions, in certain embodiments, certain dimensions have been found to facilitate beneficial use of the connector pin.

With reference to FIG. 10A, an embodiment of a pinhead 1084a of a connector pin 1080a is designed with a width L5 of 0.133 inches (0.13 to 0.15 preferred) and inner side width L6 of 0.112 inches (0.110 to 0.13 preferred). Length L7 of the shaft is dimensioned at 0.051 inches (0.045 to 0.060 preferred) while barb width L8 is dimensioned to be 0.082 inches (0.070 to 0.095 preferred) and barb at shaft width L9 is dimensioned to be 0.060 inches (0.050 to 0.070 preferred). Barb width L10 is dimensioned to be 0.067 inches (0.055 to 0.075 preferred) while barb width L11 and L12 were dimensioned to be 0.060 inches (0.055 to 0.070 preferred) with barb front width L13 being 0.035 inches (0.025 to 0.045 preferred). With reference to FIG. 10B, a pinhead 1084b of a pin connector 1080b was dimensioned with angle $\theta_3$ of 41 degrees with pinhead 1084b having a thickness L15 of 0.045 inches and a shaft 1085 having a length L16 of 0.098 inches (0.090 to 0.105 preferred). Shaft length L17 is dimensioned with a length of 0.049 inches while a barb 1083 is dimensioned with a length L18 of 0.044 inches (0.035 to 0.060 preferred), a barb 1082 is dimensioned with a length L19 of 0.047 inches (0.038 to 0.060 preferred) and a barb 1081 is dimensioned with a length L20 of 0.050 inches (0.040 to 0.060 preferred). Accordingly, while these dimensions were found to be preferred, a pin connector 1080a and 1080b in accordance with the invention can be designed with differing dimensions as a matter of application specific design choice as determined by one skilled in the art, as instructed by the teachings herein.

With reference to FIGS. 10C and 10D, in an alternative embodiment, a pin 1080c can also be designed with threads 1086c. In one embodiment, the angle $\theta_5$ of the point of pin 1080c is dimensioned to be 60 degrees (about 50-70 preferred). Shaft length L22 is dimensioned to be 0.252 inches (0.200 to 0.280 preferred) while threads length L23 is dimensioned with a pitch of 0.038 inches (0.0370 to 0.0395 preferred). A head 1084c is dimensioned with a width L25 of 0.135 inches (0.125 to 0.140 preferred) and forming an angle $\theta_4$ of 87 degrees. With reference to FIG. 10D, one of the threads 1086d of pin 1080c is shown having a thickness L26 of 0.024 inches (0.018 to 0.035 preferred) and forming angle $\theta_6$ with the shaft of 131 degrees (125 to 135 preferred) and angle $\theta_7$ of 132 degrees (126 to 136 preferred). While the above-listed dimensions were found to be beneficial, other dimensions can be used as would be determined as a matter of application specific design choice as determined by one skilled in the art as instructed by the teachings herein.

Figure 11A:
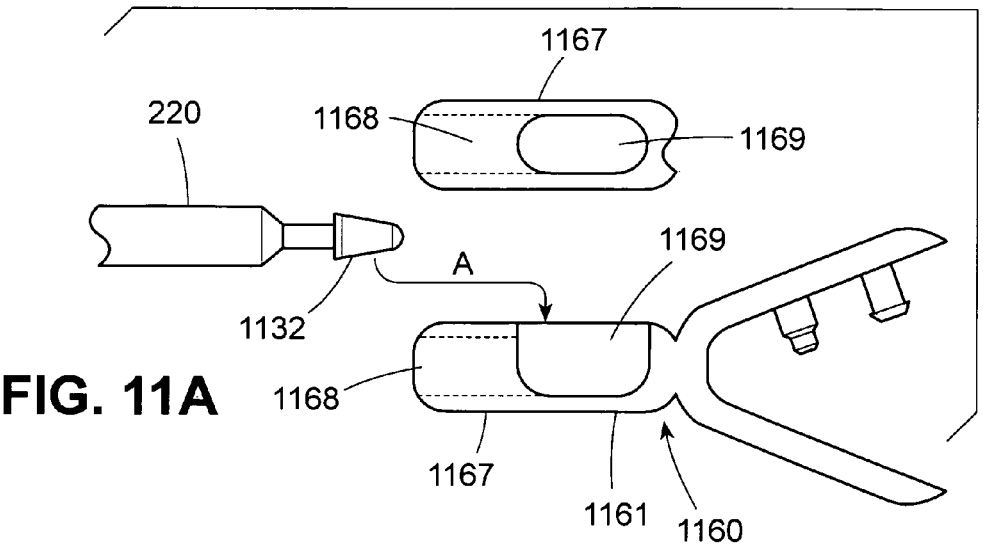
FIGS. 11A, 11B, 11C and 11D illustrate an embodiment of an introducer needle and snap connector designed to be coupled via a slot connection.
Figure 11B:
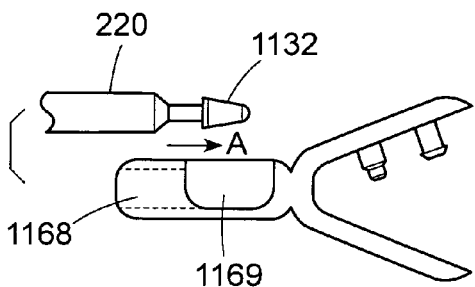
Figure 11C:
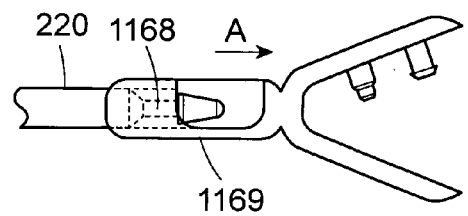
Figure 11D:
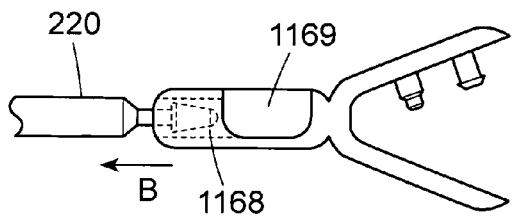

With reference to FIGS. 11A, 11B, 11C and 11D, there is shown a connector 1160 that can be selectably detachable to an introducer needle 220 and used to couple needle 220 to an implant strip. Connector 1160 is shown having a connector opening 1169 and a connector channel 1168 formed in connector tube 1167. As is shown in FIGS. 11B, 11C and 11D, needle barb 1132 of introducer needle 220 may be aligned with and moved in direction A into connector opening 1169. Introducer needle 220 may then be pulled back in direction B such that needle barb 1132 snaps into place in connector channel 1168. In this manner, connector 1160 may be coupled to introducer needle 220. In an alternate embodiment, channel 1168 can be modified to extend open to the proximal end of connector 1160 so that needle barb 1132 is dropped into the slot, then in an optional embodiment, pulled back in a direction opposite arrow A.

Figure 12B:
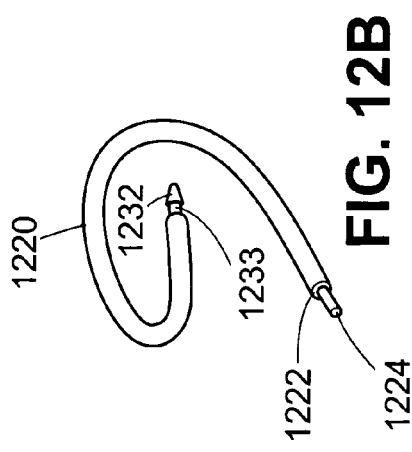
FIG. 12B is a partial plan view of an introducer handle and an introducer needle designed to be coupled via a barb and aperture connection.
Figure 12C:
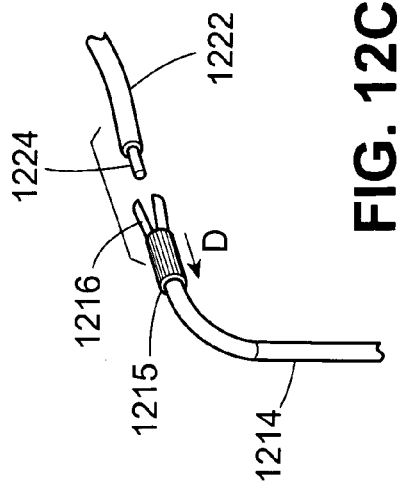
FIG. 12C is a partial plan view of an introducer handle and an introducer needle designed to be coupled via a spring lock connection.
Figure 12A:
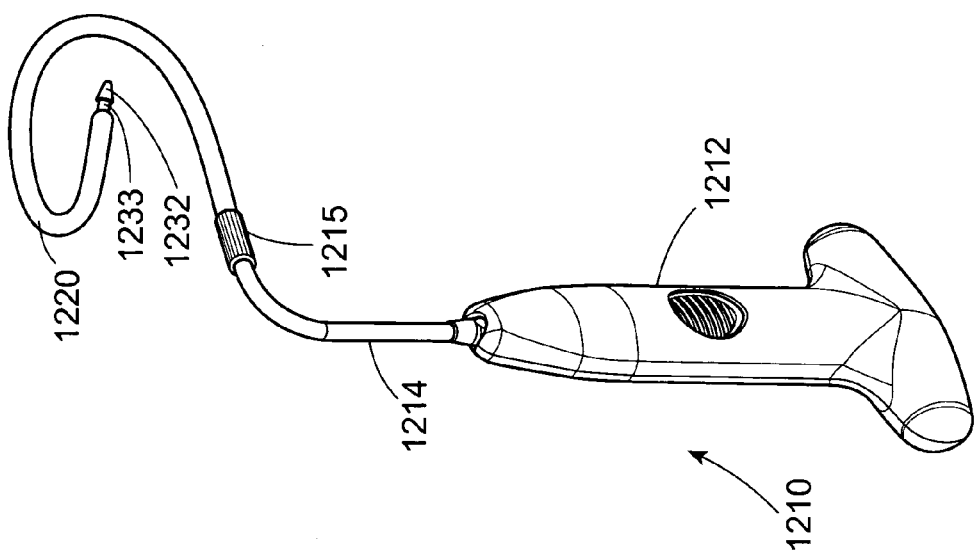
FIG. 12A is a plan view of an introducer handle and an introducer needle coupled via a screw connection.

With reference to FIGS. 12A, 12B and 12C, there is shown an introducer device 1210. Introducer device 1210 comprises an introducer handle 1212 connected to a handle extension shaft 1214. Extension shaft 1214 includes a collet 1215 which may apply pressure to a plurality of fingers 1216 (FIG. 12C) when threaded over internal threads on extension piece 1214 (not shown). In the operation of introducer device 1210, introducer needle 1220 is selectively detachable, but instead of a press or push fit, as described above with respect to certain embodiments, in this embodiment, a needle proximal end 1222 of introducer needle 1220 is moved in direction D and positioned such that a barb 1224 becomes positioned between fingers 1216 of extension piece 1214. Once barb 1224 is positioned within fingers 1216, collet 1215 is rotated such that fingers 1216 press upon barb 1224, and introducer needle 1220 is selectively attached to handle extension shaft 1214. By rotating collet 1215 in the opposite direction, fingers 1216 can be separated and introducer needle 1220 can be removed. Alternatively, instead of a rotating motion, collet 1215 can be operated via a sliding movement sliding toward fingers 1216 to compress them and secure introducing needle 1220, and alternatively sliding collet 1215 away from fingers 1216, thus allowing fingers 1216 to separate and releasing introducer needle 1220.

Figure 13A:
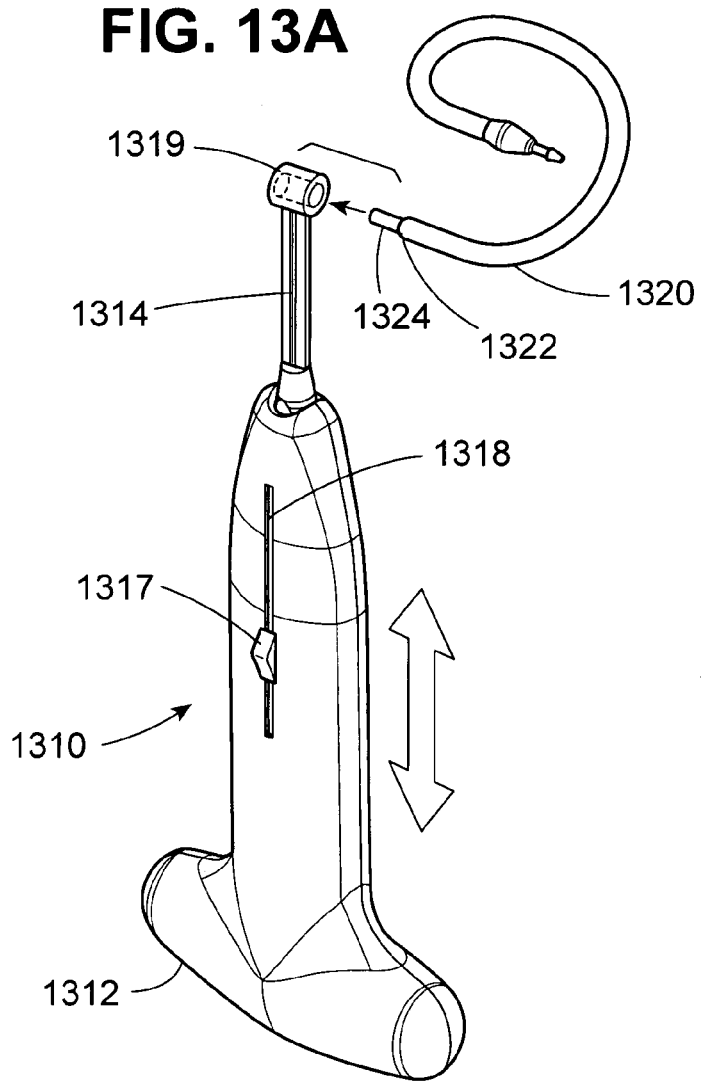
FIGS. 13A, 13B and 13C show various embodiments of an introducer handle having an actuator assembly for coupling the introducer handle to an introducer needle.
Figure 13B:
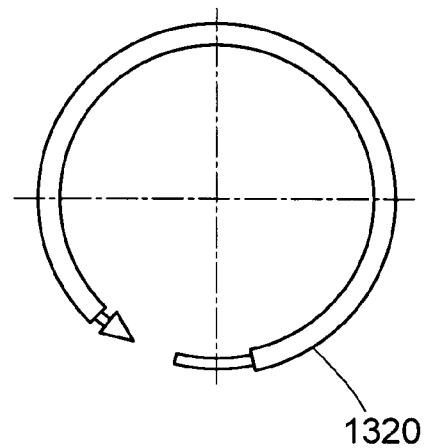
Figure 13C:
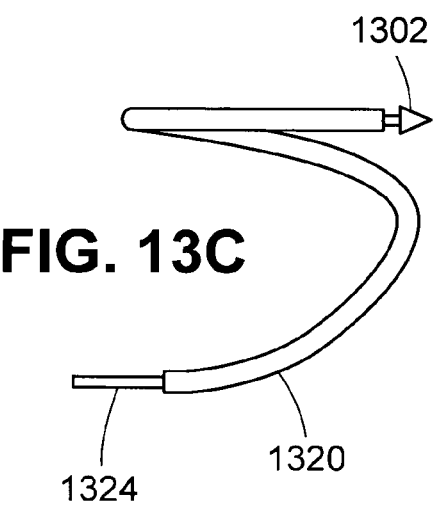

In yet another embodiment of the invention, an introducer device, with reference to FIGS. 13A, 13B and 13C, introducer device 1310 is shown. Introducer device 1310 includes introducer handle 1312 which contains a handle actuator 1317 which actuates an internal actuating device 1318. A handle extension 1314 contains an extension aperture 1319. Introducer needle 1320 is moved toward extension aperture 1319 and extension portion 1324 of introducer device 1320 is inserted into extension aperture 1319. Handle actuator 1317 is then moved toward introducer device 1320 causing a compression piece (not shown) within extension aperture 1319 to apply pressure to extension piece 1324, thus securing introducer needle 1320 to introducer device 1310. Handle actuator 1317 may be moved away from introducer needle 1320, thus releasing retention pressure against extension piece 1324 and allowing introducer needle 1322 to be removed.

With reference to FIGS. 13B and 13C, introducer needle 1320, being detachable, provides beneficial results when it is formed in a substantially continuous arc shaped geometry as is depicted in a top view (FIG. 13B) and a side view (FIG. 13C), with minimal straight portions of introducer needle 1320 being part of the composite shape of the piece. Such a shape allows for smooth and continuous insertion of a tissue implant into the body during an insertion procedure.

Figure 14A:
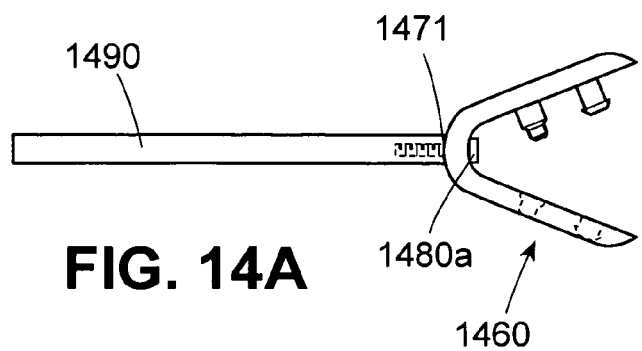
FIG. 14A is a plan view of an embodiment of a tube extension coupled to a snap connector via a connector pin.
Figure 14B:
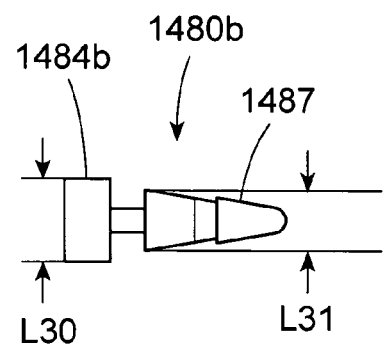
FIG. 14B is a plan view of an embodiment of a connector pin having a barbed portion.
Figure 14C:
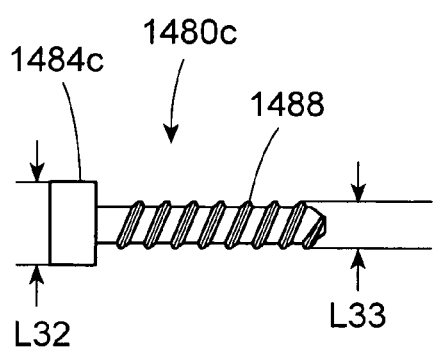
FIG. 14C is a plan view of an embodiment of a connector pin having a scalloped portion.
Figure 14D:
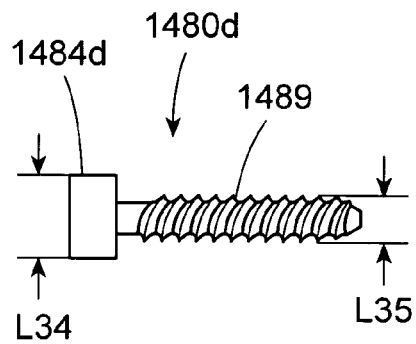
FIG. 14D is a plan view of an embodiment of a connector pin having a sharp threaded portion.

With reference to FIG. 14A, there is shown another embodiment of a connector for use in connecting a needle to an implant. Connector 1460 includes an aperture 1471 through which a connector pin 1480a may be placed such that a portion of connector pin 1480a is inserted into a tube extension 1490, which thus may be connected in turn to an introducer needle as discussed above. With reference to FIGS. 14B, 14C and 14D, connector pins 1480b, 1480c and 1480d may be dimensioned in a variety of manners such that connector 1460 is securely coupled to tube extension 1490. With respect to FIG. 14B, a connector pin 1480b is shown having multiple barbs 1487 and a pinhead 1484b. Pinhead 1484b can be dimensioned with a width L30 of 0.136 inches (0.130 to 0.140 preferred) and the barbs 1487 is dimensioned with a width L31 of 0.83 inches (0.70 to 0.95 preferred). In another embodiment, shown in FIG. 14C, connector pin 1480c is shown having rough scalloped threads 1488, for maintaining connector pin 1480c in tube extension 1490 to hold connector 1460 in position and a pinhead 1484c. Pinhead 1484c can be dimensioned with a width L32 of 0.140 inches (0.125 to 0.155 preferred) and scalloped threads 1488 can be dimensioned with a width L33 of 0.89 inches (0.75 to 0.99 preferred). In FIG. 14D, a connector pin 1480d is shown having sharp, deep threads 1489 which, in certain circumstances, may facilitate connection of connector 1460 to tube extension 1490 and pinhead 1484d. Pinhead 1484d can be dimensioned with a width of 0.137 inches (0.130 to 0.145 preferred) while deep threads 1489 can be dimensioned with a width L35 of 0.91 inches (0.80 to 0.99 preferred). Of course, other shapes and/or proportions may also be used in accordance with the teachings herein. Additionally while these dimensions were found to be beneficial, these connector pins could be designed with differing dimensions as a matter of application specific design choice as determined by one skilled in the art, as instructed by the teachings herein.

Figure 15:
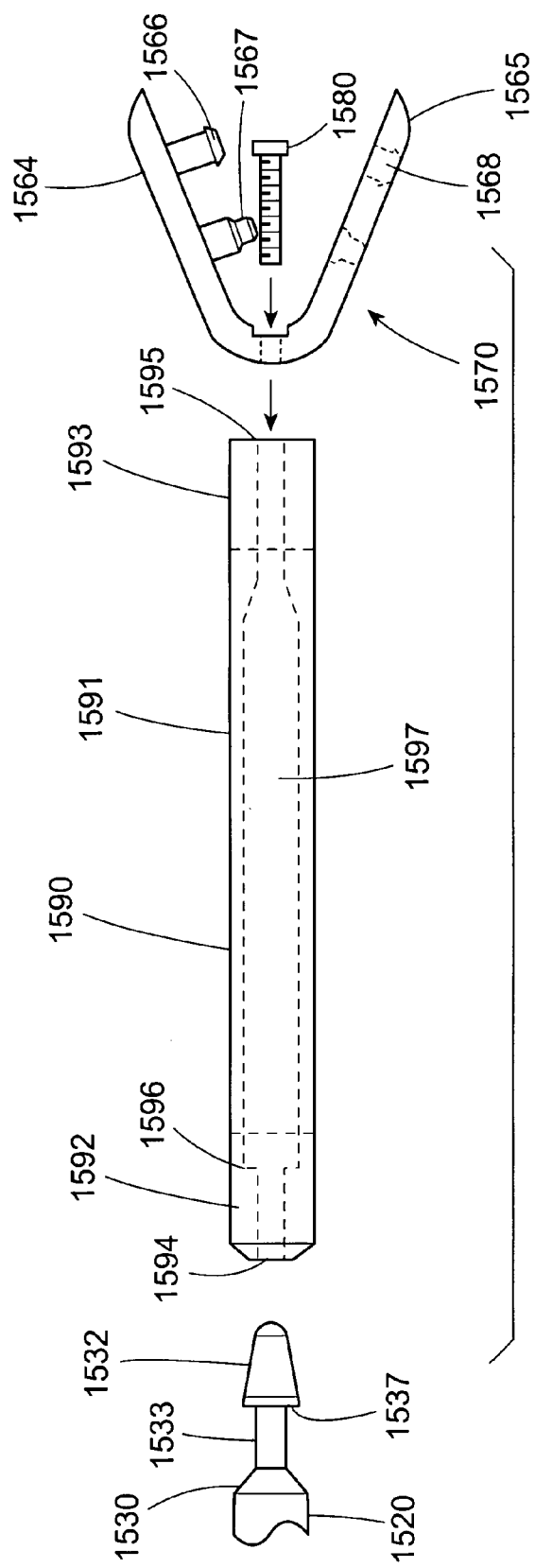
FIG. 15 is a plan view of a portion of an introducer needle having a barb connector tip, an intermediate tube extension, a connector pin and a detachable connector.

With reference to FIG. 15, a connector 1570 is shown that is capable of being connected to tube extension 1590 by way of a pin 1580 into aperture 1595 while barb 1532 of introducer needle 1520 may be inserted into aperture 1594 of tube extension 1590. In one embodiment these may all be joined into one piece. In certain embodiments, tube extension 1590 may be dimensioned such that center portion 1591 is formed of a relatively soft material while end portions 1592 and 1593 are formed of relatively harder material. In certain embodiments, center portion 1591 may be formed with a durometer (hardness) of 55 (50 to 60 preferred) on a shore D scale while end portions 1592 and 1593 may be formed with a durometer hardness of 70 (60 to 80 preferred) on a shore D scale. Accordingly, in such embodiments, tube connector 1590 can be flexible and pliable in its center yet rigid enough at its ends to facilitate coupling of connector 1570 and introducer needle 1520 respectively to opposite ends thereof.

Connector 1570 is shown with arms 1564 and 1565 with an engaging head 1566 and a non-engagement head 1567 located on arm 1564 and an aperture 1568 on arm 1565. When arms 1564 and 1565 are brought together, head 1566 fits into aperture 1568. Connector 1570 can be constructed so that attachment to the implant is releasable or permanent, in that opening arms 1564 to 1565 would significantly impair their functionality. Introducer needle 1520 is also shown having a distal end 1530. In addition, in certain embodiments, tube extension 1590 is formed having a shoulder 1596 within internal channel 1597 such that when barb 1532 of introducer needle 1520 is placed within aperture 1594, introducer needle 1520 becomes locked in place when edge 1537 of barb 1532 that protrudes from shaft portion 1533 passes shoulder 1596. Thus, one continuous angular surface at shoulder 1596 will offer the proximal wall of barb 1537, the edge of which will be loose enough in channel 1597 not to leave a coupling function. The resilient material at end portion of tube connector 1590 allows it to resiliently allow barb 1532 to pass and then be locked in place at shoulder 1596. Accordingly, resilient hard material at the end portions of tube extension 1590 provides a strong attachment to the needle and the connector while the soft central section provides excellent flexibility for insertion of implants. In addition, while barb 1532 becomes locked in place when inserting, tube 1590 can be constructed of materials such that it may be removed by the application of sufficient force to remove introducer needle 1520 thus overcoming the resistance provided by resilient shoulder 1596. In alternate embodiments, a straight undifferentiated tube (not shown) with a single inner surface can be used, which expands even though the tube is an undifferentiated cylinder.

Figure 16A:
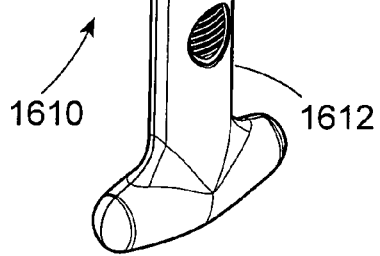
FIGS. 16A, 16B and 16C illustrate a needle outside-in approach to inserting an implant strip with an introducer needle in accordance with an embodiment of the invention.
Figure 16B:
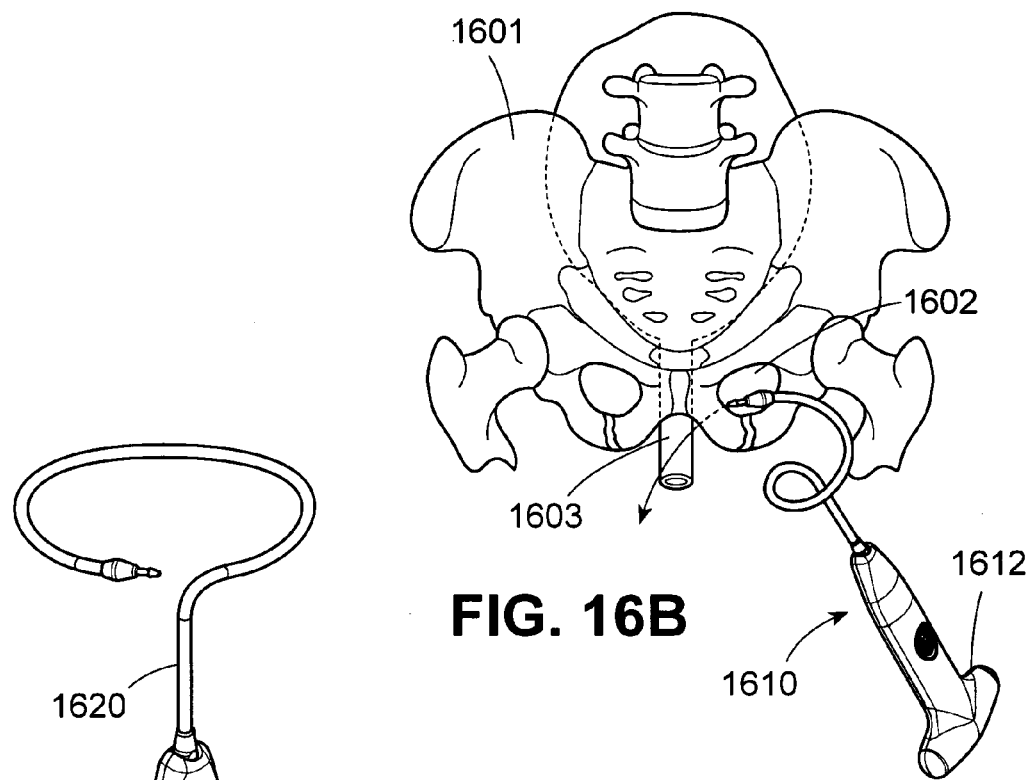
Figure 16C:
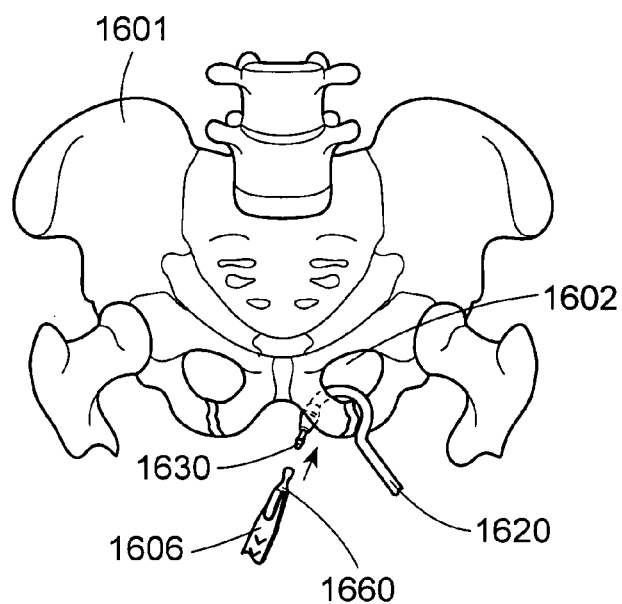

With reference to FIGS. 16A, 16B and 16C, there is shown a method of inserting an implant into a patient. In this method, commonly known as the needle outside-in approach, an introducer needle 1620 coupled to handle 1612 at a junction 1610 is placed, from the outside, inwardly through the obturator foramen opening 1602 in the pubic bone 1601, as is shown in FIG. 16B. Introducer needle 1620 is then maneuvered out the vaginal opening where a connector 1660 attached to a tissue implant 1606 may be attached to a distal end 1630 of introducer needle 1620, as is shown in FIG. 16C. Finally, introducer needle 1620 is retracted back through the obturator foramen pulling a section of the tissue implant out with it. The procedure is then repeated on the other side of the patient to install tissue implant 1606 against the urethra 1603.

With reference to FIGS. 17A, 17B and 17C, there is shown another method of inserting a tissue implant commonly referred to as the needle inside-out approach. First, the introducer needle 1620 is passed from the inside, under the urethral meatus and then out through the obturator foramen, as shown in FIG. 17B. As can be seen in FIG. 17C the inside-out approach has decreased ability to properly maneuver the needle and handle in once the needle is inserted.

With reference to FIGS. 18A, 18B, 19A and 19B, there is illustrated several embodiments of introducer needles having shape characteristics which facilitate retropubic tissue insertions and transobturator tissue insertions. A retropubic introducer needle 1820a is shown in FIGS. 18A and 18B. As is shown in FIGS. 18A and 18B, introducer needle 1820a can have a radius R1 of approximately 3.0 inches (2.5 to 3.5 preferred) and form an approximately 90-degree bend (80 to 100 preferred) (traversing an approximate quarter circle arc) and having a relatively large radius of curvature.

Because of the requirements of a transobturator procedure, the shape of a typical transobturator introducer needle, as shown in FIGS. 19A and 19B is different than that of the retropubic needle 1820a. Accordingly, the transobturator introducer needle 1920a, in this instance a 2-dimensional hook version, which can have a radius R2 of approximately 1 to 1.5 inches and traverses a 180-degree half-circle arc (165 to 185 preferred) of distance and along a relatively tight radius of curvature, during the appropriate 180-degree rotation that the transobturator introducer needle 1920a makes during the procedure.

Figure 20:
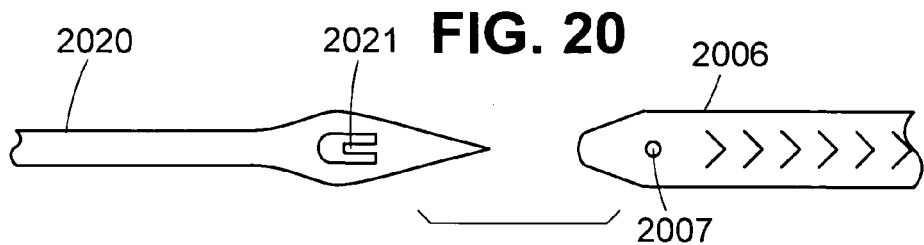
FIG. 20 is a top plan view of an implant strip defining a hole and an introducer needle having a tab, the hole being designed to hook onto the tab, to secure the implant strip to the insertion needle.
Figure 21:
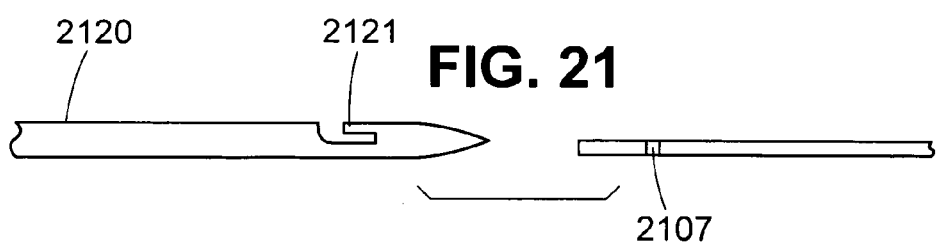
FIG. 21 is a side elevational view of the implant strip and introducer needle of FIG. 21A.

With reference to FIG. 20, there is shown an embodiment wherein an introducer needle 2020a includes a protruding tissue hook 2021a designed and configured to fit aperture 2007a of implant 2006. Accordingly, in certain embodiments, implant 2006 can have its aperture 2007a placed over tissue hook 2021 thus securing tissue implant 2006 to introducer needle 2020 without the need for a separate and independent connector. In FIG. 21, introducer needle 2120 includes protruding hook 2121 designed to fit into tissue aperture 2107.

Figure 22A:
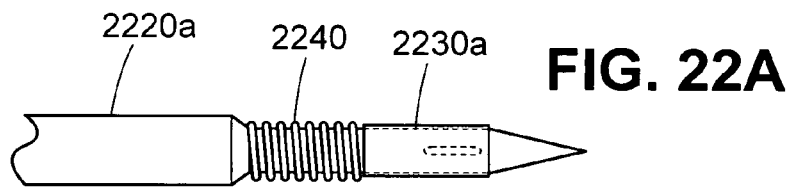
FIG. 22A is a side elevational view of an embodiment of an introducer needle having a spring loaded collar, the collar being in the closed position, with no portion of an implant strip inserted therein.
Figure 22B:
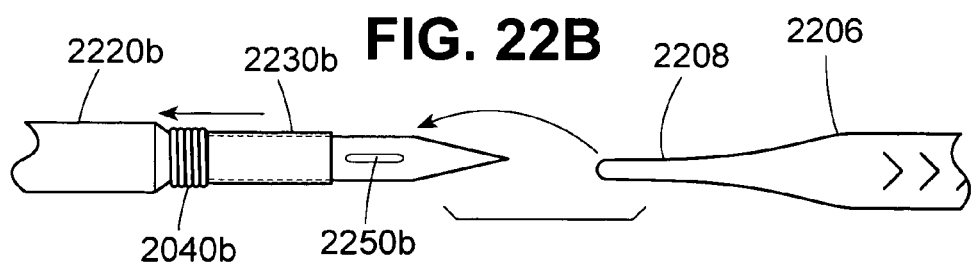
FIG. 22B is a side elevational view of the introducer needle having a spring loaded collar of FIG. 22A, the collar being in the open position.
Figure 22C:
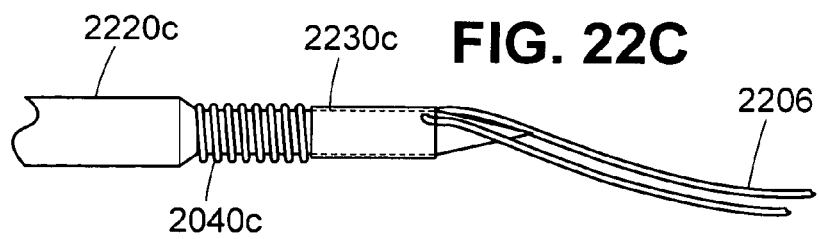
FIG. 22C is a side elevational view of the introducer needle having a spring loaded collar of FIG. 22A, the collar being in the closed position, with a narrow tab of the implant strip being secured by the collar.

In another embodiment of the invention, an implant 2206d may be secured directly to introducer 2220a, 2220b or 2220c without need for an independent connector is shown in FIGS. 22A, 22B and 22C, respectively. Introducer needles 2220a, 2220b and 2220c each have a sliding collar 2230a, 2230b and 2230c, respectively, that are biased by a spring member. The sliding collar may be pushed away from implant 2206 thus exposing a needle aperture 2250 into which an end 2208 of implant 2206 may be placed. After an end 2208 of implant 2206 is placed into the needle aperture, the sliding collar may be released and caused to spring back to its original position by the biasing force supplied by the respective spring members. Accordingly, collar 2230 serves to pinch implant 2206 into needle aperture 2250 thus securing implant 2206 to the introducer needle without the need for a separate and independent connector.

Figure 23A:
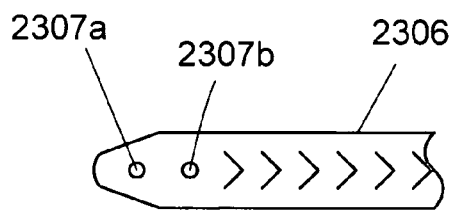
FIGS. 23A and 23B and 23C show an embodiment of an implant strip and introducer needle similar to that of FIGS. 20 and 21, but with the implant strip defining two holes, and the introducer needle having two tabs, the holes being designed to hook onto the tabs, to secure the implant strip to the introducer needle.
Figure 23B:
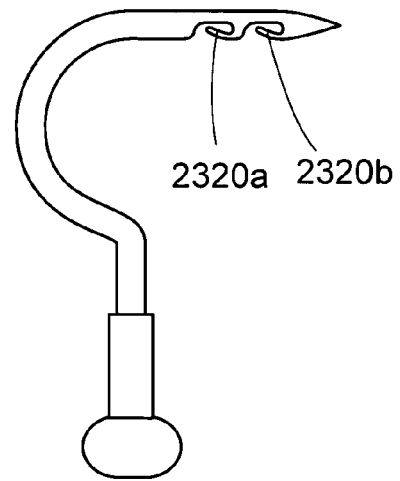
Figure 23C:
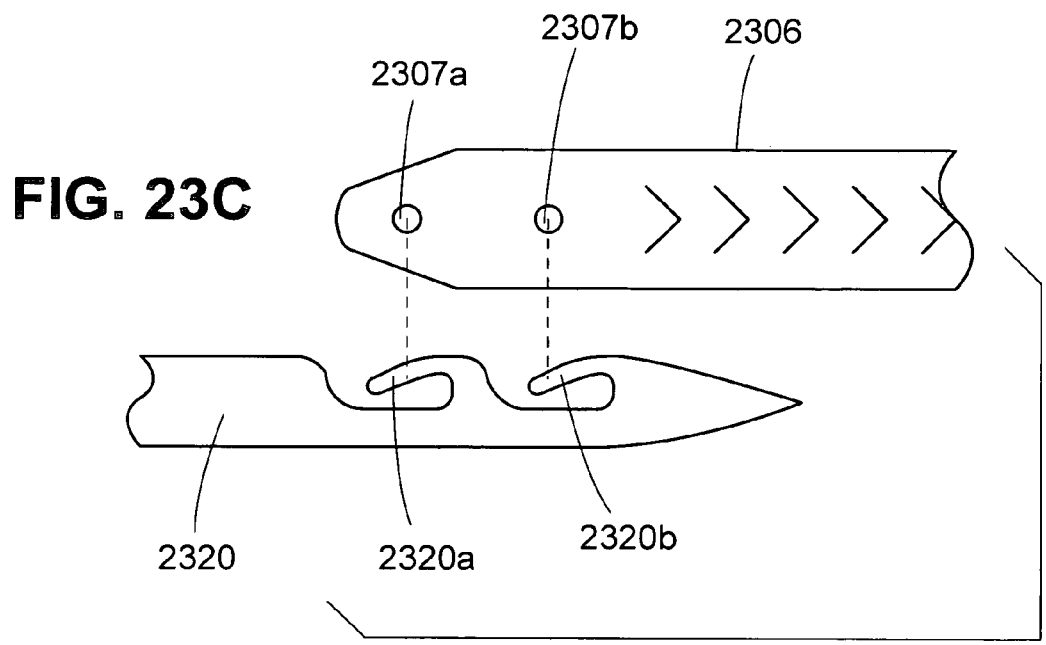

With reference to FIGS. 23A and 23B, there is shown an introducer needle 2320c having twin tissue hooks 2320a and 2320b similar to that shown in FIGS. 21A and 21B. This embodiment differs in that two tissue hooks are present on an introducer needle, instead of just one hook, thus the introducer needle is capable of coupling directly with a tissue implant (optionally natural or synthetic material) 2306 having two tissue apertures 2307a and 2307b and without the need for an independent and separate connector. FIG. 23C shows an exploded view of FIGS. 23A and 23B respectively and how they connect to each other.

Figure 24A:
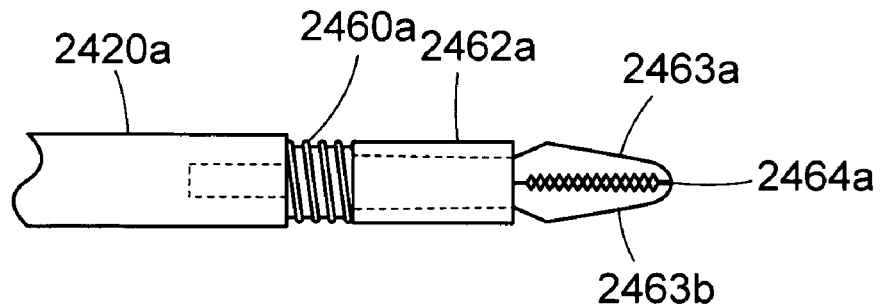
FIG. 24A is an elevational view of another embodiment of an introducer needle having a gripping jaw assembly, the assembly including a penetrating tip, and a lock collar with a sprint, the lock collar being in the closed position.
Figure 24B:
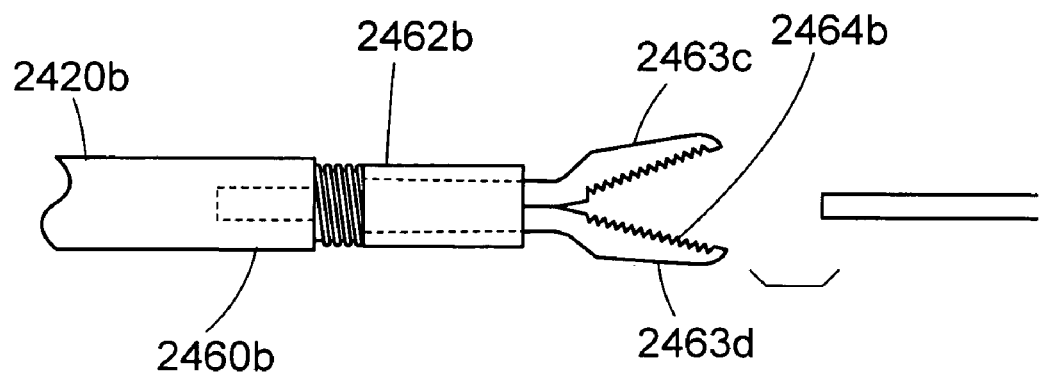
FIG. 24B is the introducer needle of FIG. 24A, the lock collar in the retracted position, for receiving an end of an implant strip.
Figure 25A:
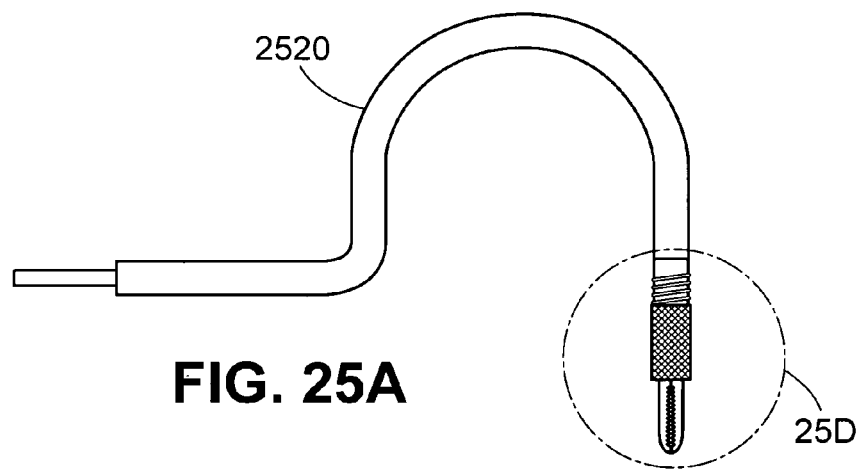
FIG. 25A is a plan view of an introducer needle, a jaw assembly having an outer threaded portion, and a twist threaded collar for closing the jaw assembly.
Figure 25B:
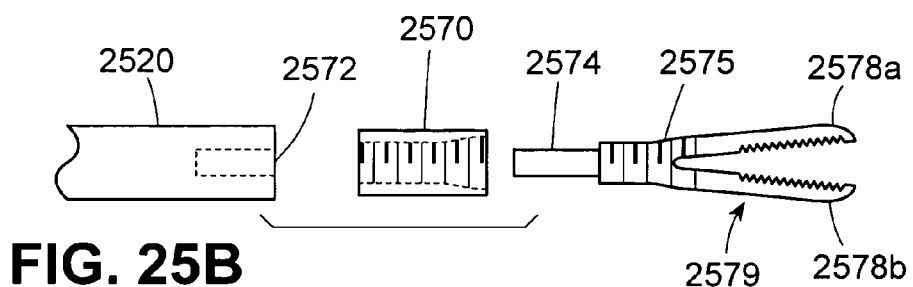
FIGS. 25B, 25C and 25D show the introducer needle, jaw assembly and twist threaded collar of FIG. 25A being assembled and the jaw assembly being closed by rotation of the twist threaded collar.
Figure 25C:
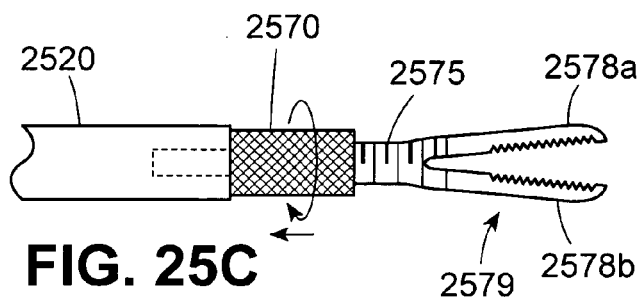
Figure 25D:
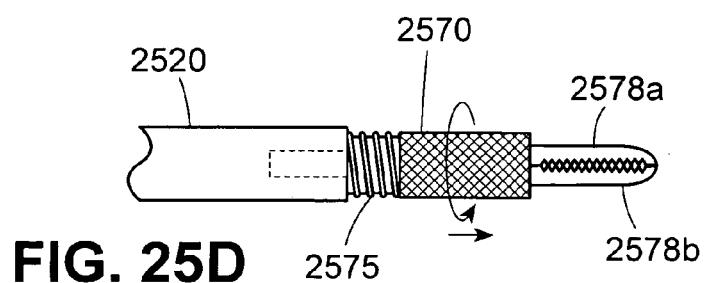

Another embodiment of the invention designed to allow for the coupling of introducer needle 2420a and 2420b directly with natural or synthetic tissue implant 2406 is shown in FIGS. 24A and 24B, respectively. This embodiment is similar to that shown in FIGS. 22A, 22B and 22C, in that introducer needle 2420 has a sliding collar 2462 that is biased by a spring member 2460. Instead of an aperture into which tissue implant 2406 is placed to be subsequently pinched, however, the present embodiment includes a pair of jaws 2463 having a plurality of penetrating teeth 2464. When a collar 2462 is biased and positioned toward the tissue implant 2406 by the spring member 2460, jaws 2463 are forced closed. When collar 2462 is slid back away from tissue implant 2406 and against the biasing force of spring member 2406, jaws 2463 open. In turn, when jaws 2463 open, a portion of tissue implant 2406 may be placed between the jaws 2463. Collar 2462 is then released and biased toward the tissue implant 2406 by spring member 2460, thus closing jaws 2463 and clamping penetrating teeth 2464 into tissue implant 2406, and thus securing tissue implant 2406 to the introducer needle 2420 without the use of a separate and independent connector.

Figure 26:
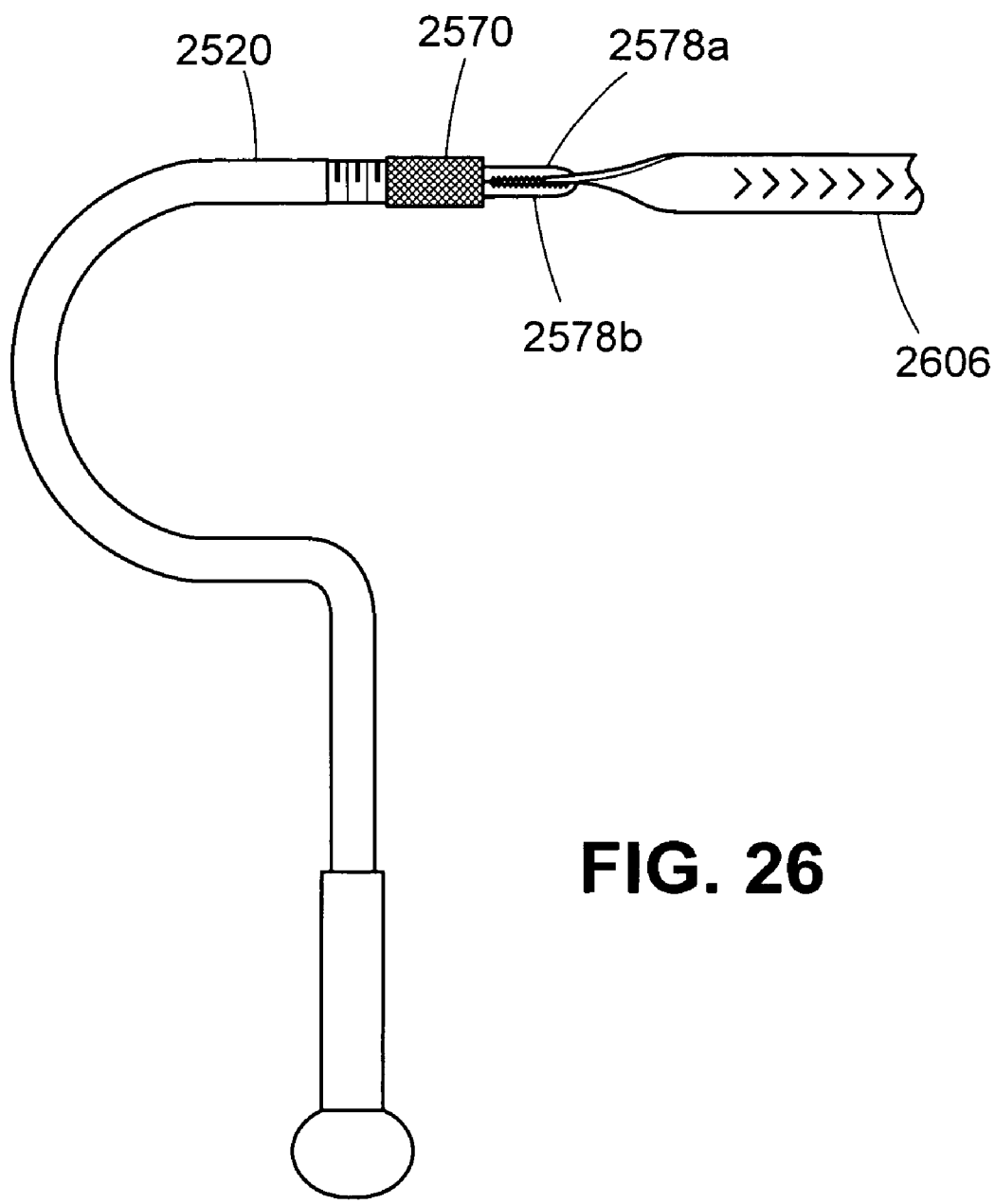
FIG. 26 is a plan view of the introducer needle, jaw assembly and twist threaded collar of FIG. 25A, with an insert strip secured by the jaw assembly.

Another embodiment of the invention wherein a tissue implant may be directly coupled to an introducer needle without the use of a separate and independent connector is shown in FIGS. 25A-25D. In this embodiment, introducer needle 2520 has a recess aperture 2572 into which an extended portion 2574 of jaw piece 2579 may extend. A threaded collar 2570 is designed to thread onto threads 2575 on jaw piece 2579. Once extended portion 2574 is placed through collar 2570 into recess aperture 2572, and collar 2570 is twisted over threads 2575, jaws 2578a and 2578b tend to be forced shut. If a tissue implant 2606 is placed between the jaws 2578a and 2578b prior to rotating of the collar 2570, the tissue implant may be conveniently directly secured to introducer needle 2520 without the need for a separate and independent connector as can be seen in FIG. 26.

In certain embodiments, an introducer device 2710 can be designed and dimensioned such that it is capable of inserting a soft, flexible filament 2740. With reference to FIGS. 27A, 27B and 27C, flexible filament 2740 may have attached to a first end rigid tip 2744 having connection portion 2742. Attached to a second end of flexible filament 2740 is a generally y-shaped clamshell type connector 2760, similar to connector 60 of FIG. 1A. Introducer 2710 has introducer needle 2720 extending from an introducer handle 2712. Introducer needle 2720 comprises a shaped channel portion 2721 having an open channel 2722 defined therein. Channel 2722 is designed and dimensioned such that flexible filament 2740 may be placed within channel 2722 with rigid tip 2744 protruding out the distal end 2724 of channel portion 2721.

Channel portion 2721 is also designed such that the second end of flexible filament 2740 extends out the other side of shaped channel portion 2721 such that connector 2760 is positioned to receive a tissue insert in a manner as described above. It should be understood that the use of the flexible filament allows one to mount the filament into a guide and once the introducer is assembled it can grab the rigid tip 2744 and pull it through the channel 2722. Once the filament has been curved that shape will hold even once it is pulled through the channel 2722.

FIGS. 28A, 28B and 28C depict another embodiment of introducer 2810 which is designed and dimensioned for use with a flexible filament 2840. Shaped channel 2021a of an introducer needle has a partial open channel 2822 defined therein, as well as a tapered cleat section 2825 for cinching a portion of flexible filament 2840 therein. In use, a portion of flexible filament 2840 may be placed into open channel 2822 and cinched into tapered cleat section 2825 such that flexible filament 2840 is maintained in place. As with the previously discussed embodiment employing a flexible filament, connector 2860 on a second end of flexible filament 2840 extends out from introducer needle 2809.

FIG. 28B depicts a cross-sectional view of an embodiment of open channel of 2821b wherein channel 2822b is fully opened such that flexible filament 2840b is compressed within channel 2822b such that flexible filament 2840b is retained in place. In an alternate embodiment, as illustrated in FIG. 28C, a cross-section of open channel 2821 is shown wherein a top portion of open channel 2822c is partially closed in such a manner that it is narrower than flexible filament 2840c, thus facilitating retention of flexible filament 2840 within channel 2822c.

With reference to FIGS. 29A, 29B and 29C, another embodiment is shown in which a flexible filament 2940 is used. Flexible filament 2940 has a connector block 2941 attached to an extension piece 2942. Connector block 2941 may be placed into a recess 2926 of an introducer needle 2920 and then pulled back into a channel 2927 such that flexible filament 2940 may be selectively attached and detached from introducer needle 2920.

Figure 30A:
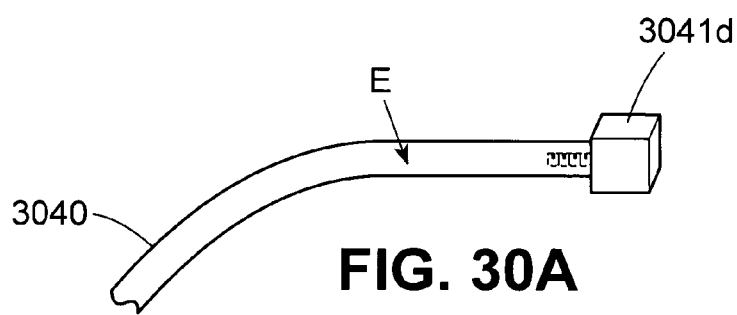
FIG. 30A is a perspective view of an flexible filament member having a connector tab at an end thereof.
Figure 30B:
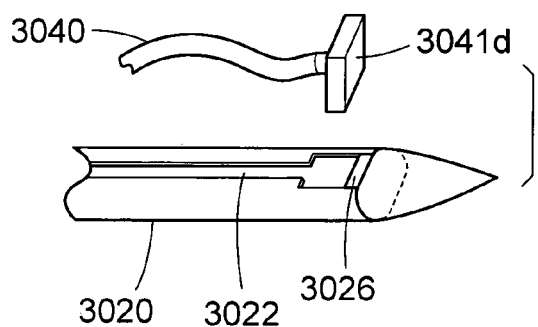
FIG. 30B is a perspective view of the flexible filament member of FIG. 30A and an introducer needle having top ad bottom recesses designed to selectively receive the flexible filament member and the connector tab.
Figure 30C:
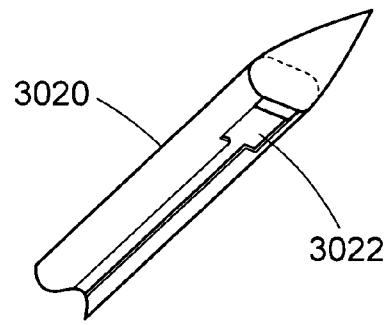
FIG. 30C is a perspective view of the introducer needle of FIG. 30B, showing the top and bottom recesses.

With reference to FIGS. 30A, 30B and 30C, there is shown another embodiment wherein a flexible filament 3040 may be placed within a channel 3022 of an introducer needle 3020. Introducer needle 3020 has an opposing aperture located opposite aperture 3026. Once inserted, connection block 3041 can be removed from channel 3022 by pushing into opposing aperture 3026 in direction E, thus pushing connection block 3041 out an aperture 3026.

Figure 30D:
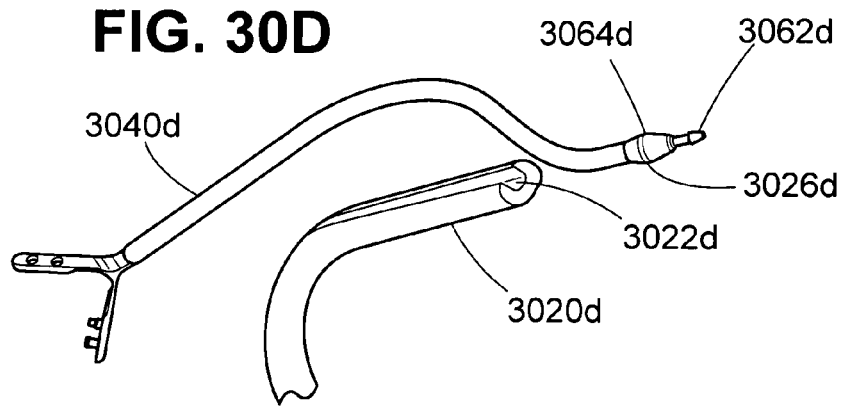
FIG. 30D is a perspective view of another embodiment of an introducer needle, the introducer needle having a guide channel for accepting an introducer filament member having a needle tip attached thereto for securing the introducer filament member in the guide channel.

In a related embodiment illustrated in FIG. 30D, introducer needle 3020d has a channel 3022d for receiving a flexible filament 3040d. A surface 3026d of introducer needle 3020d is designed to abut with surface 3064d of rigid needle 3062d when flexible member 3040d is positioned within channel 3022d of introducer needle of 3020d.

Various embodiments of tube extension 3167 and connector 3160 are illustrated in FIGS. 31A, 31B, 31C, 31D and 31E. FIGS. 31A and 31B showtube extension 3167a and connector 1060a attached thereto. FIGS. 31C and 31D illustrate a modified connector 3160b wherein the distance D1 between a pair of fingers 3154b and 3155b is relatively less than that from the embodiment of FIGS. 31A and 31B. In addition, the length D2 of connector 3160b is relatively shorter than that of the embodiment illustrated in FIGS. 31A and 31B. The shorter length may benefit the performance of a surgical procedure as more flexibility and maneuverability of the implanter device may result. In FIG. 31E, a connector 3160e has a tapered front portion 3161e to facilitate passage through the body. In addition, in this embodiment, the front surface 3121b of introducer needle 3120 is flared and wider than connector 3160e such that dilation may occur when the introducer is passed through the body.

Various alternative embodiments of connectors are shown in FIGS. 32A, 32B, 32C, 32D and 32E. In FIG. 32A, a connector 3260a is shown connecting to a tube extension 3267a by a connecting pin 3280a, as described above with respect to other embodiments. With reference to FIG. 32B, a connector 3260b is shown having relatively thick wall portion 3290 and relatively thin wall portions 3281. Thick portion 3290 facilitates a strong connection to tube extension 3267 via connecting pin 3280b while thin portions 3281 facilitate maximum flexibility of arms 3254b and 3255b for closing. FIG. 32C illustrates that connector 3060b, having relatively minimal length of arms 3254b and 3255b, facilitates easy passage through a tight passage in the body during a surgical procedure. In FIG. 32D, arms 3254d and 3255d are shown with tear-in portions 3290d and 3291d to provide extra gripping force to facilitate connection with a synthetic or tissue implant strip. In FIG. 32E a connector pin 3280e is shown having a round pinhead 3284e. A connector pin 3282e is shown having a ground-down and squared-off connector head 3284e, thus facilitating improved distribution of the force load on the plastic connector 1060 and thus facilitating an improved connection.

Figure 33A:
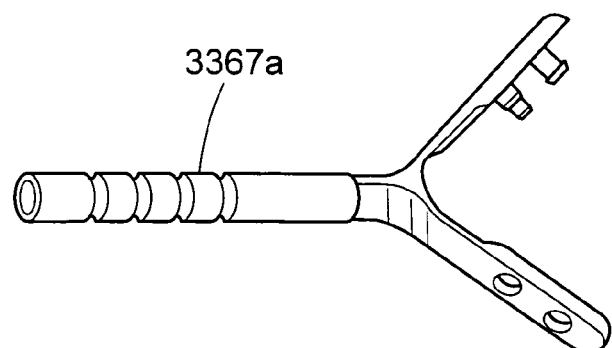
FIGS. 33A, 33B and 33C are perspective views of embodiments of snap connectors for coupling to implant strips.
Figure 33B:
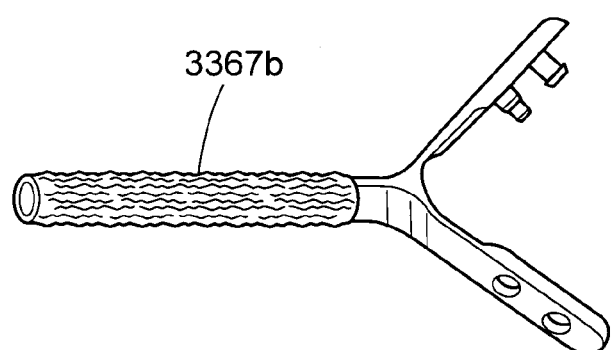
Figure 33C:
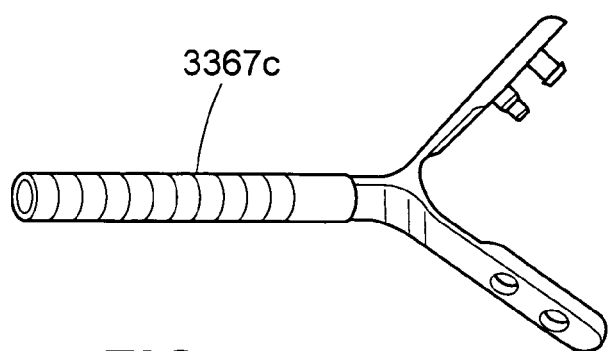

To increase the frictional force at the surface of a tube extension and to facilitate gripping of the tube extension, various embodiments may be employed as are illustrated in FIGS. 33A, 33B and 33C. In FIG. 33A, tube extension 3367a has scalloped cuts on its side thus facilitating gripping and connecting by a doctor. Tube extension 3367b has a textured surface which could be made, for example, by acid or solvent etching. Tube extension 3367c has annular cuts similar in appearance to those found on a flexible or bendable straw. All three of these embodiments facilitate gripping by a doctor of the tube extension such that an easier connection may be made.

Figure 34B:
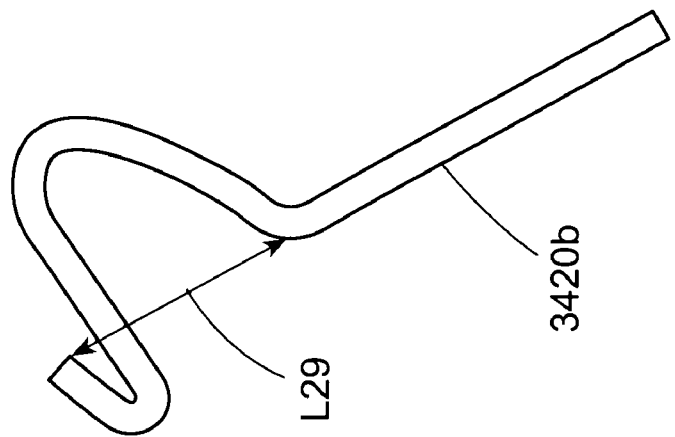
FIGS. 34A and 34B are perspective views of hook and helical style introducer needles, respectively.
Figure 34A:
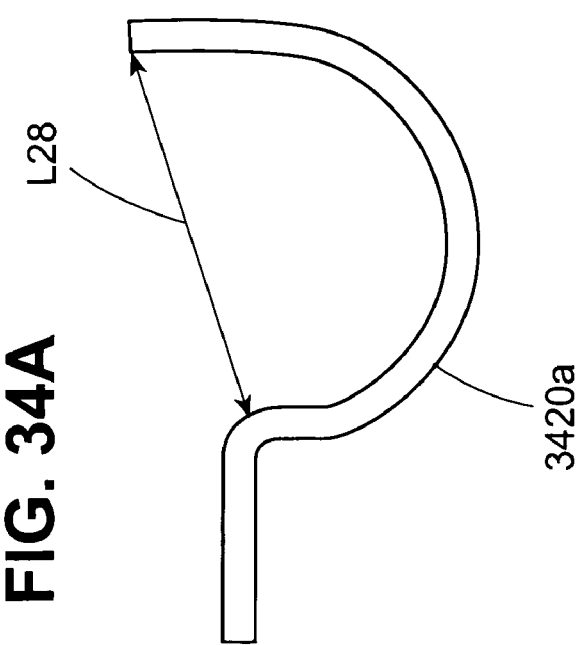

Two additional embodiments of introducer needles are illustrated in FIGS. 34A and 34B. A hook-style introducer needle 3420a is shown in FIG. 34A, having a straight line tip-to-bend distance of L28, while helical style introducer needle 3420b in FIG. 34B has a straight line distance from tip-to-bend of L29. These distances may be varied depending on application. For example, typical lengths for these distances L28 and L29 may vary between 2 and 5 inches, although other lengths may also be used, as a matter of application specific design choice made by one skilled in the art, as instructed by the teachings herein.

Figure 35:
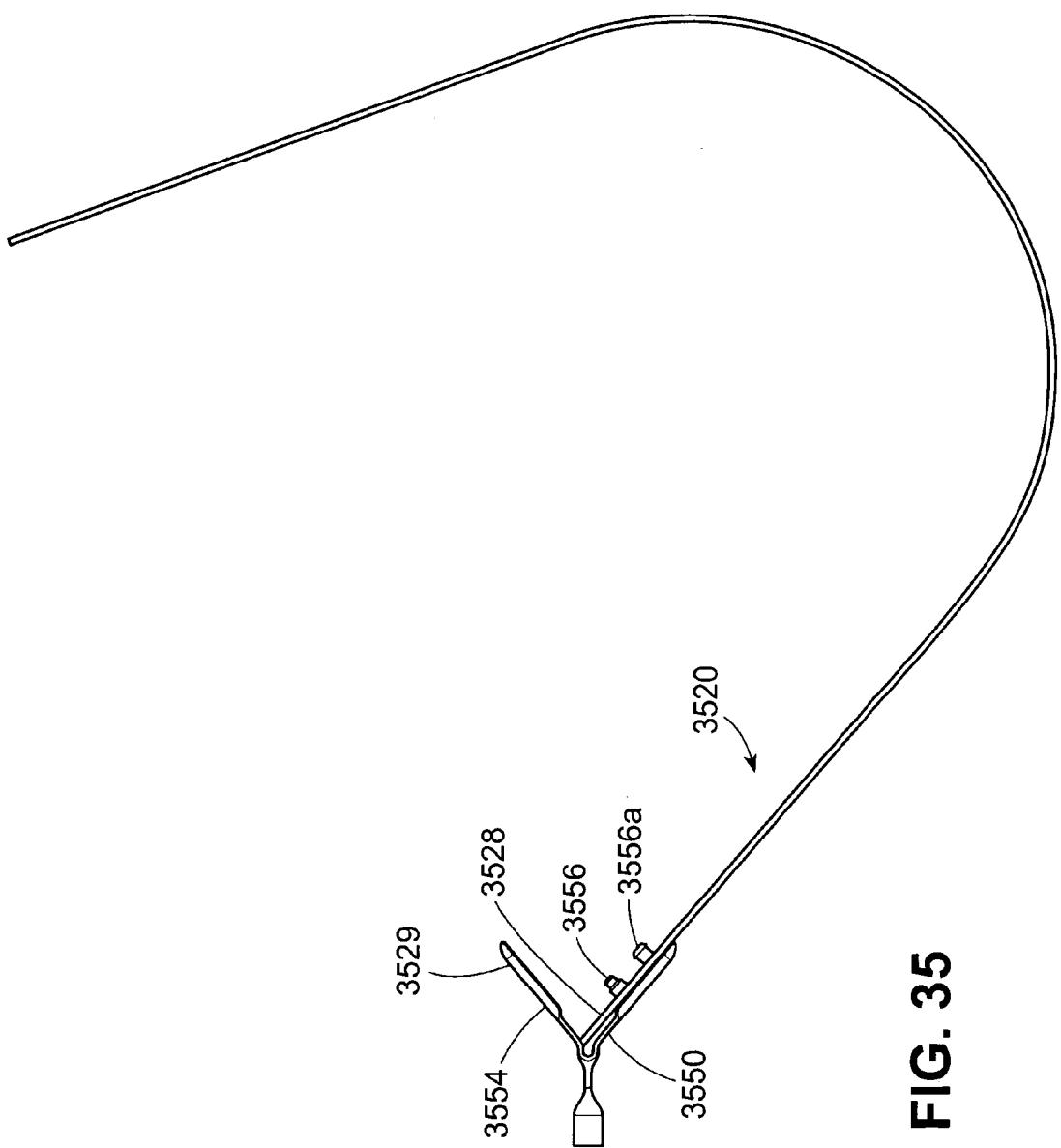
FIG. 35 is a perspective view of an introducer needle and snap connector positioned for placement on the snap connector.

With reference to FIG. 35 there is shown a connector 3550 mounted on extended flat portion 3528 of implant 3520. Similar to above embodiments, arm 3554 can be closed over extended flat portion 3528 such that connector 3550 is secured to implant 3520 as projections 3556 and 3556a extends through aperture 3529.

Figure 36:
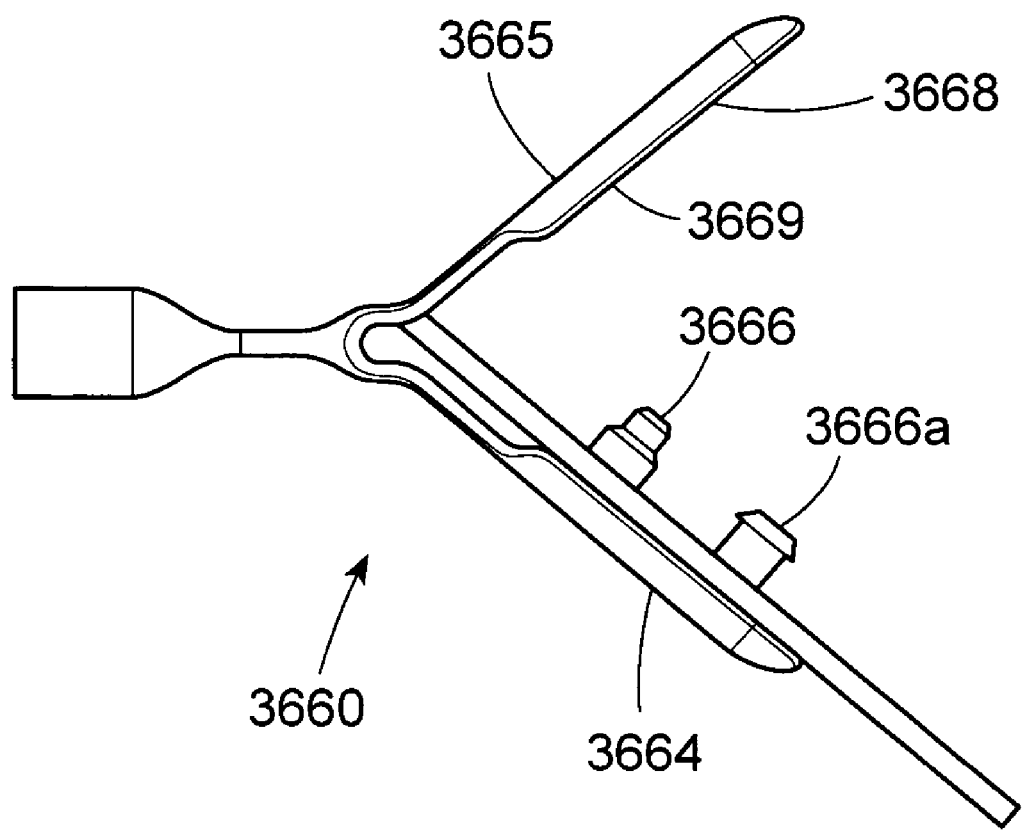
FIG. 36 is a perspective view of a snap connector having a tube connection portion for coupling with an introducer needle.

With reference to FIG. 36, there is shown connector 3660 in accordance with embodiments of the present invention. As seen in FIG. 36, connector 3660 comprises arms 3664 and 3665, arm 3664 including projections 3666 and 3666a. Projection 3666a having a head portion that extends through and locks onto aperture 3668 and projection arm 3666 having no head allowing the aperture to just slip into aperture 3669 when hinged arm 3664 and hinged arm 3665 are pressed together.

Figure 37:
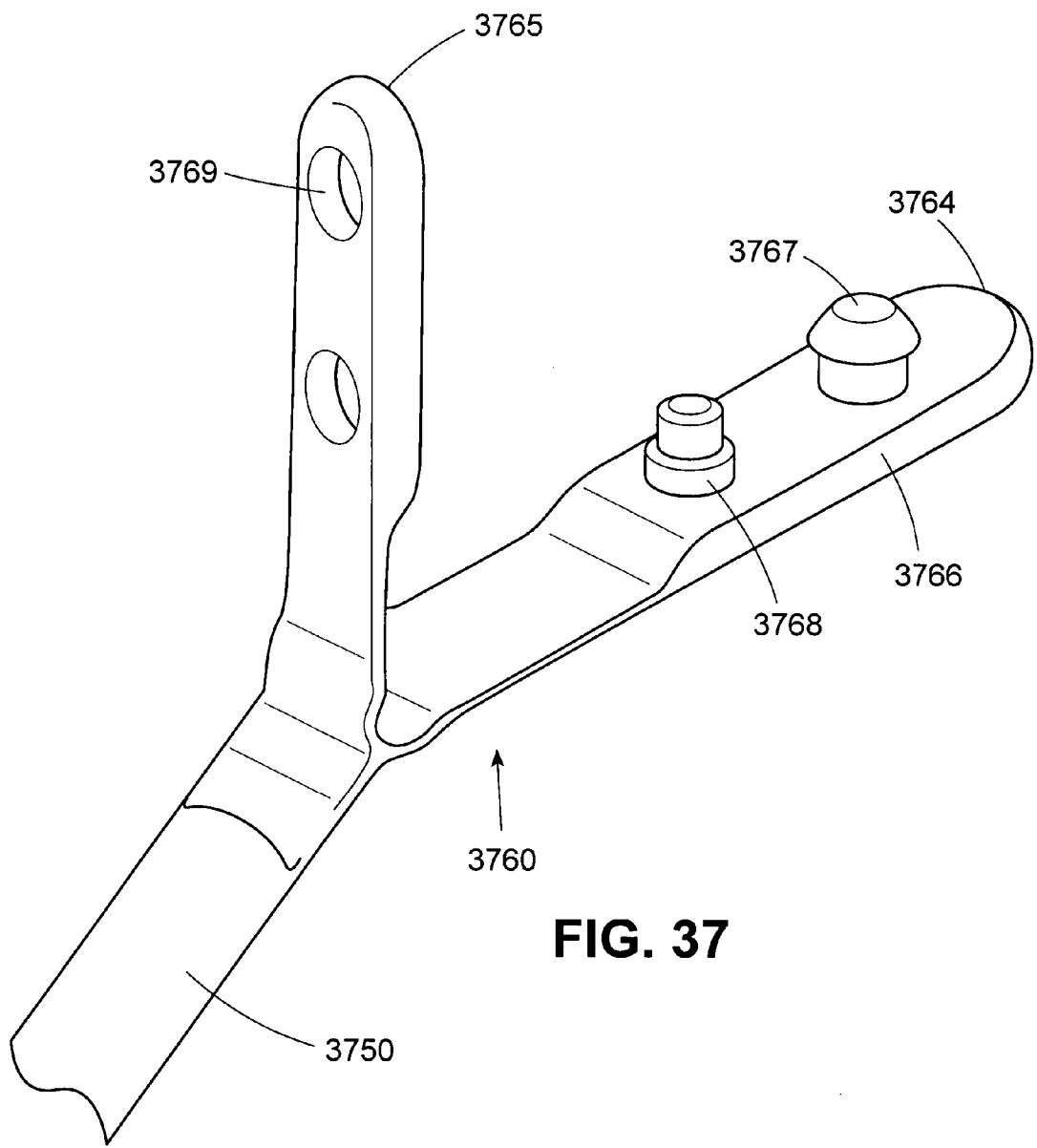
FIG. 37 is a perspective view of a snap connector having a tube connection portion for coupling with an introducer needle, and having two pins on the implant strip connection portion, with only one pin having an engagement structure.
Figure 38:
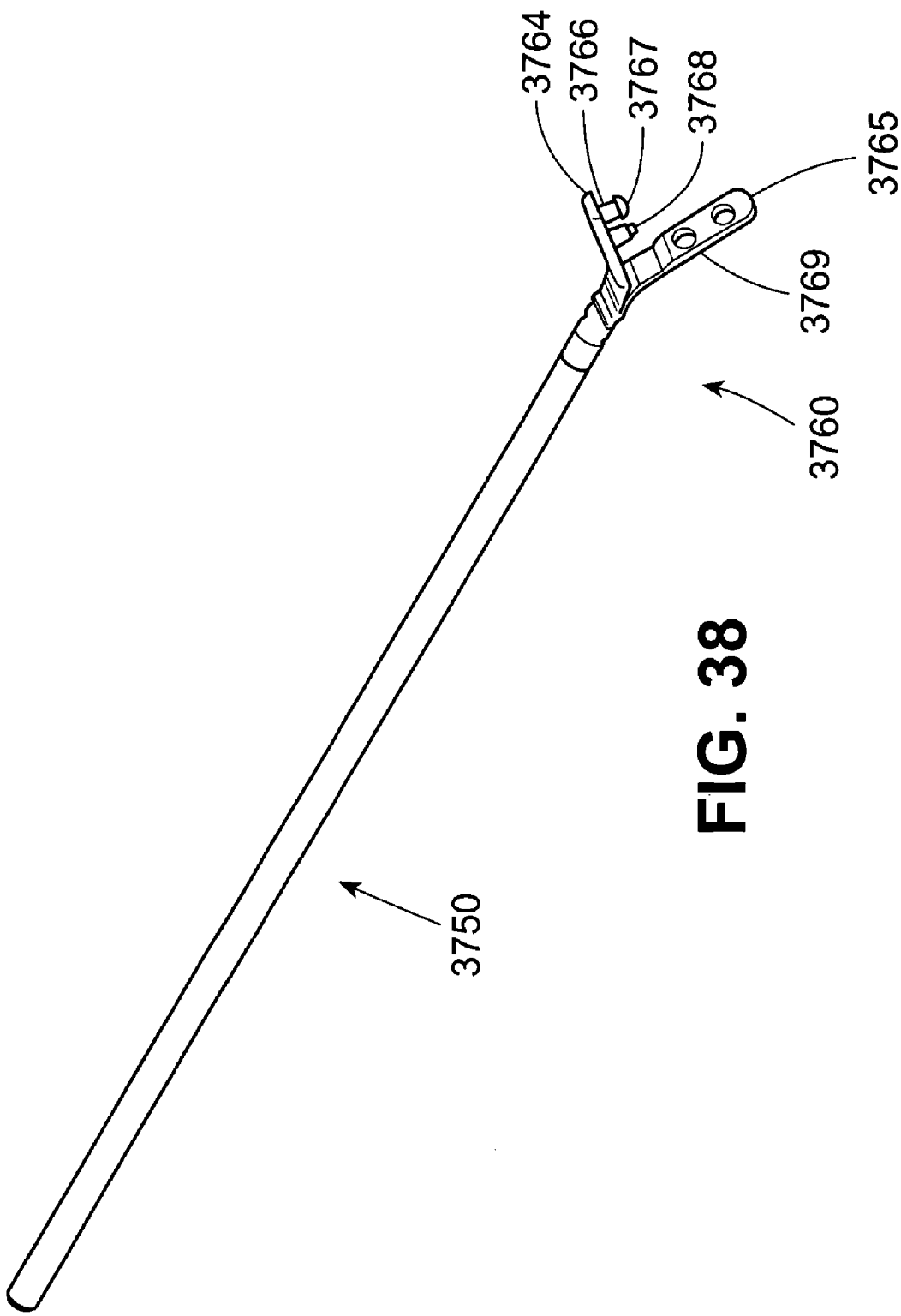
FIG. 38 is another perspective view of the connector of FIG. 37.
Figure 39:
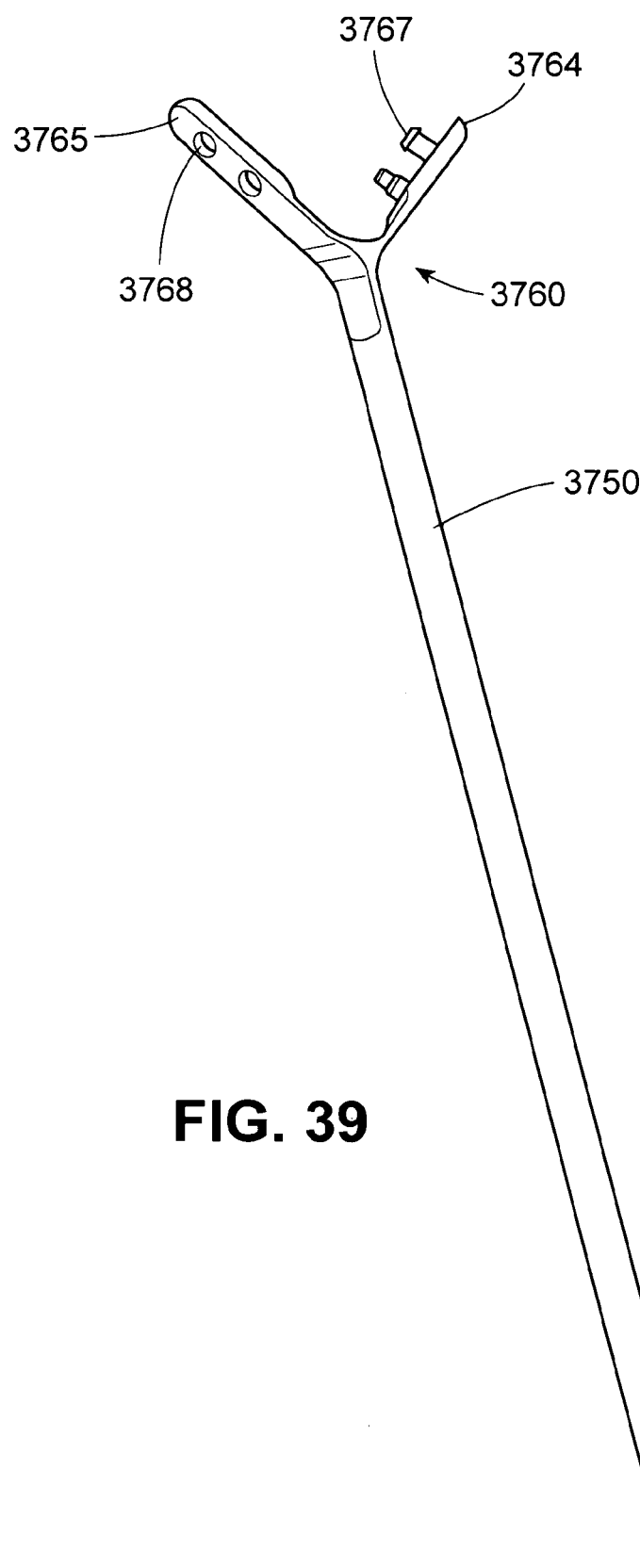
FIG. 39 is another perspective view of the connector of FIG. 37.

A connector 3760 is shown in FIGS. 37, 38 and 39. Connector 3760 is connected to connector tube 3750 has arms 3764 and 3765 with one projection 3766 with an engaging head 3767 and a second projection 3768 without an engagement head disposed on arm 3764. Aperture 3769 is located on arm 3765. A benefit of only having one projection with an engagement head thereon is that the use of two projections both with engagement heads tends to cause or amplify alignment problems when snap closing the connector. Because one projection with an engagement head can be sufficient to secure the connector in the closed position, second projection 3768 serves to stabilize the tissue implant when in place but without contributing to misalignment problems of the connector when closing. In addition, less mechanical force is required to snap the connector closed as compared to a connector having two projections with engagement heads, although sufficient force is provided by the single projection with an engagement head such that the connector is sufficiently secured in the closed position.

Figure 40:
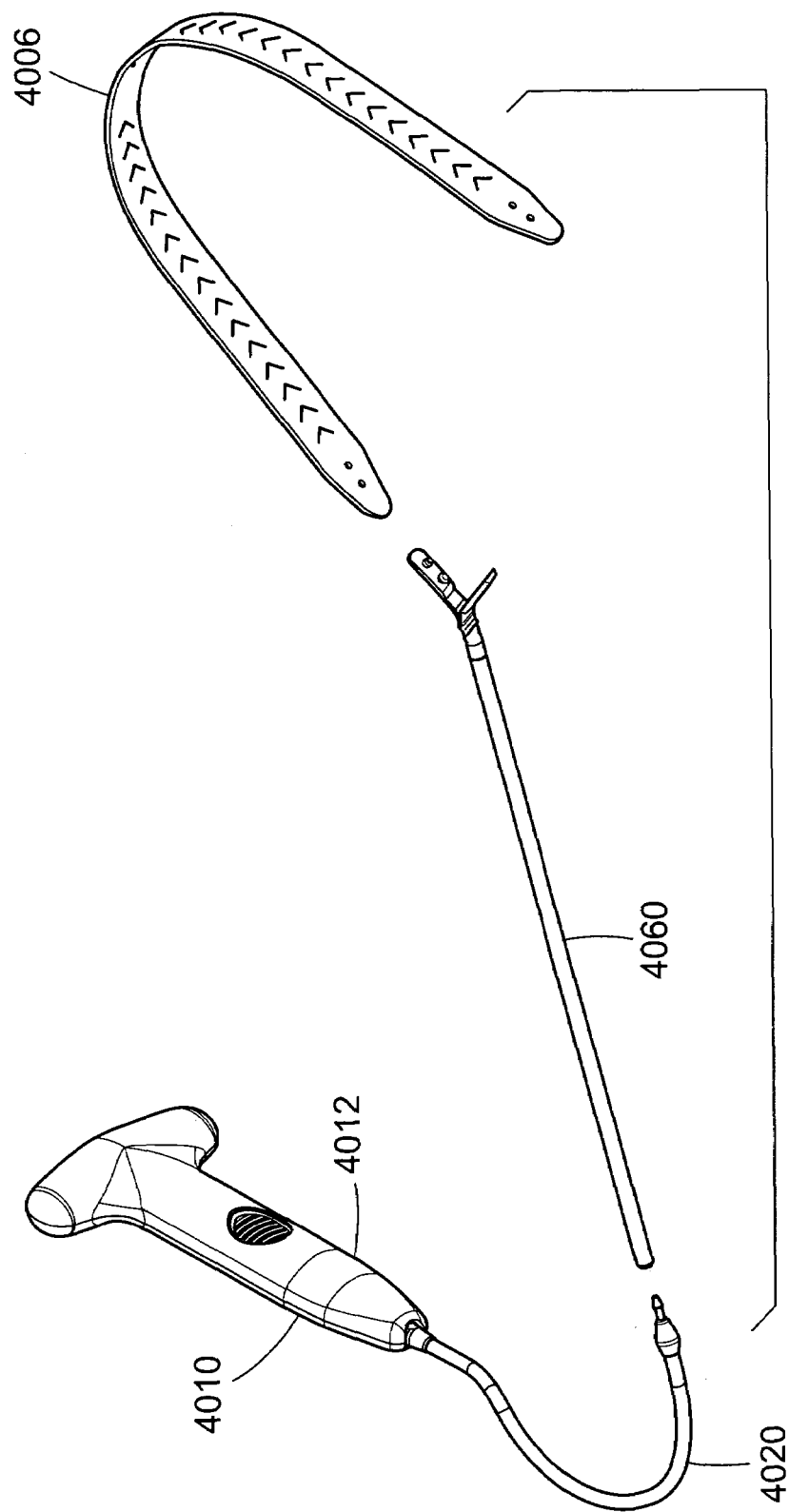
FIG. 40 is a perspective view of an introducer assembly comprising an introducer handle and an introducer needle, a detachable connector having a tube connection portion, and an implant strip, and another detachable connector.

With respect to FIG. 40, there is shown an introducer device 4010 having introducer handle 4012 and introducer needle 4020 and tissue implant 4006 position to be connected as both sides to connector 4060.

Figure 41:
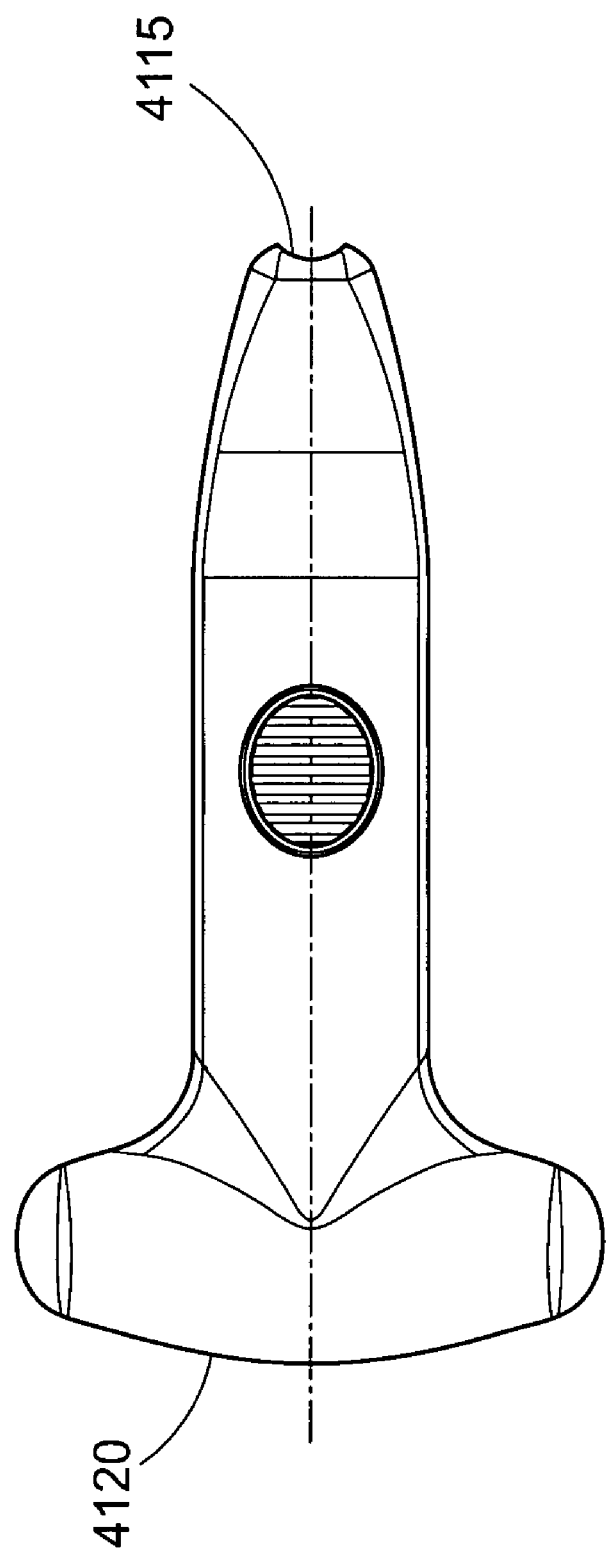
FIG. 41 is a top view of the introducer handle of FIG. 40.

A top view of introducer handle 4012 is shown in FIG. 41. As can be seen in FIG. 41, introducer handle 4012 has an opening 4115 at its distal end to attach to the introducer needle and a protrusion 4120 at its proximal end where the operator of the handle can grasp the handle.

Figure 42:
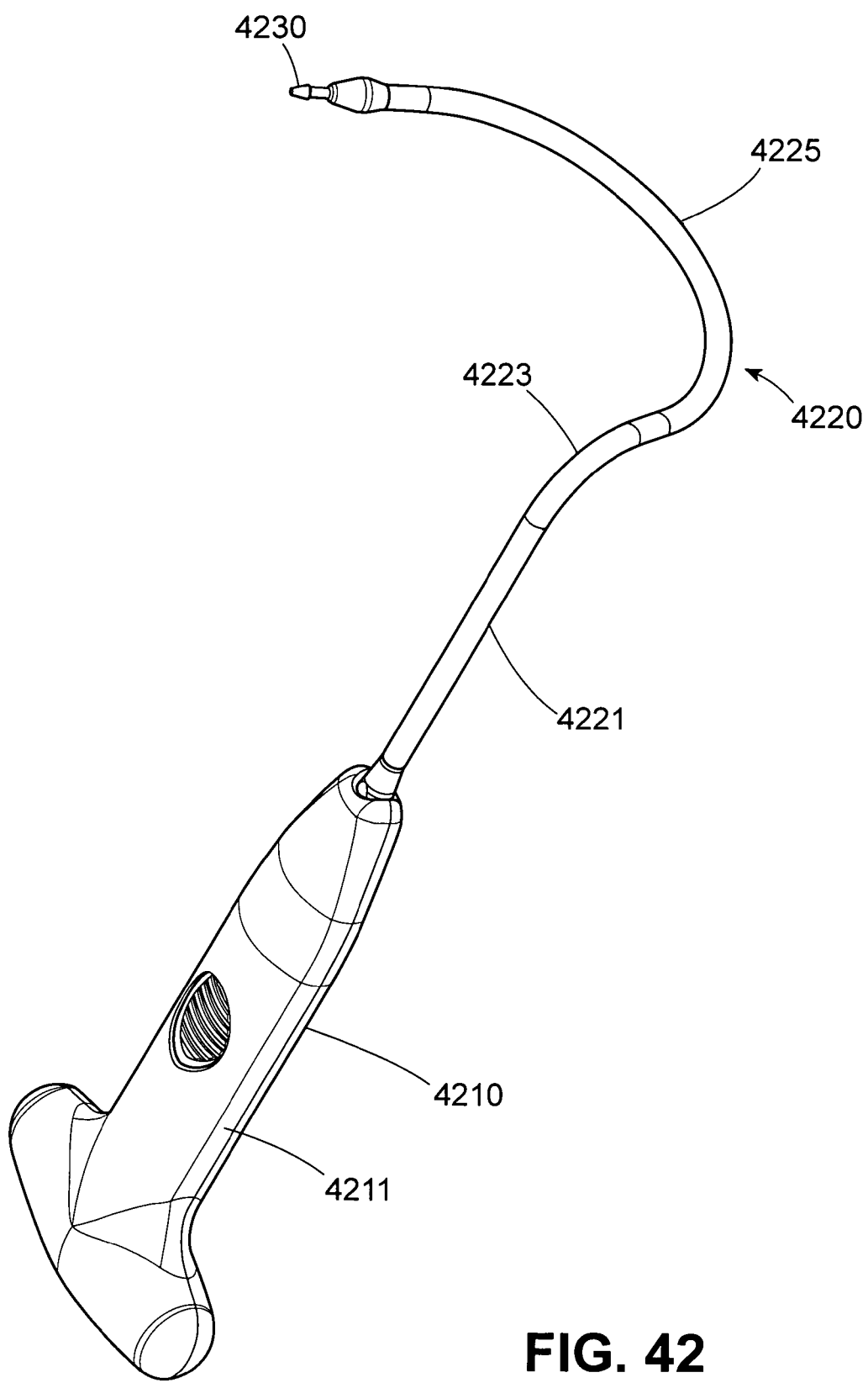
FIG. 42 is a perspective view of an introducer needle assembly having a generally halo shape with a shaft extending from a handle and a curved portion perpendicular distal end, in a single plane, perpendicular to the shaft.

Different geometrically shaped introducer needles can also be used to address different special issues when performing a tissue implant insertion. With respect to FIG. 42, there is shown an embodiment of an introducer device 4210 having an introducer needle 4220 having a generally halo shape. A proximal needle shaft that extends straight from a handle 4211. At a transition bend 4223, needle 4220 bends approximately 90 degrees, where it transitions to distal curved section 4225. Curved section 4225 is subsisting in a single plane, perpendicular to shaft 4221. Shaft 4221 is outside curved section 4225. At insertion the physician can easily tell where a needle tip 4230 will emerge, as curved section 4225 is in one plane. The physician need only rotate the handle 4211 to drive curved section 4225 through the patient with a twist of the wrist.

Figure 42C:
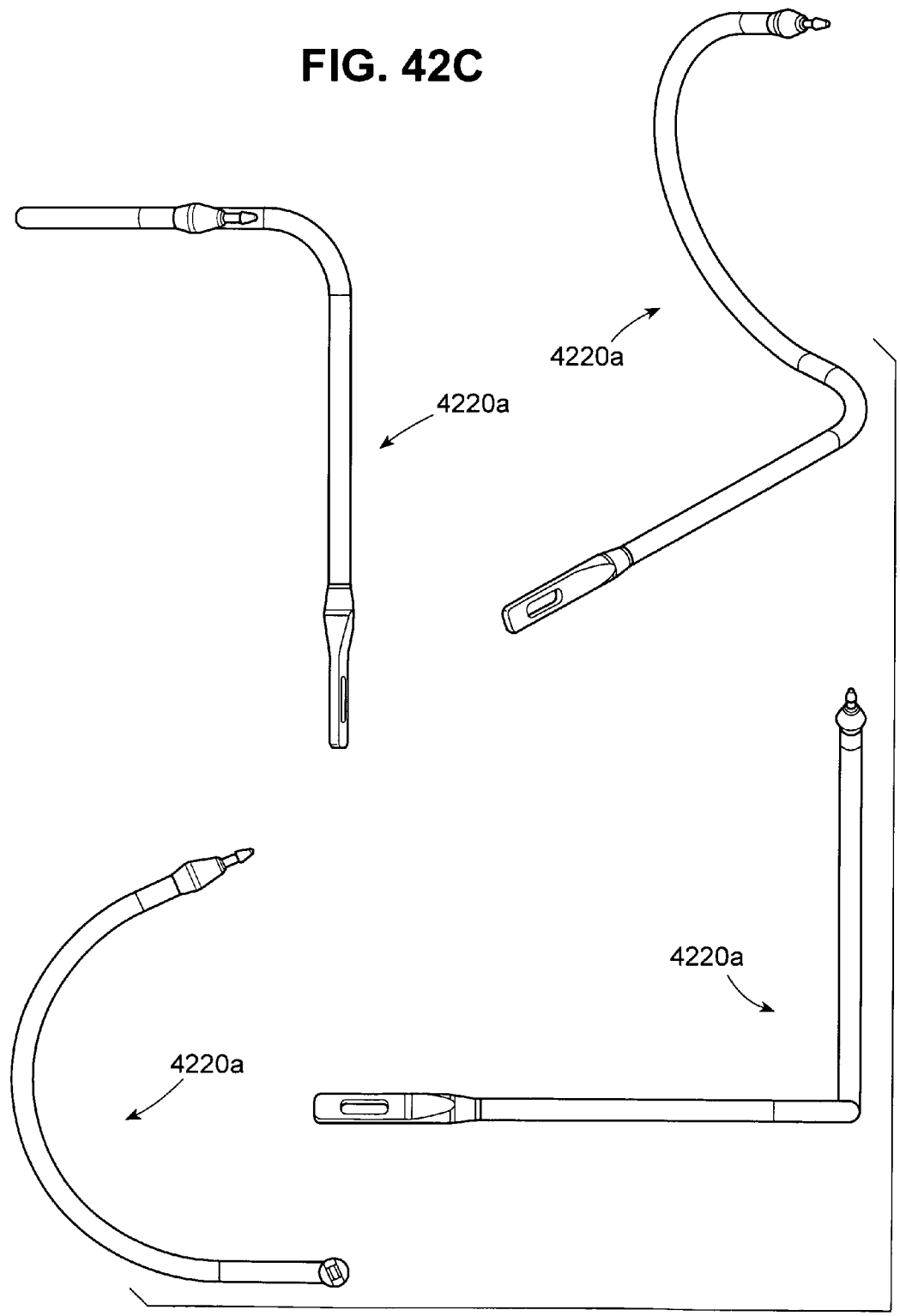
FIG. 42C shows four views of a halo shaped needle forming a curvature shaped to the right.
Figure 42D:
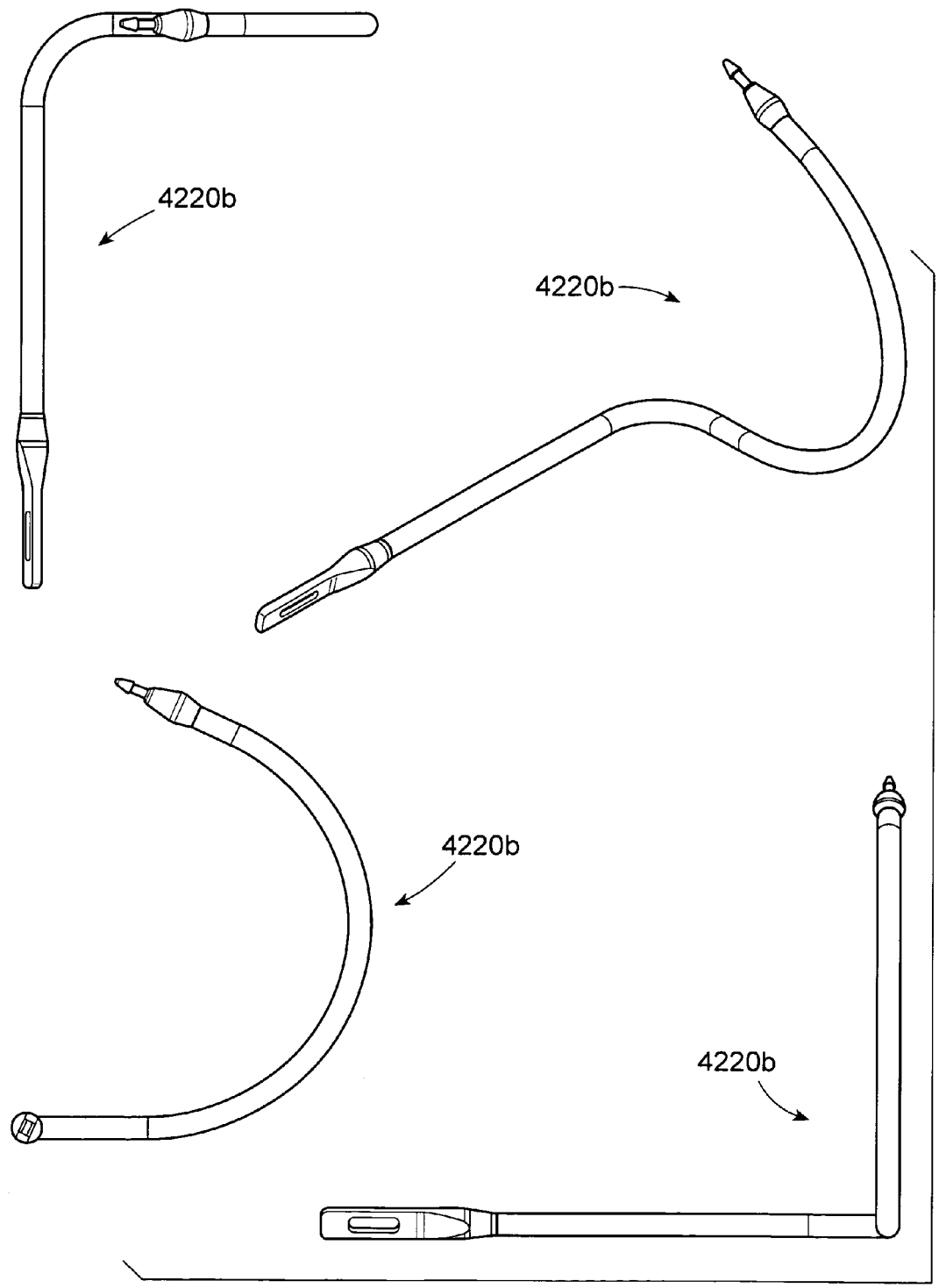
FIG. 42D shows four views of a halo shaped needle forming a curvature shaped to the left.
Figure 43:
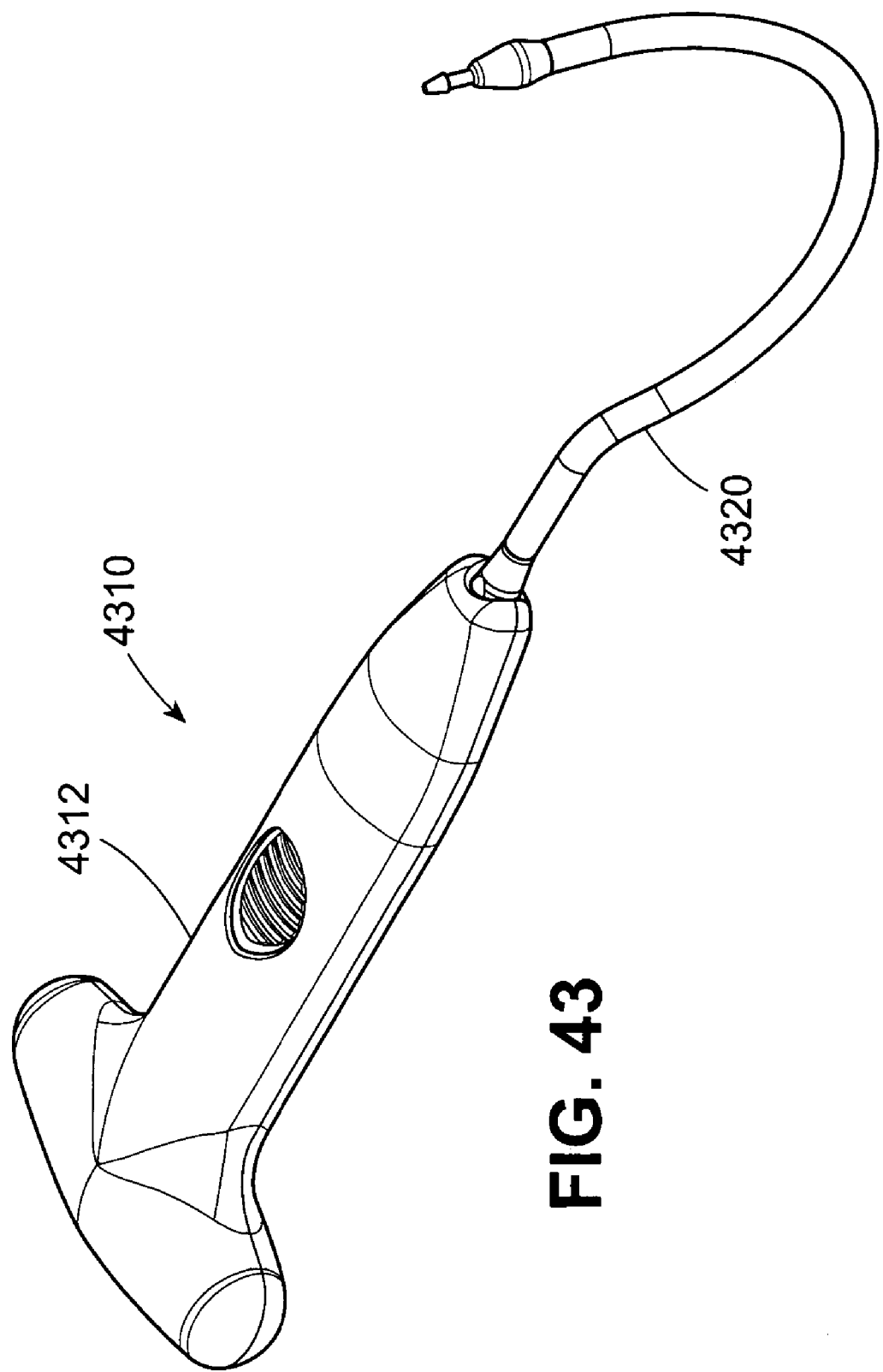
FIG. 43 is a perspective view of an introducer assembly having an introducer needle, lying in a single plane.
Figure 44:
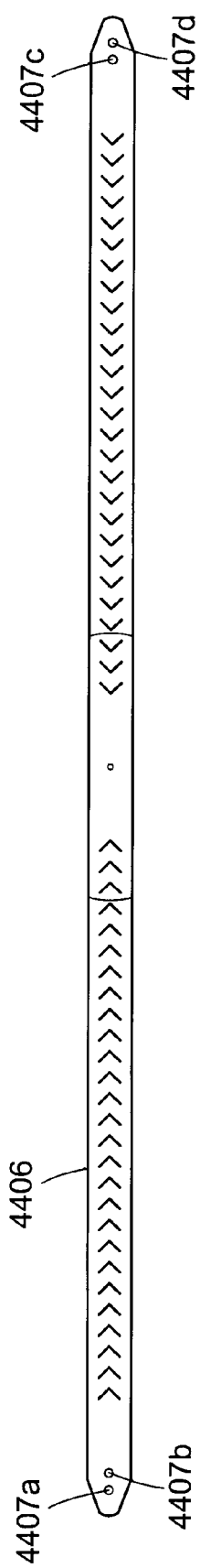
FIG. 44 is a perspective view of an implant strip.
Figure 45:
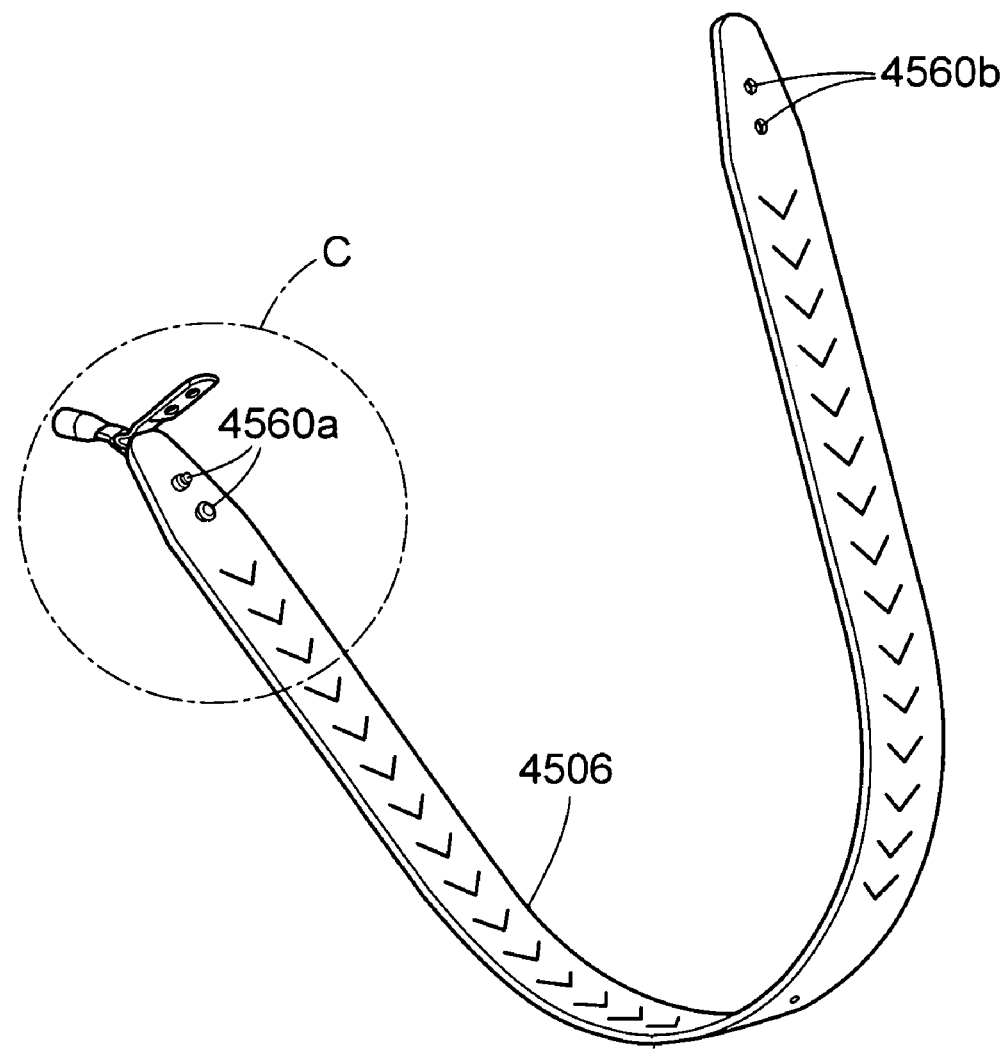
FIG. 45 is a perspective view of the implant strip and detachable connectors.
Figure 46:
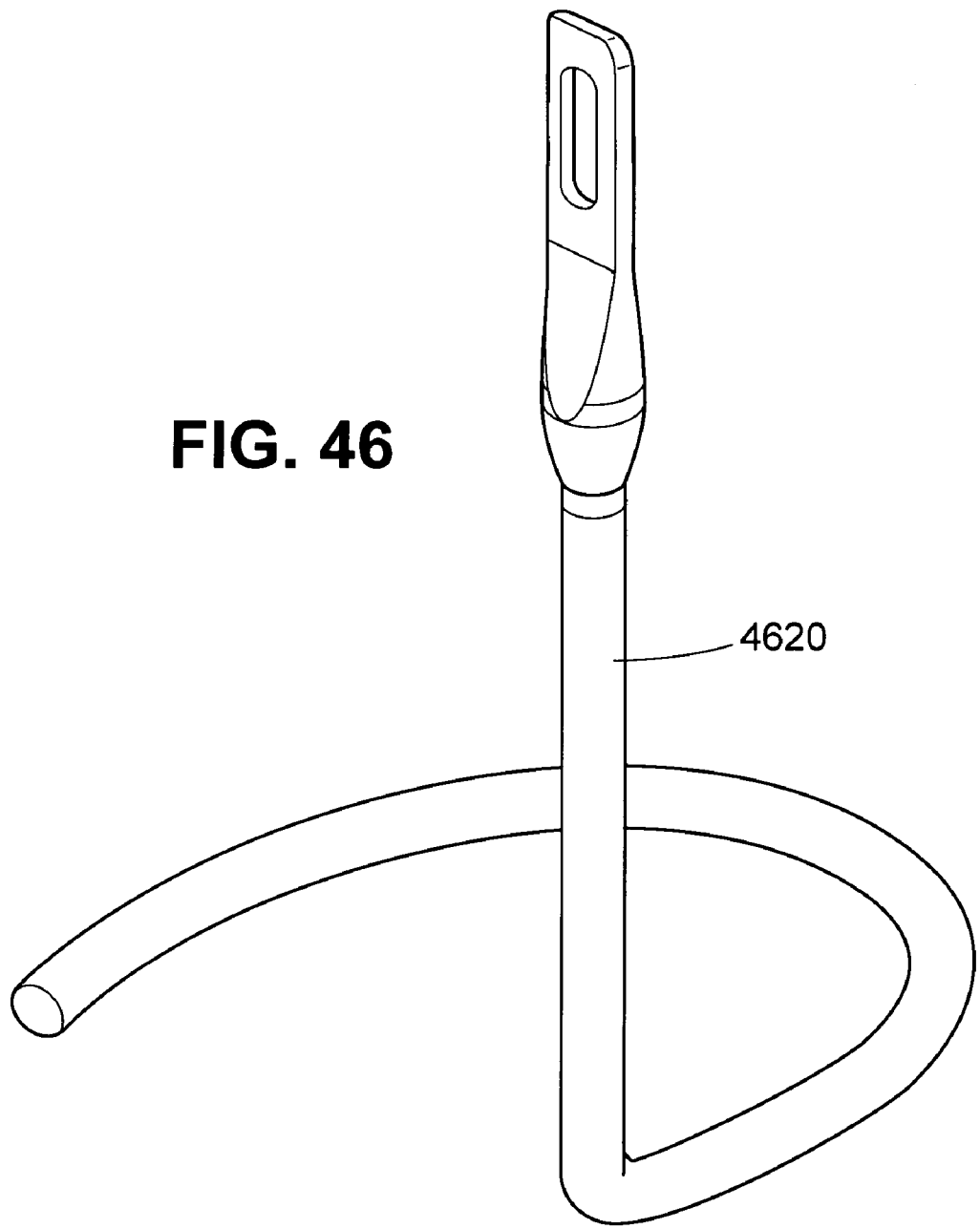
FIG. 46 is a perspective view of a detachable horseshoe shaped introducer needle.

FIG. 42A shows a halo needle assembly 4220a without an introducer handle. Needle 4220a curves in the opposite direction of needle 4220, for use on the other side of the patient. FIG. 42B shows introducer needle 4220 with a connector 4260 and a tissue implant 4206. FIG. 42C shows various views of introducer needle 4220a which is a halo shaped needle forming the curvature of which is shaped to the right. Conversely FIG. 42D shows a halo shaped needle 4220b with a curvature to the left. It should be appreciated that these different directional shapings allow more maneuverability depending on the procedure being performed or the hand being used for the procedure. FIG. 43 shows an embodiment of an introducer device 4310 having an introducer handle 4312 and an introducer needle 4320 having generally shaped in a 2 dimensional hook shape. FIG. 44 shows an embodiment of a tissue implant 4406 having apertures for connection 4407a, 4407b, 4407c and 4407d. FIG. 45 shows a tissue implant 4506 aligned to be connected to at connectors 4560a and 4560b at both the tissue implant ends. FIG. 46 is directed to a horseshoe-shaped halo introducer needle 4620. These different geometrical shapes have different benefits depending on the procedure being performed, on whom the procedure is being performed and on who is performing the procedure. For example, the use of a hook requires the one introducing the needle to move their hand from one side to the other in order to introduce the needle properly. Conversely the helical and horseshoe shapes requires more of a wrist motion by the introducer in order to properly place the needle. Additionally, while when using a helical shaped needle it can be difficult to determine where the needle is going to exit, in a horseshoe shaped needle the needle is always perpendicular to the handle and it is therefore easier to position and predict the exit location and path of travel.

Figure 47A:
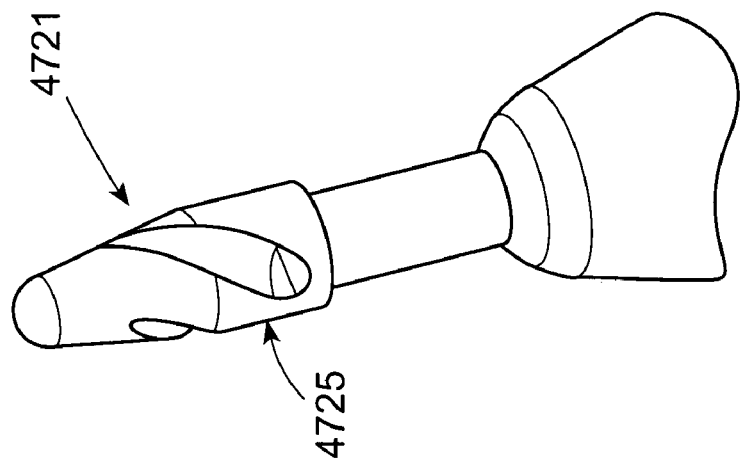
FIGS. 47 and 47A show one embodiment of a needle tip wherein the connection is twisted thereon.
Figure 47:
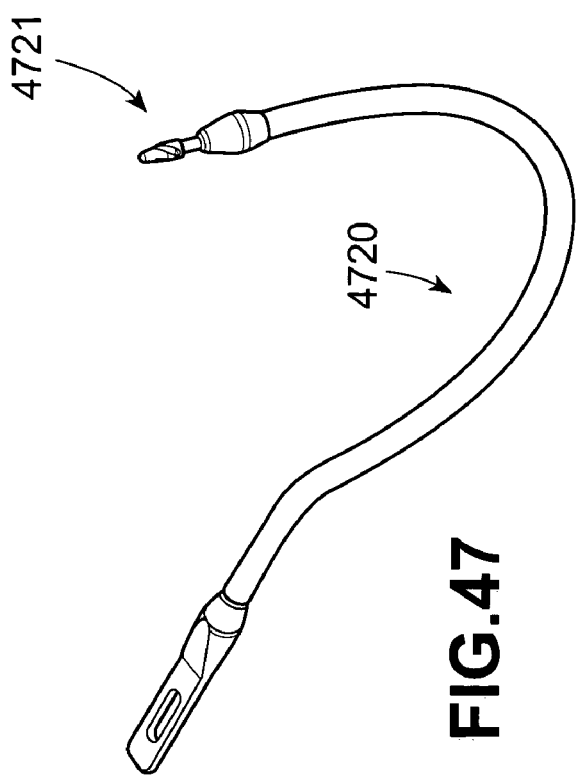
Figure 48A:
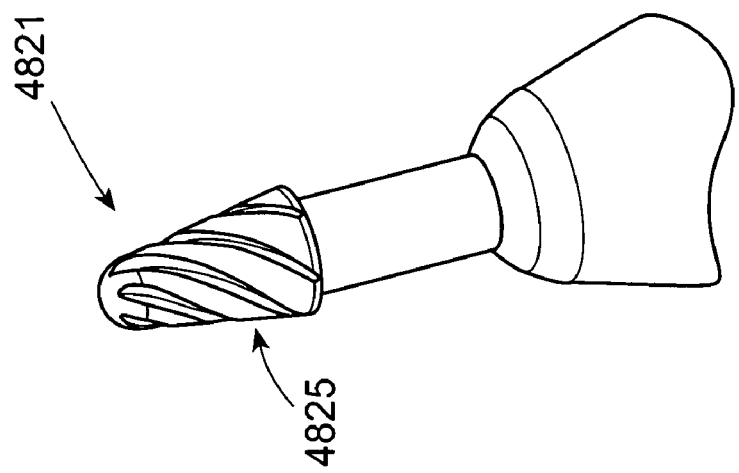
FIGS. 48 and 48A show another embodiment of a needle tip wherein the connection is twisted thereon.
Figure 48:
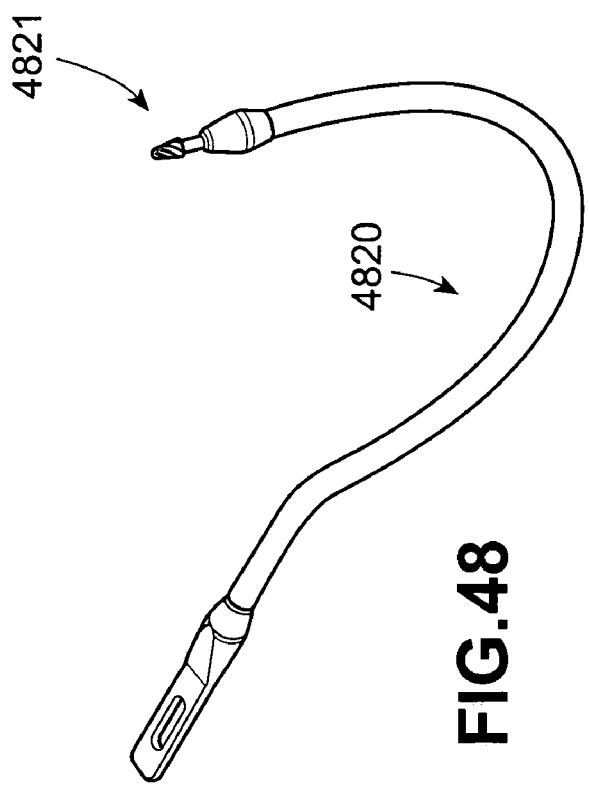
Figure 49A:
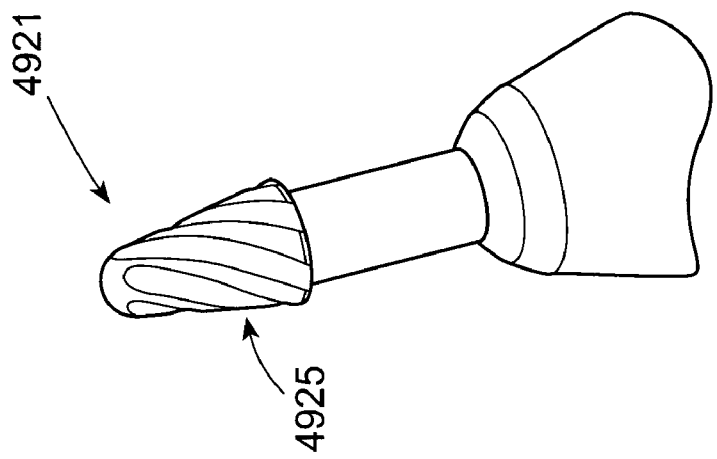
FIGS. 49 and 49A show another embodiment of a needle tip wherein the connection is twisted thereon.
Figure 49:
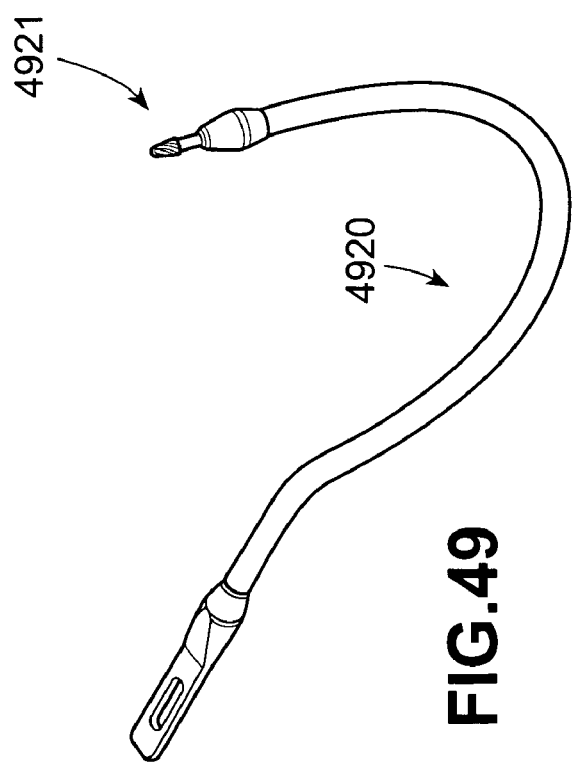
Figure 50A:
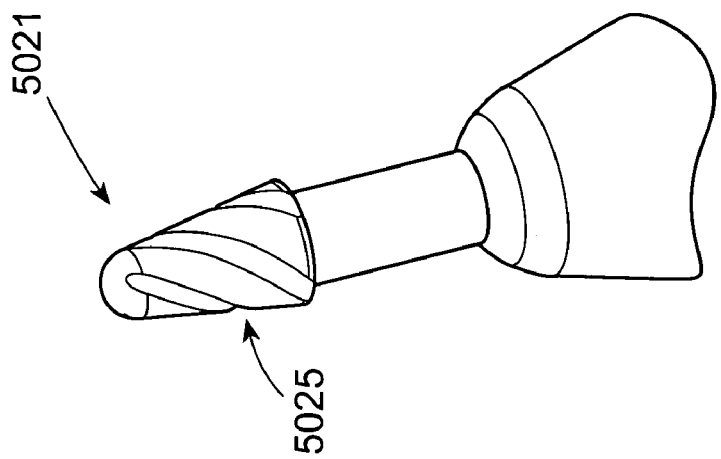
FIGS. 50 and 50A show another embodiment of a needle tip wherein the connection is twisted thereon.
Figure 50:
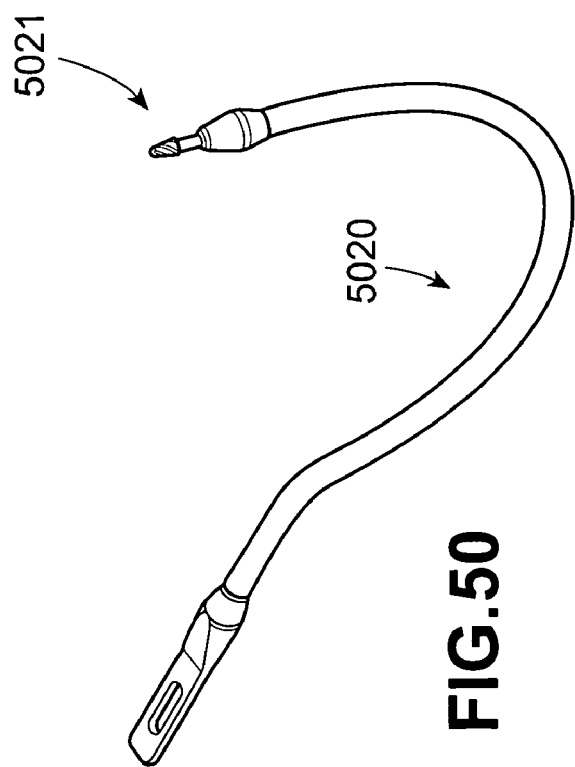
Figure 51A:
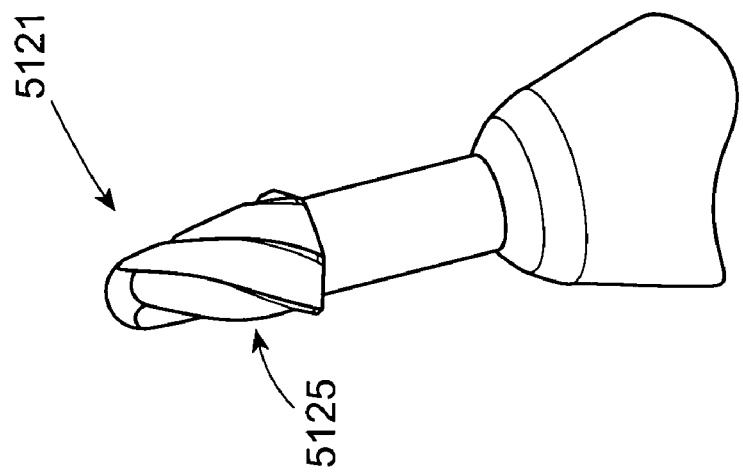
FIGS. 51 and 51A show another embodiment of a needle tip wherein the connection is twisted thereon.
Figure 51:
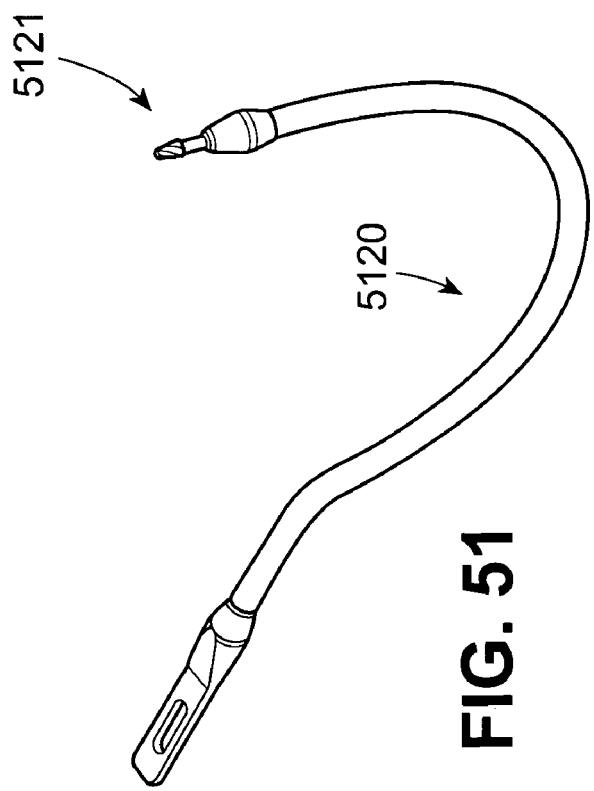
Figure 52A:
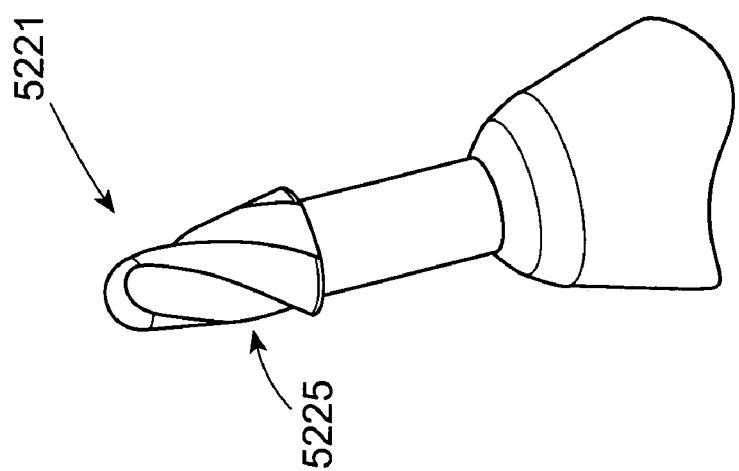
FIGS. 52 and 52A show another embodiment of a needle tip wherein the connection is twisted thereon.
Figure 52:
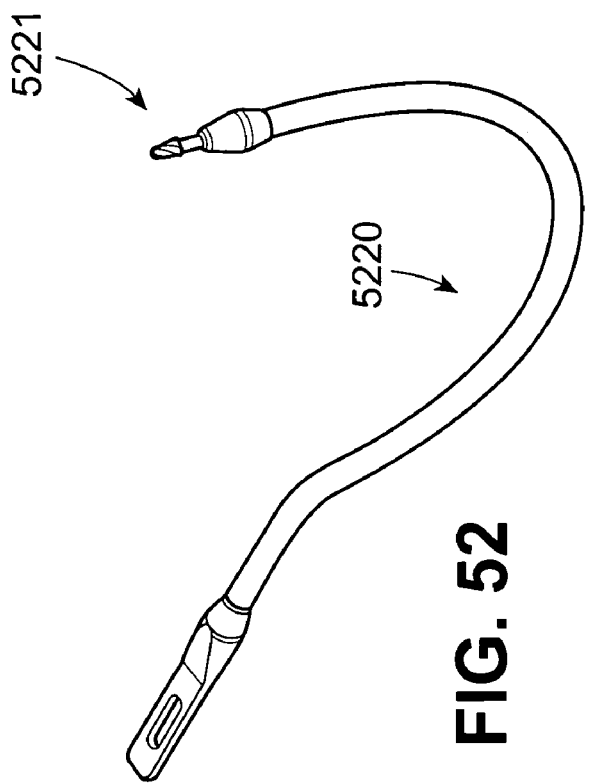
Figure 53A:
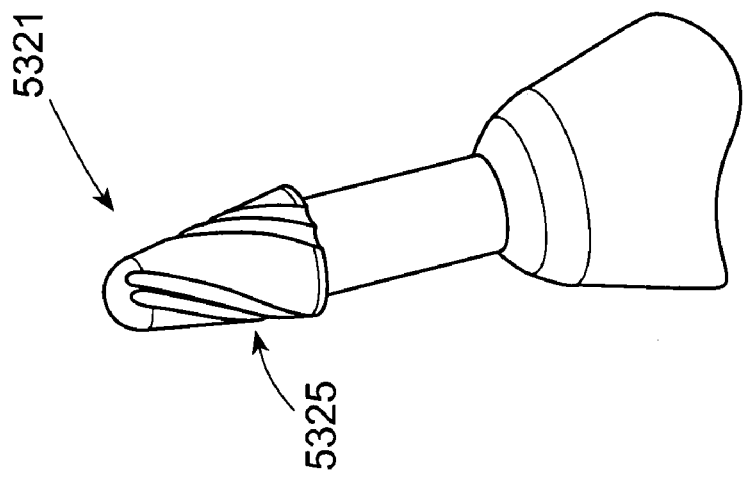
FIGS. 53 and 53A show another embodiment of a needle tip wherein the connection is twisted thereon.
Figure 53:
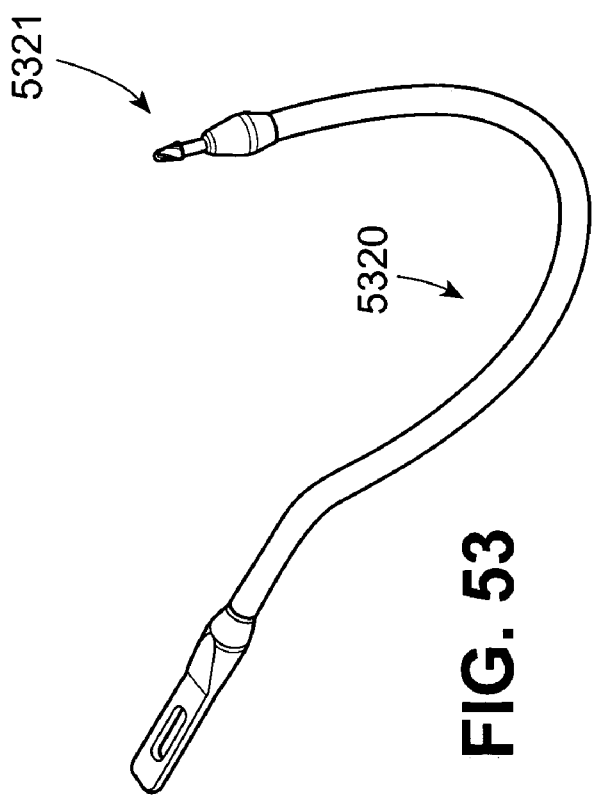
Figure 54A:
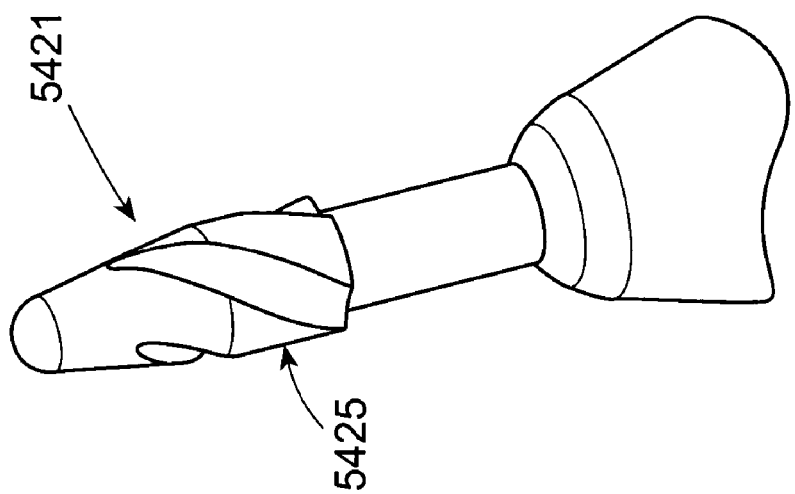
FIGS. 54 and 54A show another embodiment of a needle tip wherein the connection is twisted thereon.
Figure 54:
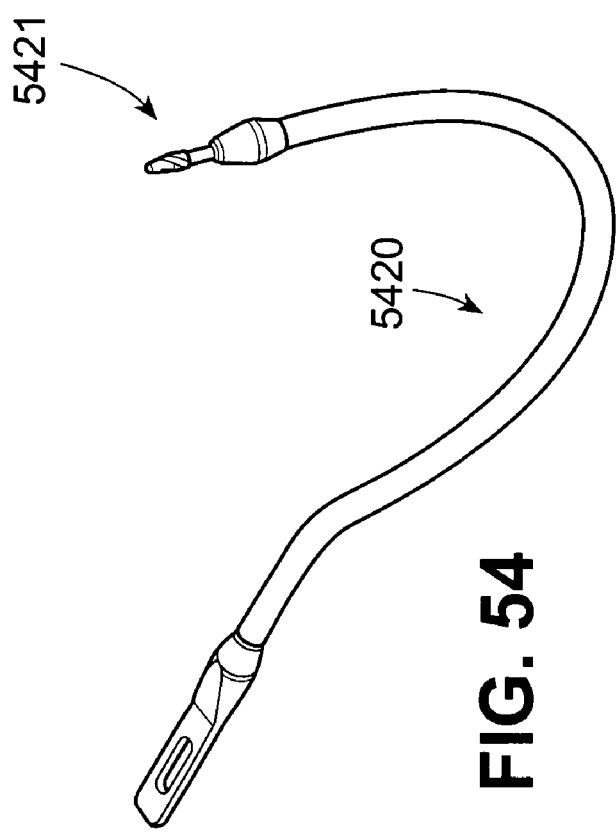

Different shaped needle tips can also be used to connect with the connector. With respect to FIGS. 47 and 47A there is shown an introducer needle that 4720 that has a needle tip 4721 that has one thread 4725 towards the center of the needle tip. A connector tube is twisted onto this style of tips rather than being merely pushed on. FIGS. 48 and 48A show an introducer needle 4820 that has a needle tip 4821 that has a plurality of threads 4825 that ease insertion when the connector is twisted thereon. With respect to FIGS. 49 and 49A, an introducer needle 4920 is shown with a needle tip 4921 that has steep threads 4925, providing a slightly different joint with the connector. FIGS. 50 and 50A show an introducer needle 5020 with a needle tip 5021 that has larger and steeper threads 5025. FIGS. 51 and 51A show an introducer needle 5120 that has that has a needle tip 5121 which contains threads 5125 that protrude from the surface. With respect to FIGS. 52 and 52A, an introducer needle 5220 is shown that has a needle tip 5221 that has a thread 5225 that protrudes from the surface. FIGS. 53 and 53A illustrate introducer needle 5320 that has a needle tip 5321 that contains a pair of threads 5325 that are close together. FIGS. 54 and 54A show an introducer needle 5420 with a needle tip 5425 that has a thread 5421 that does not reach all the way to the top of needle tip 5421. In different embodiments, a connector tube used in connection the different threads of the needles discussed above can have a mating structure that compliments the threads on the needle to make for an easier attachment.

Thus, while there have been shown and described and pointed out novel features of the present invention as applied to preferred embodiments thereof, it will be understood that various omissions and substitutions and changes in the form and details of the disclosed invention may be made by those skilled in the art without departing from the spirit of the invention. It is the intention, therefore, to be limited only as indicated by the scope of the claims appended hereto.

It is also to be understood that the following claims are intended to cover all of the generic and specific features of the invention herein described and all statements of the scope of the invention which, as a matter of language, might be said to fall therebetween.

What is claimed is:

1. A connector for attachment to an implant strip having an arm having a hole therethrough and an introducer needle including a connection portion having a barb, comprising:

a central portion;

a first arm pivotally mounted to the central portion and having a first projection and a second projection extending therefrom, said first projection having an engagement head disposed at an end thereof;

a second arm pivotally mounted to the central portion and having a first hole and a recess defined therein, the first hole and the recess being positioned so that when the first arm pivots toward the second arm, the first projection is received in the first hole such that the engagement head engages the first hole, thus maintaining the first and second arms in a closed position, and the second projection is received in the recess; and a tube portion extending from said central portion and defining a tube aperture therein;

wherein said tube aperture is adapted to receive the barb such that the connector can be selectably detachably coupled to the introducer needle.

* * * * *